(12) United States Patent
Mitchell et al.

(10) Patent No.: US 11,253,317 B2
(45) Date of Patent: Feb. 22, 2022

(54) SOFT TISSUE SELECTIVE ABLATION SURGICAL SYSTEMS

(71) Applicant: Precise Light Surgical, Inc., Campbell, CA (US)

(72) Inventors: Gerald Mitchell, Los Altos, CA (US); Kenneth J. Arnold, Corralitos, CA (US)

(73) Assignee: PRECISE LIGHT SURGICAL, INC., Campbell, CA (US)

( * ) Notice: Subject to any disclaimer, the term of this patent is extended or adjusted under 35 U.S.C. 154(b) by 124 days.

(21) Appl. No.: 16/632,857

(22) PCT Filed: Mar. 19, 2018

(86) PCT No.: PCT/US2018/023144
§ 371 (c)(1),
(2) Date: Jan. 21, 2020

(87) PCT Pub. No.: WO2018/175322
PCT Pub. Date: Sep. 27, 2018

(65) Prior Publication Data
US 2020/0163715 A1    May 28, 2020

Related U.S. Application Data

(60) Provisional application No. 62/473,955, filed on Mar. 20, 2017.

(51) Int. Cl.
*A61B 18/22* (2006.01)
*A61B 18/00* (2006.01)

(52) U.S. Cl.
CPC .... *A61B 18/22* (2013.01); *A61B 2018/00601* (2013.01); *A61B 2018/00625* (2013.01);
(Continued)

(58) Field of Classification Search
CPC .......... A61B 18/22; A61B 2018/00601; A61B 2018/00625; A61B 2018/00982; A61B 2018/2222
See application file for complete search history.

(56) References Cited

U.S. PATENT DOCUMENTS 4,775,361 A    10/1988  Jacques et al.
4,887,600 A    12/1989  Watson et al.
(Continued)

FOREIGN PATENT DOCUMENTS

EP    0164751 A2    12/1985
EP    0214712 A1    3/1987
(Continued)

OTHER PUBLICATIONS

Albagli D. et al., "Inertially Confined Ablation of Biological Tissue," Lasers in the Life Sciences 6(1), pp. 55-68, 1994.
(Continued)

*Primary Examiner* — Allen Porter
*Assistant Examiner* — Skylar Lindsey Christianson
(74) *Attorney, Agent, or Firm* — Haynes Beffel & Wolfeld LLP

(57) ABSTRACT

A laser can produce pulses of light energy for tissue-type selective ejection of a volume of the target tissue, and the energy can be delivered to a treatment site through a waveguide, such as a fiber optic waveguide. The incident laser energy can be absorbed within a volume of the target tissue with a tissue penetration depth and pulse direction such that the propagation of the energy from the tissue volume is inhibited and such that the target tissue within the volume reaches the spinodal threshold of decomposition and ejects the volume, for example without substantial damage to tissue adjacent the ejected volume. The pulses are set to be tissue selective.

41 Claims, 22 Drawing Sheets

(52) U.S. Cl.
CPC .............. *A61B 2018/00982* (2013.01); *A61B 2018/2222* (2013.01)

(56) References Cited

U.S. PATENT DOCUMENTS

| | | | |
|---|---|---|---|
| 4,965,803 A | 10/1990 | Esterowitz et al. | |
| 5,151,909 A | 9/1992 | Davenport et al. | |
| 5,390,204 A | 2/1995 | Yessik et al. | |
| 5,422,899 A | 6/1995 | Freiberg et al. | |
| 5,459,745 A | 10/1995 | Esterowtiz et al. | |
| 5,520,679 A | 5/1996 | Lin | |
| 5,591,161 A | 1/1997 | Negus et al. | |
| 5,621,745 A | 4/1997 | Yessik et al. | |
| 5,748,655 A | 5/1998 | Yessik et al. | |
| 5,782,822 A | 7/1998 | Telfair et al. | |
| 5,832,013 A | 11/1998 | Yessik et al. | |
| 5,984,916 A | 11/1999 | Lai | |
| 6,074,382 A | 6/2000 | Asah et al. | |
| 6,086,580 A | 7/2000 | Mordon et al. | |
| 6,090,102 A | 7/2000 | Telfair et al. | |
| 6,091,749 A | 7/2000 | Hoffmaster et al. | |
| 6,122,300 A | 9/2000 | Freiberg et al. | |
| 6,126,655 A | 10/2000 | Domankevitz et al. | |
| 6,156,030 A | 12/2000 | Neev | |
| 6,159,204 A | 12/2000 | Hibst | |
| 6,258,082 B1 | 7/2001 | Lin | |
| 6,309,352 B1 | 10/2001 | Oraevsky et al. | |
| 6,325,792 B1 | 12/2001 | Swinger et al. | |
| RE37,504 E | 1/2002 | Lin | |
| 6,482,199 B1 | 11/2002 | Neev | |
| 6,484,052 B1 | 11/2002 | Visuri et al. | |
| 6,503,268 B1 | 1/2003 | Neuberger et al. | |
| 6,547,780 B1 | 4/2003 | Sinofsky | |
| 6,554,825 B1 | 4/2003 | Murray et al. | |
| 6,575,964 B1 | 6/2003 | Hobart et al. | |
| 6,592,611 B1 | 7/2003 | Zawada | |
| 6,618,620 B1 | 9/2003 | Freundlich et al. | |
| 6,743,221 B1 | 6/2004 | Hobart et al. | |
| 6,749,602 B2 | 6/2004 | Sierra et al. | |
| 6,751,490 B2 | 6/2004 | Esenaliev et al. | |
| 6,986,764 B2 | 1/2006 | Davenport et al. | |
| 6,998,567 B2 | 2/2006 | Yeik | |
| 8,029,501 B2 | 10/2011 | Miller | |
| 8,202,268 B1 | 6/2012 | Wells et al. | |
| 8,353,899 B1 | 1/2013 | Wells et al. | |
| 8,394,359 B1 | 3/2013 | O'Neil | |
| 8,636,726 B1 | 1/2014 | Wells et al. | |
| 8,881,735 B2 | 11/2014 | Mitchell et al. | |
| 9,622,819 B2 | 4/2017 | Mitchell et al. | |
| 2001/0001818 A1 | 5/2001 | Hibst | |
| 2001/0016732 A1 | 8/2001 | Hobart et al. | |
| 2003/0109860 A1 | 6/2003 | Black | |
| 2003/0216719 A1 | 11/2003 | Debenedictis et al. | |
| 2004/0082940 A1 | 4/2004 | Black et al. | |
| 2004/0151217 A1 | 8/2004 | Yeik | |
| 2004/0182416 A1 | 9/2004 | Allen et al. | |
| 2004/0195221 A1 | 10/2004 | Haglund, Jr. et al. | |
| 2004/0254567 A1* | 12/2004 | Holz | A61F 9/008 606/4 |
| 2005/0049582 A1 | 3/2005 | DeBenedictis et al. | |
| 2005/0224460 A1 | 10/2005 | Hutson et al. | |
| 2005/0288653 A1 | 12/2005 | Lai et al. | |
| 2006/0016790 A1 | 1/2006 | Yeik | |
| 2006/0153254 A1 | 7/2006 | Franjic et al. | |
| 2006/0153265 A1 | 7/2006 | Geiger et al. | |
| 2006/0195072 A1 | 8/2006 | Miller | |
| 2007/0265605 A1 | 11/2007 | Vaynberg et al. | |
| 2007/0265606 A1 | 11/2007 | DeBenedictis et al. | |
| 2007/0276359 A1 | 11/2007 | Segal | |
| 2007/0299486 A1 | 12/2007 | Hoenig et al. | |
| 2008/0015556 A1 | 1/2008 | Chan et al. | |
| 2008/0086118 A1 | 4/2008 | Lai et al. | |
| 2009/0069871 A1 | 3/2009 | Mahadevan-Jansen et al. | |
| 2009/0118720 A1 | 5/2009 | Black et al. | |
| 2009/0227992 A1 | 9/2009 | Nir et al. | |
| 2010/0100084 A1 | 4/2010 | Girard et al. | |
| 2010/0305555 A1 | 12/2010 | Hutson et al. | |
| 2011/0196355 A1* | 8/2011 | Mitchell | A61B 18/22 606/11 |
| 2011/0215076 A1 | 9/2011 | Littlewood et al. | |
| 2012/0232534 A1 | 9/2012 | Rink et al. | |
| 2014/0194770 A1 | 7/2014 | McMillan | |
| 2014/0200511 A1 | 7/2014 | Boyden et al. | |
| 2014/0276690 A1 | 9/2014 | Grace | |
| 2014/0371736 A1 | 12/2014 | Levin et al. | |
| 2015/0014891 A1 | 1/2015 | Amatucci et al. | |
| 2015/0057647 A1* | 2/2015 | Mitchell | A61B 18/22 606/11 |
| 2015/0238259 A1 | 8/2015 | Albeck et al. | |
| 2017/0189117 A1 | 7/2017 | Mitchell et al. | |
| 2018/0214210 A1 | 8/2018 | Mitchell et al. | |

FOREIGN PATENT DOCUMENTS

| | | |
|---|---|---|
| EP | 2119408 A1 | 11/2009 |
| JP | 2004-261288 A | 9/2004 |
| JP | 2006-320749 A | 11/2006 |
| WO | 99/38572 A2 | 8/1999 |
| WO | 2008008499 A2 | 1/2008 |
| WO | 2010059734 A1 | 5/2010 |
| WO | WO-2010059734 A1 * | 5/2010 ............. A61B 18/22 |
| WO | 2011133941 A2 | 10/2011 |
| WO | 2018175322 A1 | 9/2018 |

OTHER PUBLICATIONS

Apitz I. et al., "Material ejection in nanosecond Er:YAG laser ablation of water, liver, and skin," Appl Phys A 81, 329-338, 2005.
Definition of "around," Collins English Dictionary (Year 1991).
Dingus R.S. et al., "Gruneisen-stress induced ablation of biological tissue," SPIE vol. 1427 Laser-Tissue Interaction II, pp. 45-54, 1991.
Duan, et al., "Room temperature efficient actively Q-switched Ho:YAP laser," Mar. 16, 2009, vol. 17, No. 6, Optics Express.
El-Sherif et al., "Soft and hard tissue ablation with short-pulse high peak power and continuous thulium-silica fibre lasers," Lasers in Medical Science, vol. 18, No. Issue 3, Sep. 2003, pp. 139-147.
Esenaliev R.O. et al., "Studies of Acoustical and Shock Waves in the Pulsed Laser Ablation of Biotissue," Lasers in Surgery and Medicine 13:470-484, 1993.
Fried et al., High-Power Laser Vaporization of the Canine Prostate Using a 110 W Thulium Fiber Laser at 1.91 mm, Lasers in Surgery and Medicine 36:52-56 (2005).
Jacques S.L., "Role of tissue optics and pulse duration on tissue effects during high-power laser irradiation," Applied Optics 32:13, 2447-2454, 1993.
Jelinkova et al., Diode-Pumped Tm:YAP Laser for Eye Microsurgery, Proc. of SPIE vol. 6871, 68712N, (2008).
Kolev N.I., Chapter 13, "Bubble growth in superheated liquid," of vol. 2, Multiphase Flow Dynamics 2, Thermal and Mechanical Interactions, 2d ed., Springer, 2004.
Li et al., High Efficiency 2.05-um CW and AO Q-Switched Operation of Diode End-Pumped Tm,Ho:GdVO4 Laser, Laser Physics, 2008, vol. 18, No. 12, pp. 1512-1516.
Mikic B.B. et al., "On Bubble Growth Rates," Int. J. Heat Mass Transfer, vol. 13, Pergamon Press, UK, pp. 657-666, 1970.
Oraevsky A.A. et al., "Mechanism of laser ablation for aqueous media irradiated under confined-stress conditions," J. Appl. Phys. 78(2), 1281-1290, 1995.
Oraevsky et al., Pulsed Laser Ablation of Soft Tissues, Gels, and Aqueous Solutions at Temperatures Below 100 C, Lasers in Surgery and Medicine 18:231-240 (1996).
Payne B., "The Role of Chromophore on Pulsed Laser Ablation of Biological Tissue," Jan. 17, 1997, M.S. thesis, MIT, 67 pp.
Plesset M.S. et al. "Bubble Dynamics and Cavitation," Ann. Rev. Fluid Mech. 9:145-85, 1977.
Plesset M.S. et al., "The Growth of Vapor Bubbles in Superheated Liquids*", J. Appl. Phys. 25(4):493-500, 1954.
Robinson A.J. et al., "The dynamics of spherical bubble growth," Int. J. Heat Mass Transfer 47:5101-5113, 2004.

(56) References Cited

OTHER PUBLICATIONS

Venugopalan V. et al., "Thermodynamic Response of Soft Biological Tissues to Pulsed Infrared-Laser Irradiation," Biophysical Journal 70:2981-2993, 1996.
Vogel A. et al., "Mechanisms of Pulsed Laser Ablation of Biological Tissues," Chem. Rev. 103(2), 577-644, Feb. 12, 2003.
Vogel et al., Minimization of thermo-mechanical side effects in IR ablation by use of Q-switched double pulses, Proc. SPIE vol. 4257A, Laser Tissue Interaction XII, Jul. 9, 2001. 184.
EP 18771778.0—Extended European Search Report dated Aug. 18, 2020, 10 pages.

* cited by examiner

SOFT TISSUE SELECTIVE ABLATION SURGICAL SYSTEMS

BACKGROUND OF THE INVENTION

Field of the Invention

Well controlled tissue-type selective removal of tissue can be an important aspect of surgery. In at least some instances the ability of a surgeon to perform an incision preserving adjacent tissues of a different type, such as nerves and vessels, in the sense that the additional tissues are kept safe from serious injury or harm, can be clinically helpful.

Description of Related Art

For many surgical procedures, it would be beneficial to avoid, or at least decrease, injury to the adjacent tissue. Furthermore, it can be beneficial for a surgeon to use a resection tool that is capable of reaching a remote surgical site, such as a treatment site accessed endoscopically, and to have a tool that provides for tissue-type selective removal of tissues.

A variety of tools have been developed to remove vascular soft tissue, cartilage and bone during surgical procedures, and many of these prior tools can be less than ideal for tissue cutting, for example of an internal surgical site. Mechanical instruments such as scalpels, biters and curettes, along with powered mechanical instruments such as microdebriders and drills, have been employed. Mechanical devices may cut tissue with varying degrees of localization and in at least some instances can induce mechanical trauma to the tissue. Although energy delivery based devices such as radio frequency, ultrasonic, and lasers have been used for tissue removal, these devices can have disadvantages, in at least some instances. For example, when tissue is inadvertently removed or damaged by mechanical or thermal injury, the clinical outcome and patient recovery can be adversely affected, in at least some instances. Also, in prior art approaches, care must be taken to avoid ablation of tissue types that are not target of the operation.

Flash Vaporization is a class of laser surgery technology which addresses some of the problems discussed above. See, U.S. Pat. No. 9,844,410 entitled Flash Vaporization Surgical Systems, issued 19 Dec. 2017, which is incorporated by reference as if fully set forth herein.

Therefore, it would be helpful to provide improved methods and apparatuses for cutting tissue that overcome at least some of the above limitations of the prior systems. Ideally, such methods and apparatuses would provide surgeons a fast and effective, tissue-selective cutting tool with flexibility to perform many sizes of tissue resections with precise localization, including cutting tissue without substantial thermal or mechanical damage to the tissue adjacent to the cut, for example. It would also be helpful if such methods and apparatuses could allow for ablating tissue of a first type without ablating tissue of a second type. Additionally, methods and apparatuses for tissue cutting that are selectively applicable to a broad variety of tissue types may be important to surgeons and/or necessary to effectively perform certain procedures.

BRIEF SUMMARY

Methods and apparatuses are described to quickly and efficiently remove and resect a target tissue having a target tissue type without substantial thermal or mechanical damage to the adjacent tissue of the same or similar tissue type; and which in addition, are selective for removing the target tissue type over other tissue types. As a result, structures that comprise a different tissue soft type adjacent to the target tissue can be preserved in surgery removing the target tissue. These technologies address the problems discussed above, improving the safety of laser surgery, and enable new classes of laser surgery.

A laser surgery system is described which produces a pulsed laser beam configured to cause removal of certain tissue types while simultaneously not causing removal of other tissue types in the target field of the surgery. A new method is provided that includes moving a pulsed laser beam along a boundary between first and second soft tissue types within a surgical field to selectively remove the first soft tissue type relative to tissue of the second soft tissue type.

In many surgical applications it is desirable to remove target tissues without removing other tissue types in the vicinity of the target tissue. For example, removing diseased tissue located immediately adjacent to, or surrounding, a nerve. In this instance it is desirable to remove the diseased tissue without removing or damaging the nerve itself. Certain vessels can also be preserved, with no appreciable tissue removal, while simultaneously removing adjacent tissues. Another example involves selective removal of tissue layers in an anatomical structure. In Gastroenterology for example, it may be advantageous to remove diseased mucosal tissues while not removing muscularis tissue. In this instance, the diseased target tissue can be removed while preserving the non-diseased structural tissues. Furthermore, the selective tissue removal can even be applied to the same tissue type when disease or other factors have altered the tissue properties. for example, a brain tumor where the removal of tissue can selectively discriminate between healthy and malignant brain tissues. Selective tissue removal offers numerous advantages for surgeons and benefits for patients. Selective tissue removal can be applied in many ways, including to preserve key structures like nerves and vessels, to safely remove tissue layers, like mucosal tissues and to remove tumors with optimal margins. This selective removal of tissue improves the safety margin in laser-based surgical systems.

As described in detail below, a laser surgery system which produces pulse sequences that are configured to cause removal of certain tissue, while simultaneously not causing removal of other tissue types in the target field of the surgery, is based on utilizing Flash Vaporization, including inducing spinodal decomposition, as described herein.

As described herein, both the differences between ablation thresholds to induce flash vaporization for different soft tissue types are substantial, allowing tuning of laser parameters for target soft tissues. Also, the effects of the laser pulses set above threshold for a target soft tissue, but below threshold for different a soft tissue type, are minor in some cases. As a result of these differences, laser ablation along a boundary between different types of soft tissue can be self-aligned, stopping at the boundary between different soft tissue types by setting the laser parameters above the flash vaporization threshold of one soft tissue type (the type to be removed), and below the flash vaporization threshold of another soft tissue type (the type forming the boundary). In some cases, the soft tissue forming the boundary is not harmed, or not significantly harmed so that it heals without substantial loss of tissue volume. In some cases, the soft tissue forming the boundary can protect underlying, more vulnerable or more functionally critical soft tissues from harm during removal of the target soft tissue. Soft tissue types include tissue types that connect, support, or surround other structures and organs of the body. Soft tissue includes muscles, tendons, ligaments, fascia, nerves, fibrous tissues, fat, blood vessels, and synovial membranes, and excludes bones, tooth enamel, dentin and cementum. As a result, setting laser parameters above a threshold for a first tissue type, but below a threshold for a second tissue type, where the second tissue type can include soft tissue types, a new surgical technique is provided, by which the second tissue type behaves as an ablation stop, defining a boundary of the ablation along the boundary between the tissue types. The second tissue type is not destroyed, and in at least some cases not seriously harmed, by laser pulses set at the threshold for the first tissue type, while the first tissue type is ablated by flash vaporization without substantial thermal damage to adjacent tissues of either the first or second tissue types.

DETAILED DESCRIPTION

Figure 1A:
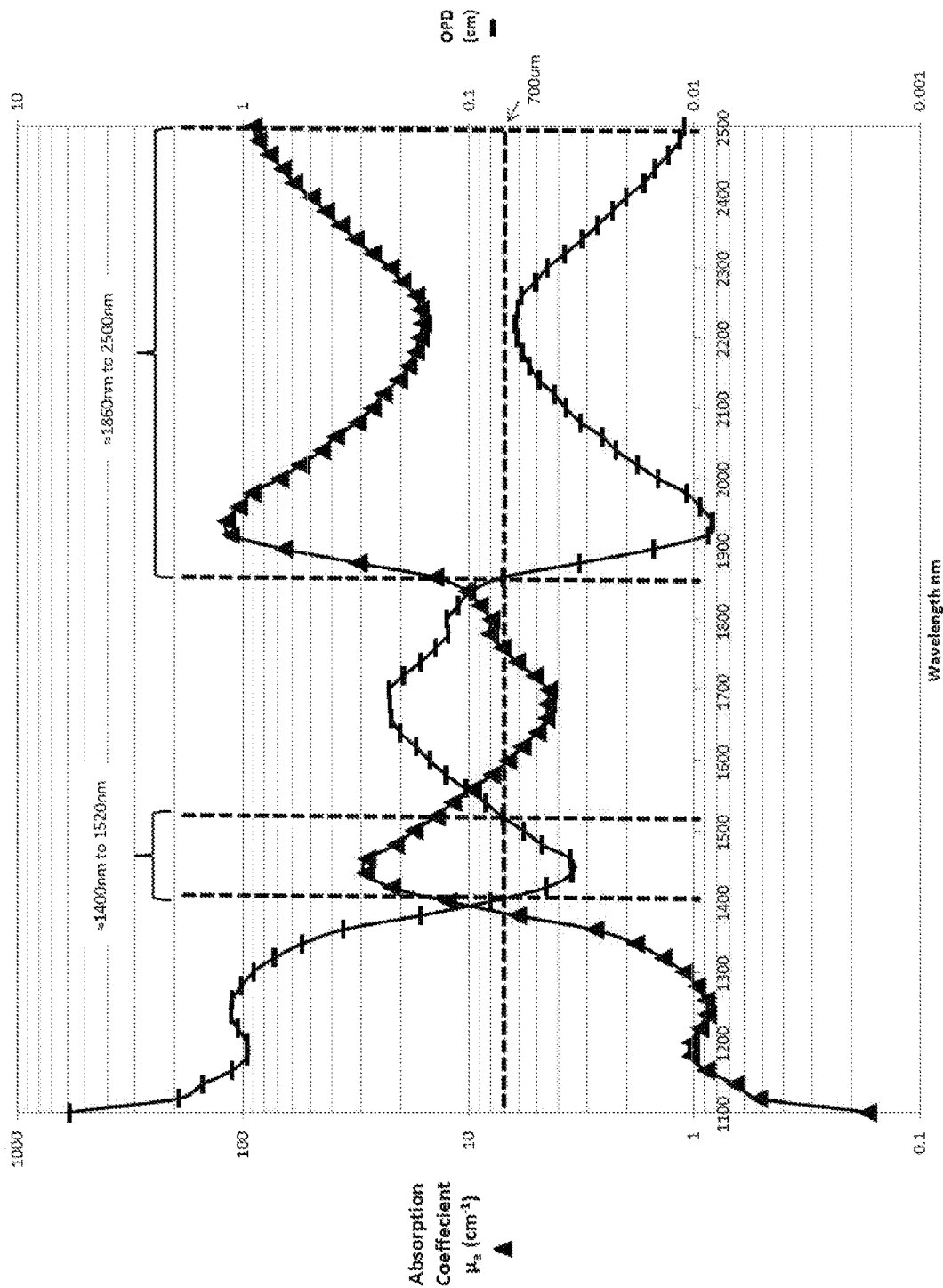
FIGS. 1A-1B show the absorption coefficient and optical penetration depth (hereinafter "OPD") in water as a function of wavelength.

Embodiments of the present invention as described herein provide fast and efficient laser based cutting. The laser based cutting modality as described herein is applicable to a variety of tissue types and surgeries, such that there is no substantial thermal or mechanical damage or effect on the tissue adjacent to the cut. The spinodal decomposition process generates pressure within the target tissue volume. The pressure is generated, in part, when the chromophore, for example water, in the target volume reaches or exceeds the spinodal threshold, thus initiating spinodal decomposition, on a time scale sufficient to substantially prevent propagation of thermal or mechanical energy beyond the target volume. The pressure generated ejects material from the target site. The amount of pressure to adequately or optimally eject substantially all of the target volume is, in part, dependent upon the mechanical properties of the tissue itself. Various tissue types have different mechanical properties, in part, due to the collagen structure of each tissue type.

In embodiments of the tissue selective ablation method and apparatus described herein, for a given tissue, there is a threshold pressure required to remove that tissue. When a pressure greater than the threshold is achieved the tissue will be removed. When the pressure generated is below the threshold, no appreciable tissue will be removed. The pressure achieved within the tissue is dependent on certain characteristics of the target tissue and the system parameters.

The system parameters are adjustable to accommodate the types of tissue to achieve the desired result. Assume tissue type A and tissue type B, where tissue type A is the target tissue to be removed and tissue type B is adjacent tissue that is desirable to preserve. If parameters are chosen such that the pressure generated in both tissue type A and type B is below their respective thresholds then both tissue type A and type B will not be removed. If parameters are chosen such that the pressure generated in both tissue type A and type B is above their respective thresholds then both tissue types will be removed. If the parameters are chosen such that the pressure generated within tissue type A is above tissue type A's threshold and the same parameters generate a pressure in tissue type B that is below tissue type B's threshold then tissue A will be removed while tissue B will not be removed.

Achieving sufficient pressure within the tissue to cut the tissue is dependent upon various system parameters, including in part; pulse energy, wavelength, spot size, and pulse duration. Each parameter must comply with one or more required conditions that, in combination, lead to tissue cutting of a target tissue type via high peak pressure. If one parameter is not compliant for the target tissue type, then tissue cutting via high peak pressure will not occur. Directly measuring the pressure generated by a parameter set in a given tissue is very difficult. Therefore, comparing a calculated pressure threshold value for a target tissue type to the actual pressure generated is not practical. Threshold values for a target tissue type are primarily determined experimentally. Initial calculations are made to provide a set of parameters where changing one parameter, such as pulse energy or spot size, allows the system to meet or not meet the threshold pressure for cutting a target tissue.

In the examples cited below, all but one parameter was fixed. Pulse energy was chosen to be the variable parameter, primarily because it is convenient to change for these experiments, as compared to say wavelength or even spot size. It is also acceptable to have fixed the pulse energy and varied a different parameter to achieve the same result.

Nerve mobilization—In a porcine model, parameters were set to generate pressures above threshold for the muscle, gland, fat and connective tissue types, representing the tissues immediately adjacent to and in the general area of the laryngeal nerve. These same parameters produced only sub-threshold pressures in the perineural nerve sheath material of the nerve bundle, such as the endoneurium and perineurium, that include a significant amount of fibrous connective tissue. In this case, the parameters were set to remove tissues surrounding the nerve bundle without removing the nerve tissue. The surgeon ran the probe immediately adjacent to and along the laryngeal nerve for several inches on each side of the nerve bundle to remove the connective tissues holding the nerve to the tissue bed. Once the connective tissues along the sides of the nerve bundle were removed, the surgeon reoriented the probe and removed connective tissue immediately under the nerve bundle, thus completely freeing the nerve bundle from the tissue bed, i.e. nerve mobilization. The entire mobilization was performed without any detectable injury to the nerve sheath. Injury was evaluated by intraoperative nerve monitoring and acute histologic evaluation.

To further clinically evaluate the ability to selectively preserve nerves, a potentially harmful surgical scenario was replicated in a porcine model. In this scenario, the surgeon activated the system in a single location on the nerve for 1 second. This simulates the surgeon inadvertently positioning the device tip on the actual nerve while attempting to mobilize the nerve. After a 1 second exposure, there was no injury to the nerve sheath. To assess further this process was repeated for 2 seconds, 3 seconds and 5 seconds. In each case no injury to the nerve sheath was detected.

In the nerve mobilization and nerve preserving examples, each parameter except pulse energy was fixed. The wavelength was approximately 1.9 μm, the spot size was about 80 μm. With the full parameter set, the pulse energy to exceed the nerve tissue threshold was found to be above 4.5 mj. For the surrounding connective tissues the pulse energy to exceed threshold was about 3.2 mj. For the experiment, pulse energies of 3.5-3.7 mj were used to cut the connective tissues while not cutting the nerve tissue. As a result, self-alignment of ablation to remove tissue surrounding the nerve bundle is achieved by setting the laser parameters to be tissue type selective for the surrounding tissue type relative to the nerve sheath.

There are many instances where the ability to remove tissues adjacent to nerve bundles without injuring the nerve is critical. It is also highly advantageous to have a tissue removal tool that will not injure the nerve in the event it is activated directly on the nerve bundle. Other technologies cannot preserve the nerves in this way. Other energy devices are rarely used immediately adjacent to nerves due to severe and often permanent damage to the nerve caused by heat and/or non-selective removal of the nerve tissue. A blade is commonly used to separate the nerve bundle from connective tissues. However, if the blade is inadvertently run across the nerve, the nerve will be cut and severely injured; there is no room for error. With selective tissue removal, surgeons can more safely and efficiently remove undesired tissue near nerves, even when the nerves they wish to preserve are embedded within the undesired tissue.

There are many procedures where tissue removal is performed near nerves and where it is highly desirable to maintain the function of those nerves. For example: thyroid and parathyroid, prostatectomy, face lifts and facial plastic, neuro and spine to name a few.

Tissue selective removal may significantly reduce intraoperative bleeding, even in highly vascular tissues, such as kidney tissue during a partial nephrectomy. With current resection tools, all of the kidney's vessels are resected as the cutting instrument is maneuvered through the kidney. The vast majority of vessels within the kidney are capillary with a few larger feeder and branch vessels. When all the vessels are severed, the majority of the volume of blood comes from the larger vessels, the feeder and branches. By utilizing tissue selective removal the diseased tissue and capillary vessels can be removed while not perforating or severing the larger feeder or branch vessels. In this instance, the large volume of blood that typically would have poured into the surgical field does not, because the feeder and branch vessels are not being severed or perforated. Specifically, the parameters are selected to exceed the threshold pressures required to remove the bulk kidney tissue, including capillary vessels, while those same parameters, when used on feeder or branch vessels do not produce enough pressure to exceed the threshold for feeder or branch vessels. In this example the kidney tissue would be removed except for the feeder and branch vessels. Then these larger vessels that would previously have created significant bleeding can be occluded, with a variety of methods, without any blood loss from that vessel.

In the experiments for vessel preservation, each parameter except pulse energy was fixed. The wavelength was approximately 1.9 um, the spot size was about 95 um. With the full parameter set for the pulse energy to exceed a roughly 2 mm vessel's threshold, the vessel embedded in liver tissue was found to be above 4.8 mj. For the surrounding liver tissues, the pulse energy to exceed threshold was about 4 mj. For the experiment, pulse energies of 4.2-4.5 mj were used to cut the liver tissues while not cutting the vessel tissue.

Selective tissue removal can be used to discriminate between healthy and diseased tissues of the same type, for example brain tumors. In lab experiments, surrogate tissues, one representing healthy human brain tissue and one representing malignant human brain tissue, were used. In this instance, parameters were selected to exceed the threshold pressures required to remove the healthy brain tissue while those same parameters, when used on the malignant brain tissue, did not produce enough pressure to exceed the threshold for malignant brain tissue. The use of selective tissue removal creates a resection boundary at the interface of the healthy and malignant tissue and may be used to efficiently determine margins during tumor removal.

In the example of differentiating between healthy and malignant brain tissues, each parameter except pulse energy was fixed. The wavelength was approximately 1.9 um, the spot size was about 125 um. With the full parameter set, the pulse energy to exceed the malignant tissue threshold was found to be above 3.8 mj. For the surrounding healthy brain tissues, the pulse energy to exceed threshold was about 3.5 mj. For the experiment, pulse energies of about 3.6 mj were used to cut the healthy brain tissues while not cutting the malignant brain tissues.

Mucosal and sub-mucosal tissue resections in the GI tract are examples of how selective tissue removal can improve safety and efficiency for procedures where it is important to preserve underlying layers of tissue. In this example, the surgical objective is to remove mucosa and/or sub-mucosa tissue while being very careful not to damage the underlying muscularis tissues. The muscularis is a structural component of the lumen and, if the muscularis is damaged to the point of acute or potentially worse, delayed, failure, the patient may be at great risk. In a porcine model, mucosal and sub-mucosal tissues were removed from sections of the esophagus, stomach and colon. Parameters were selected to exceed the threshold pressures required to remove the mucosal and sub-mucosal tissues while those same parameters, when used on muscularis tissue, did not produce enough pressure to exceed the threshold for muscularis. The use of selective tissue removal enabled the target tissues to be removed while substantially not removing the underlying structural tissues.

In the GI example, each parameter except pulse energy was fixed. The wavelength was approximately 1.9 um, and the spot size was about 65 um. With the full parameter set, the pulse energy to exceed the muscularis tissue threshold was found to be above 1.9 mj. For the overlying mucosal tissues, the pulse energy to exceed threshold was about 1.4 mj. For the experiment, pulse energies of 1.5-1.7 mj were used to cut the mucosal tissues while not cutting the muscularis tissue.

A controller is provided in a laser system by which parameters for a surgery are set that fall below an ejection pressure threshold for a selected protected tissue, and above a pressure threshold for a selected target tissue. In this manner, during surgery the laser is used for removing the target tissue, while mistaken contact of the protected tissue does not cause appreciable damage to the tissue.

Tissue selectivity can be clinically useful when the rate of tissue removal of the target tissue is >4× the rate of tissue removal of the tissue to be to preserved.

Flash vaporization as described herein can be used for tissue selective ablation. Flash vaporization methods for removing tissue can include producing laser pulses having a wavelength between 1880 and 2080 nm or between 2340 and 2500 nm, having between 1 and 10 millijoules per pulse, and having a pulse length less than 100 nsec; and delivering the pulses to a spot on the tissue; whereby an interaction volume defined by the area of the spot and the penetration depth (1/e) for the pulse in water has a ratio of depth to width from 2:1 to 1:6. The method can include delivering the laser pulses to the target tissue using a fiber optic having a core diameter in the range of 10 to 300, preferably 50 to 200 um. The waveguide used to deliver the pulses can comprise a silica optical fiber. The method can include utilizing pulse repetition rates from single shot to 2000 Hz.

Utilizing this method, the applied energy heats the interaction volume of the tissue above a spinodal decomposition threshold for water within the pulse duration, translating laser energy into kinetic energy, via spinodal decomposition, leading to highly efficient ejection of tissue within the interaction volume. Furthermore, the laser pulses have a pulse duration sufficiently short to prevent stress waves and heat from propagating beyond the interaction volume relative to a shortest dimension of the interaction volume. The volumetric power density delivered to each spot can be greater than $10^{10}$ W/cm$^3$ for each pulse. As a result, most, if not essentially all, of the energy of the laser pulse is dissipated in the tissue that is removed by the pulse. It is found that using this method as applied to tissue including sufficient water to produce pressure for ejection of the tissue infrastructure, and unlike any known prior art, significant volumes of tissue can be removed with no apparent thermal injury to the tissue adjacent the cavity left by the ablation.

Another more general method includes producing laser pulses having a wavelength between 1400 and 1520 nm or between 1860 and 2500 nm, having between 0.5 and 40 milliJoules per pulse, and having a pulse length less than 200 nsec, preferably less than 100 ns; and delivering the pulses to a spot on the tissue using a waveguide such as a silica optical fiber having a core diameter in a range of 50 um to 200 um. Using this technology, an interaction volume defined by the area of the spot and the penetration depth (1/e) for the pulse in water has a ratio of depth to width from 2:1 to 1:6. The energy per pulse and wavelengths can be adjusted for interaction with other chromophores, and to produce pressures needed for various tissue types within this range.

According to a more general embodiment, a method for tissue removal comprises producing laser pulses having a wavelength between 1400 and 1520 nm or between 1860 and 2500 nm, and having a pulse duration; and delivering the laser pulses to a spot on the tissue, the laser pulses having an energy per pulse ($E_p$) to heat an interaction volume of the tissue above a spinodal decomposition threshold for water within the pulse duration, and cause sufficient pressure for ejection of the target tissue, and having a pulse duration sufficiently short to prevent stress waves or heat from propagating beyond the interaction volume relative to a shortest dimension of the interaction volume. The method can be characterized more generally by the steps of producing laser pulses having a wavelength ($\lambda$) and pulse duration ($t_p$); and delivering a sequence of the laser pulses to respective spots having impact areas (A, e.g. $\pi r^2$) on the tissue and having a penetration depth in the tissue, the pulses having a nominal interaction volume in the tissue that is a function of the impact areas and the penetration depth; whereby an interaction volume defined by the area of the spot and the penetration depth (1/e) for the pulse in water, the interaction volume having a ratio of depth to width from 2:1 to 1:6.

The pulse duration in a more general genus of the method is less than 200 nsec and the pulse has a peak power density $E/(t_p A)$ below the threshold for inducing significant plasma formation. This method can comprise delivering the sequence laser pulse using a silica optical fiber, with energy and pulse duration combinations that are below the damage threshold for the silica optical fiber. The method can be further characterized by an impact area having a dimension equal to a smallest distance across the impact area, and the pulse duration is within 3 times of a stress confinement duration of the time for propagation of an acoustic wave a lesser of one-half said dimension (e.g. r) and the penetration depth. The method can include laser pulses interacting with the interaction volume with a volumetric power density greater than $10^{10}$ W/cm$^3$.

According to a species of the more general method described herein, a laser including a Tm:YAP gain medium is arranged to produce an output wavelength near 1940 nm. The laser is used to deliver a sequence of pulses to a tissue site, with an energy per pulse in the range of 1 to 10 mJ per pulse in pulse widths less than 100 nsec, with a beam delivery tool, such as a fiber optic or other waveguide. The method includes delivering the pulses to the treatment site with a spot size of 50 to 200 microns. A wavelength near 1940 nm has an optical penetration depth in water of about 80 microns. Because water is a primary component of most tissues, the penetration depth in tissue can be approximately the same. Using a spot size and an 80 micron penetration depth, one can determine the dimensions of an interaction volume within the tissue at the treatment site for a laser pulse. Using a pulse width less than 100 nsec, such as between 10 nsec and 50 nsec for a representative procedure, results in a condition of thermal and mechanical confinement of the energy dissipation from the laser pulse, within that interaction volume. Using an energy per pulse on the order of 0.5 to 40 mJ is sufficient in this example to generate greater than $5 \times 10^{10}$ W/cm$^3$ within the interaction volume and raise the temperature of the water in the interaction volume above the spinodal limit, can cause confined spinodal decomposition of the water. The spinodal decomposition results in an instantaneous phase change that creates substantial pressure in a range of about 200 bars to 10 kBars within the interaction volume at the treatment site. Energy in a pulse sufficient to induce the spinodal decomposition is translated via this confined pressure into kinetic energy that can eject the tissue without visible thermal damage to tissue adjacent the ejected volume, such as would otherwise be caused by thermal or acoustic waves induced by the ejection or the laser pulse. This effect is termed herein Flash Vaporization. The laser system according to this species can be operated with repetition rates from single shot to 2000 Hz, and because of the substantial volume of tissue ejected with each pulse, cutting rates can be achieved using Flash Vaporization that have not been possible using known prior art techniques.

Other species of the method within this more generic class can utilize lasers operating in wavelengths that have similar optical penetration depths in tissue having water as a primary component, including wavelengths between 1400 and 1520 nm or between 1860 and 2500 nm. Wavelengths in this range are also characterized by the fact that they are readily deliverable using silica waveguides on the order of 10 to 300 microns, preferably 50 to 200 microns in core diameter within the energy per pulse in the range of 0.5 to 40 mJ per pulse and pulse widths between about 10 nsec and 200 nsec. In some embodiments, the energy per pulse can range from about 100 uJ to about 100 mJ. Furthermore, many embodiments for flash tissue vaporization using water as the chromophore utilize pulse energies from 500 uJ to 30 mJ. Specific embodiments for Flash Vaporization can use water as the chromophore and a wavelength near 1.94 µm, pulse widths between 10 ns and 100 ns, and pulse energies from 1 mJ to 10 mJ. Because of the availability and biocompatibility of silica waveguides, these species of laser systems can be readily utilized in a wide variety of endoscopic laser surgeries.

As spot size increases, the energy per pulse needed to achieve ejection by spinodal decomposition increases significantly. This limits the size of a laser spot that can be practically used in laser surgery applications. Other species described herein are configured to remove larger volumes of tissue per unit time. Such species utilize lasers capable of producing outputs that are a multiple of the energy per pulse to be applied by each pulse. In such species, a delivery tool including multiple waveguides can be coupled to the laser system for delivery of multiple spots, preferably adjacent, of laser energy to the treatment site in parallel or in rapid sequence. As there is essentially no residual energy in the tissue after ejection, the multiple spots are treated essentially independently. Multiple spots can be used to achieve very high tissue removal rates with no apparent residual injury to the tissue adjacent the cavity left by the ejected tissue.

It is recognized that different tissue types may require different parameters to achieve flash vaporization and eject substantially all of the material within the interaction volume. Thus, a more generic class of laser systems as described herein can be characterized by including a laser to generate a pulsed beam of light energy, each pulse of the beam to irradiate a volume of tissue and having a duration and an amount of energy to inhibit mechanical energy, or stress, and thermal energy propagation from the volume such that the volume of the tissue is ejected with spinodal decomposition; and a controller coupled to the laser to generate the pulsed light beam in response to commands from the controller that set the laser parameters for tissue-type selective ablation. The system can be combined with an endoscopic delivery tool, including one or more optical fibers. Laser surgery based on flash vaporization can be performed within a complex parameter space described in more detail below. The discovery of commercially feasible operating conditions for lasers and delivery tools as described herein enables for the first time, a new variety of "cold ablation" surgical techniques.

Flash Vaporization as described herein can use pulsed laser energy to efficiently ablate tissue such that the incident laser energy absorbed by tissue is substantially converted from thermal to kinetic energy that is ejected from the treatment site to remove tissue. As a majority of the energy deposited with each pulse can be translated into kinetic energy confined within the tissue volume, any thermal or mechanical energy imparted into the adjacent tissue is substantially decreased, and in some instances essentially eliminated.

The lower overall power requirements provide an advantage in the size and power consumption of the laser itself. A non-limiting example of laser energy characteristics as delivered to tissue to achieve Flash Vaporization, ablation with negligible thermal or mechanical injury to the adjacent tissue, include energy per pulse, pulse width, target volume, target shape, wavelength and repetition rate.

A means to deliver the laser energy to the treatment site can include silica waveguides, doped silica waveguides, non silica based solid core waveguides, hollow core waveguides and free space beam delivery, including articulating arms. Laser based cutting tools can be used with many surgical approaches, including endoscopic surgery. For many surgical procedures, including endoscopic surgery, it is desirable to deliver the laser energy through a low cost, biocompatible, small and flexible waveguide, such as a silica optical fiber waveguide, having an energy transmission efficiency of at least about 80%.

Flash Vaporization can be used for surgical applications. Flash Vaporization provides surgeons the ability to cut tissue, even in endoscopic applications, for example, without substantial thermal or mechanical residual effects to the adjacent tissue. The cutting tip can be very small, submillimeter, and flexible. The laser based flash vaporization cutting tool can be easily positioned and maneuvered at a surgical treatment site. Additionally flash vaporization may not apply mechanical pressure, such as a scalpel would, on the tissue to create a cut. Flash vaporization is well suited for surgical applications where thermal or mechanical injury to the adjacent tissue is undesirable. For example, removal of diseased tissue that has grown around a nerve bundle is an advantageous application of flash vaporization. Precisely controlling the location of the cut along with negligible thermal or mechanical injury to the nerve bundle itself is useful in this application. Pulse-by-pulse operation with microscopic imaging allows for very precise cutting. Flash vaporization can provide surgeons with capability to safely remove tissue with high precision and without impacting the surrounding tissue. Surgeons can achieve better outcomes, efficiently, and with less risk to the patient. However, precise control of the location of the cut can be difficult in some settings. In this case, tissue-type selective operation of the system as described herein can be used to prevent destruction of tissue of one type, such as a nerve bundle, while ablating tissue of another type surrounding the nerve bundle.

Flash vaporization, including tissue-type selective flash vaporization, may be combined simultaneously or serially with other thermal based treatment modalities so as to provide heat induced hemostatic capability surrounding the cut, for certain surgical applications when hemostasis is desirable.

The flash vaporization ablation mechanism can ablate tissue with negligible thermal effects adjacent to the ejected tissue. Flash vaporization can achieve cutting rates with negligible residual damage to the adjacent tissue. Flash vaporization can cut tissue with fast cutting rates. Flash vaporization can be achieved with wavelengths of light energy delivered through standard silica fibers, for example. Clinically, a flash vaporization based laser system offers very fast cutting rates when delivered through a commercially available optical fiber waveguide. Flash vaporization may comprise a high efficiency rate so as to cut tissue with a low average power laser generator which allows the system to be sized to fit in a physician's office with portability and reliability. Flash vaporization based resection systems allow surgeons to readily access many surgical sites of the patient, for example endoscopically, and can cut many types of tissue while preserving adjacent tissue to produce better surgical outcomes with less risk and a faster recovery period for patients.

Flash vaporization can include the incident laser energy being absorbed by a chromophore in the target tissue. Non-limiting examples of typical chromophores for laser energy interaction with tissue may include water, blood, collagen and melanin. It can be desirable to select a chromophore that is present in a wide range of tissue types with sufficient quantity to be effectively targeted. Water is the target chromophore for many embodiments.

The rapid cutting rates achieved with flash tissue vaporization can be achieved with a deep optical penetration depth OPD. Many embodiments use OPDs of at least 70 um to achieve significantly faster cutting rates.

Spinodal decomposition may comprise a phase change of water from liquid to gas that may occur substantially uniformly within a target volume by elevating the water temperature within the volume to approximately 300° C. or greater, for example, within a time frame sufficient to initiate spinodal decomposition. The water in the volume can undergo a spatially and temporally uniform phase change, resulting in pressure-induced kinetic energy such that the tissue can be ejected with inhibited damage to tissue adjacent to the target volume after each pulse. The energy released as a result of the uniform phase change can create stresses that are used to eject the volume.

Flash vaporization can occur with a laser beam pulse by elevating a target volume to a temperature at or in excess of the spinodal threshold for water, in which the target volume can be determined by the incident energy laser beam spot size and the OPD. Also, the spinodal decomposition temperature threshold can be met or exceeded within a time frame that substantially inhibits stress waves from propagating beyond the target volume, such that the ablation is substantially stress-confined to the target volume. The stress confinement conditions can be determined by the propagation speed of the stress waves and the geometry of the target volume. The resulting temporally and spatially uniform phase transition that occurs via spinodal decomposition within a substantial majority of the target volume creates a substantially confined recoil stress so as to efficiently eject the volume, for example, without depositing substantial energy into the tissue adjacent to the target volume after the pulse.

Additional conditions that can be related to weakening the structural integrity of the target volume by liquefaction, for example liquefaction of collagen, optimized volume geometries, and incident energy parameters, ensure a highly efficient removal process with substantially no effect on the surrounding region.

Silica based fiber optic waveguides are suitable for transmitting wavelengths with strong water absorption characteristics for flash tissue vaporization as described herein. Wavelengths greater than about 2.3 um can exhibit strong bulk absorption in silica based fibers and wavelengths greater than 2.5 um can be impractical to use with silica based fiber for ablation processes as described herein.

Many embodiments use light energy having wavelengths within a range from about 1.4 um to about 1.52 um and from about 1.86 um to about 2.5 um, and 2.5 microns may comprise a silica fiber limit. The wavelengths of these embodiments are strongly absorbed by water, are transmissible for use through a silica based optical fiber waveguide and provide an interaction depth of between approximately 70 um and approximately 700 um, for example.

FIG. 1A shows the absorption characteristics of water and corresponding OPD across a broad range of wavelengths. The preferred wavelength ranges of 1.4 um to 1.52 um and 1.86 um to 2.5 um correspond to an OPD≤700 um. Additional embodiments include interaction depths between 70 um and 300 um. Preferred systems have a penetration depth greater than about 50 um, to support interaction volumes and geometries sufficient for flash vaporization at reasonable rates.

Figure 1B:
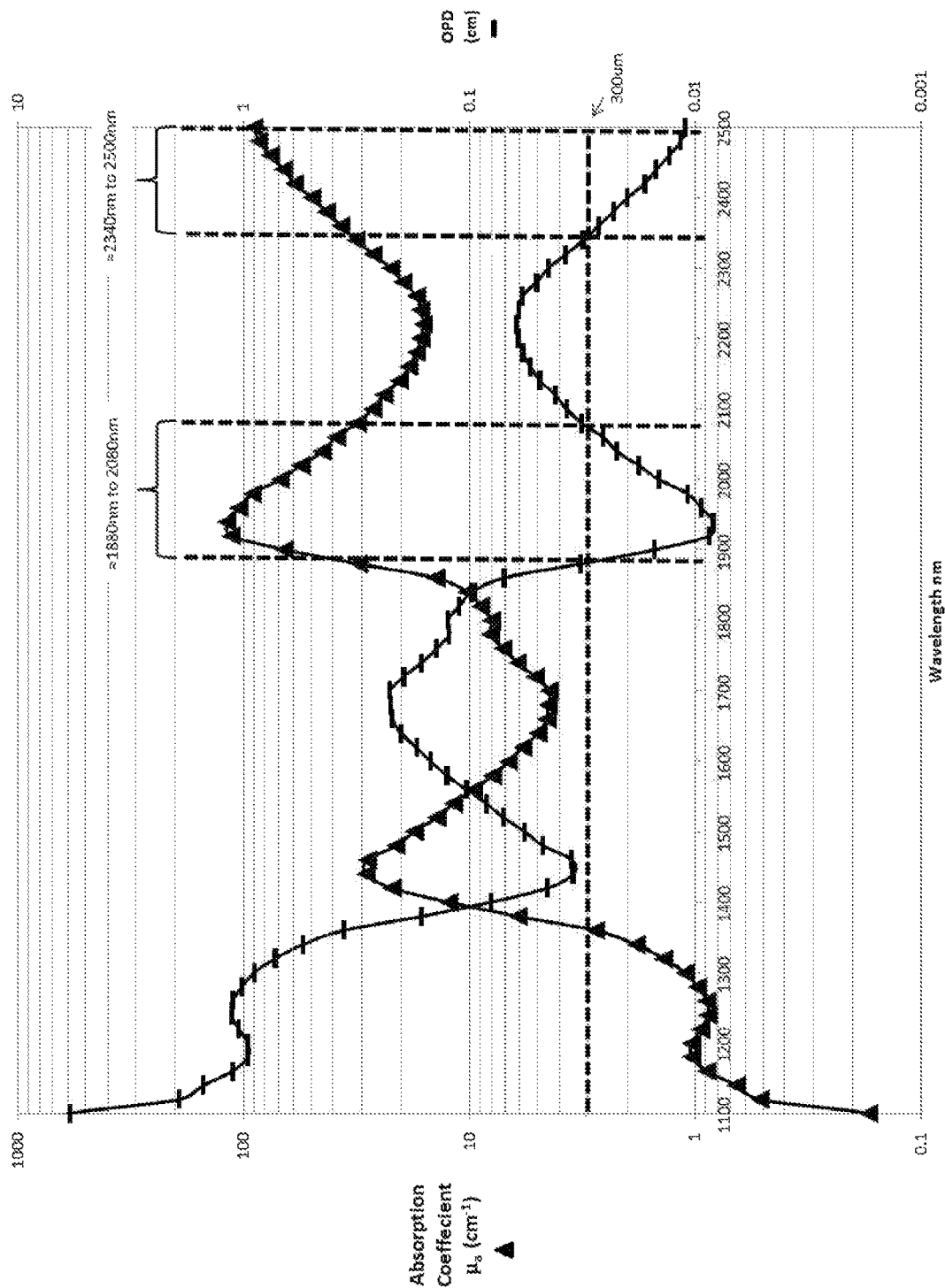

FIG. 1B shows the absorption characteristics of water and corresponding OPD across a broad range of wavelengths. Wavelength ranges with OPD between 70 um and 300 um are from about 1.88 um to about 2.08 um and from about 2.34 um to about 2.5 um. As tissue may comprise substantial amounts of water, the water penetration depth can be used to determine tissue penetration and corresponding tissue ejection volume. A person of ordinary skill in the art can conduct experiments to determine tissue penetration depths based on the teachings described herein. Non-limiting exemplary wavelengths are 1.92 um, 1.94 um, 1.99 um and 2.01 um. Additional embodiments utilize a wavelength of approximately 1.94 um. The laser beams of embodiments with a wavelength of approximately 1.94 um are strongly absorbed in water, are transmissible through a silica based fiber, and provide an interaction depth in the range of 80 um.

Flash vaporization can include delivering laser energy to tissue such that a substantial majority of the target volume of tissue reaches a temperature of approximately 300° C. or higher. By elevating the target tissue volume to at least 300° C., for example, the liquefaction threshold of collagen can be reached as well as the threshold for spinodal decomposition of the target water chromophore. Various forms of collagen are present is many target tissues. By elevating the temperature to the liquefaction threshold the structural integrity of the collagen can be at least significantly weakened. The weakened collagen structure reduces the energy used to eject the material, thereby significantly enhancing the efficiency of tissue removal. By raising the preferred target chromophore, for example water ($H_2O$), within the tissue volume at least to its spinodal limit about 300° C., a relatively uniform phase change can occur within a substantial majority of the target volume. The spinodal phase change is distinctly different from nucleation and bubble growth mechanisms. At the spinodal threshold limit water becomes mechanically unstable and an ensuing rapid phase change to vapor occurs with relative uniformity in the tissue volume creating significant kinetic energy within the target volume.

A further aspect of flash tissue vaporization can include, for example, achieving at least an approximate temperature within the target volume of 300° C. in a time sufficiently short such that the tissue adjacent to the target volume has insufficient time to react substantially. Thus, a substantial majority of the energy is deposited in the target tissue volume before any substantial absorption induced stress propagates from, and before substantial heat diffuses away from, the target volume such that the stress propagation and heat diffusion are inhibited substantially. This inhibition of the dissipation of stress propagation energy and the inhibition of diffusion of heat energy can inhibit damage to tissue adjacent to the target volume after the target volume is ejected.

The parametric constraints that can be used to describe laser beam parameters for the flash tissue vaporization are described by the following equations, which establish a very complex parameter space.

$$\tau_p \leq \frac{1}{\mu_a v_s} \quad \text{Equation 1}$$

where $\tau_p$ is the pulse width (sec), $\mu_a$=absorption coefficient ($cm^{-1}$) or 1/fiber radius (cm) whichever is shortest, $v_s$=velocity of sound (cm/sec)

Equation 1 corresponds to a condition where the pulse duration is sufficiently short to prevent stress waves from propagating beyond the target volume relative to the shortest dimension of the target volume. For the purposes of flash vaporization, substantial stress confinement, enabling tissue ablation via spinodal decomposition with negligible adjacent tissue damage, may be achieved with pulse durations up to approximately 3 times the pulse duration indicated by equation 1.

$$\tau_p \leq \frac{1}{\mu_a^2 k} \quad \text{Equation 2}$$

where $\tau_p$ is the pulse width (sec), $\mu_a$=absorption coefficient ($cm^{-1}$), $\kappa$ is thermal diffusivity ($cm^2$/sec)

Equation 2 corresponds to a condition where the pulse duration is sufficiently short to prevent heat from propagating beyond the target volume.

$$1 \geq \frac{\kappa \tau_p}{\delta^2} \quad \text{Equation 3}$$

where $\tau_p$ is the pulse width (sec), $\kappa$ is thermal diffusivity ($cm^2$/sec), $\delta$ is the chromophore size ($cm^2$). For pure $H_2O$, eq3 is equivalent to eq2 as $\delta = 1/\mu_a$ Equation 3 corresponds to a condition where the pulse duration is sufficiently short to prevent thermal propagation beyond the target chromophore, where for example, the target chromophore represents small volumes of interstitial water dispersed within the collagen mesh work of the target tissue.

Equations 1-3 identify the upper limit of pulse durations related to the tissue laser interaction, suitable for flash tissue vaporization.

The temperature attained as a result of a laser pulse in tissue can be calculated from the following equation for pulses shorter than 1 μsec.

$$T = \frac{\mu_a \phi}{C_v \rho} e^{-\mu_a z} \quad \text{Equation 4}$$

where T=temperature (° C.),
Φ=Energy (J/cm²),
$C_v$=Where $C_v$ is the isochoric specific heat (saturated liquid heat capacity at constant volume) of the chromophore ($H_2O$) (J/g° C.),
ρ=density (g/cm³)
and z=depth (cm)

Equation 4 indicates the required fluence to achieve a desired temperature at a depth in the target volume.

$$\phi = \frac{C_v T \rho}{\mu_a} \quad \text{Equation 5}$$

where T=temperature (° C.),
Φ=Energy (J/cm²),
$C_v$=specific heat (J/g° C.),
ρ=density (g/cm³)

Equation 5 indicates the appropriate fluence to reach the threshold temperature for spinodal decomposition of the target chromophore ($H_2O$).

Equations 1-5 may be used to determine, for a given wavelength and target tissue, the fluence required to reach 300° C. with substantially the entire target volume and to determine the maximum pulse duration suitable for flash vaporization. For flash tissue vaporization the lower pulse duration limit can, in part, be determined to prevent substantial plasma generation and to prevent damage to a waveguide delivering the pulse, like a silica based optical fiber.

Volumetric power density (VPD) can be re-cast to Equation 6;

$$VPD = \frac{\mu_a E}{A_r t_p} = \frac{\mu_a E}{\pi \omega^2 t_p} \quad \text{Equation 6}$$

where:
E=energy (J),
$\mu_a$=absorption coefficient (cm⁻¹),
$A_r$=area (cm²),
$t_p$=pulse width (sec) and
ω=radius of incident spot (cm)

Spinodal decomposition has a minimum VPD to substantially eliminate energy loss due to bubble formation and/or cavitation. Experimentation suggests a VPD of roughly $10^{10}$ W/cm³ or higher is sufficient to induce spinodal decomposition, in some instances typically with pulse durations 200 ns. For stress confinement, shorter pulse lengths can be required.

Flash Vaporization may include a pulse width short enough for a given target tissue volume to inhibit substantial thermal or mechanical energy within the interaction volume from propagating into the adjacent volume during the deposition of the light energy into the target tissue. It may be advantageous for the pulse width to be long enough for a given peak irradiance and target tissue to substantially inhibit plasma formation. Propagation of thermal energy, mechanical energy and substantial plasma formation may each introduce tissue removal inefficiencies that can lead to damage of the adjacent tissue. Pulse widths in the range of about 100 ps to 1 us may be suitable for flash tissue vaporization. For example, pulse widths between 0.5 ns and 100 ns can be preferable for wavelengths targeting water as a chromophore.

The parameters of Flash Vaporization are related to the size of the targeted tissue interaction volume. Larger interaction volumes may require more laser energy to reach the spinodal and liquefaction limits while satisfying the above conditions so as to substantially prevent thermal and/or kinetic energy from propagating into the tissue adjacent to the ablation site. As the above described pulse energy increases, the pulse duration may also increase in order to inhibit exceeding peak power damage thresholds of the laser generator and/or the delivery system. The interaction volume range can be determined based on the largest volume where flash vaporization can be achieved with a practical and commercially viable laser and delivery system. For example using a 1.94 um wavelength and targeting porcine kidney with approximately 70% water content with a 100 um core silica fiber in contact mode yields an interaction volume of approximately $9 \times 10^{-7}$ cm³. An interaction volume size in the range of $10^{-8}$ cm³ to $10^{-4}$ cm³ can be used in many embodiments. Many embodiments can use an interaction volume of $10^{-7}$ cm³ to $10^{-5}$ cm³.

Flash vaporization can be related to the shape of the interaction volume. The ratio of the interaction volume depth to the interaction volume width may correspond to the efficiency in which the tissue is removed including the ability to extract a substantial majority of the absorbed laser energy with the ejected volume. The ejection of target tissue from the treatment site may comprise a mechanical process. Kinetic energy created by spinodal decomposition within the interaction volume can drive the tissue material removal process. Optimizing the shape of the interaction volume can improve the efficiency of tissue removal. Interaction volume shapes where the depth is substantially larger than the width may provide less efficient ejection of the target tissue, which can lead to residual mechanical or thermal effects on tissue adjacent to the target volume. Additionally, interaction volumes where the depth is substantially less than the width may lead to inefficient target tissue removal which may cause residual mechanical or thermal effects on the adjacent tissue. Depth and width ratios are related to the OPD of the wavelength used for a given target material and the incident spot size delivered to the tissue surface.

Figure 2A:
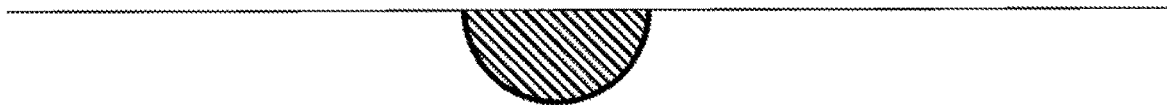
FIGS. 2A, 2B, 2C show a representative interaction volume depth-to-width ratio, in accordance with embodiments.
Figure 2B:
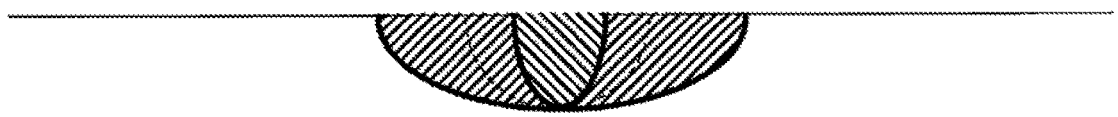
Figure 2C:

FIG. 2 shows a representative interaction volume depth-to-width ratio for several embodiments. One embodiment is a depth-to-width ratio of approximately 1:2, see FIG. 2a. This can be a preferred species because the efficiency of tissue ejection can be high, and the energy per pulse needed to achieve tissue removal can be well within operating conditions of a fiber optic delivery tool. Another embodiment is a depth-to-idth ratio in a range between 1:4 to 2:1, see FIG. 2b. This range encompasses larger areas on the tissue surface, and requires larger energy per pulse for the larger areas. These larger energy per pulse requirements can be more difficult to achieve with a given laser system. Another embodiment is a depth-to-width ratio in a range between 1:6 to 2:1, see FIG. 2c. This more generic range of geometries includes even larger surface areas, requiring even larger energies per pulse.

The targeted tissue interaction volume size and/or shape can determine the pulse energy to achieve Flash Vaporization. Too little energy per pulse may not drive the target chromophore to the spinodal limit and/or may not provide sufficient kinetic energy to eject the material within the interaction volume. Too much energy per pulse may not be practical to generate or deliver and can introduce inefficiencies in the tissue removal process. In both cases, with too little and too much per pulse energy, residual mechanical and/or thermal effects on the adjacent tissue may occur. The threshold energy to achieve spinodal decomposition can be calculated from equations 1-5.

The efficiency can be determined per equation 7.

$$\eta = \frac{A\rho}{\mu_a E_i} \ln\left(\frac{E_i}{E_{th}}\right) \quad \text{Equation 7}$$

where $\eta$=efficiency (gm/J),
$\mu_a$=absorption coefficient (cm$^{-1}$),
A=spot size (cm$^2$),
$\rho$=density (gm),
$E_i$=input energy (J) and
$E_{th}$=threshold energy for spinodal decomposition at the surface (J)
And for optimum efficiency $$E_i = E_{th} e \text{ yields } E_{opt}$$

e is Euler's number=2.71828 (to five significant figures).

The ideal energy is related to the energy required to achieve spinodal decomposition plus the additional energy to eject the target volume with optimal efficiency. Energy exceeding $E_{opt}$ is imparted to the ejected material, in this case water. Now as the target volume is not entirely water and can contain significant amounts of collagen in different organizational structures, the energy exceeding $E_{opt}$—may be used to overcome the tensile strength of the tissue within the volume.

The energy used for flash vaporization of one soft tissue type can be different than the energy needed to accomplish flash vaporization of a different soft tissue type. Also, the energy sufficient for flash vaporization of one soft tissue type is insufficient to cause substantial damage to some other soft tissue types. As a result, boundaries between soft tissue types can be relied upon for self-alignment of tissue removal, causing ablation of soft tissue type A and stopping the ablation at the boundary with soft tissue type B.

Many embodiments for flash vaporization include pulse energies within the range from about 100 uJ to about 100 mJ. Furthermore many embodiments for flash tissue vaporization using water as the chromophore utilize pulse energies from 500 uJ to 30 mJ. Specific embodiments for Flash Vaporization can use water as the chromophore and a wavelength near 1.94 µm and pulse energies from 1 mJ to 10 mJ.

The flash tissue vaporization process, in some instances, has threshold fluences in the range of joules per centimeter squared.

Figure 3:
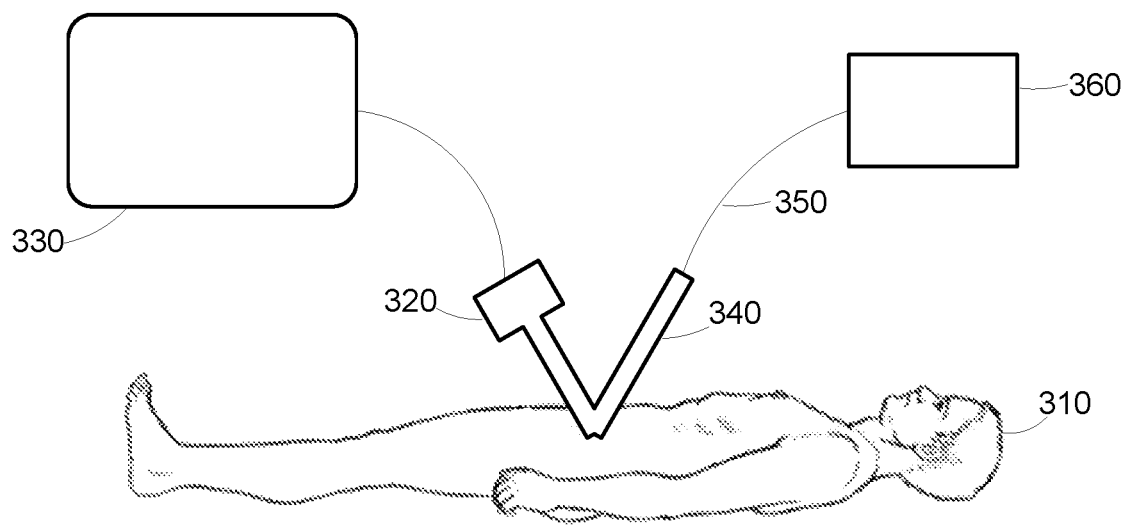
FIG. 3 shows a laser system utilizing Flash Vaporization for tissue removal during laparoscopic surgery, in accordance with embodiments.

FIG. 3 shows a laser system utilizing Flash Vaporization for tissue removal during laparoscopic surgery. The patient 310 has an imaging system 320 inserted in the thoracic cavity. The imaging system 320 may be a direct viewing type or it may have a camera with a video display 330 such that the surgeon can view the inside of the thoracic cavity. An insertion device 340, such as an endoscope, with a delivery system 350 is also inserted into the thoracic cavity. The proximal end of the delivery system 350 is attached to a laser system 360.

Figure 4:
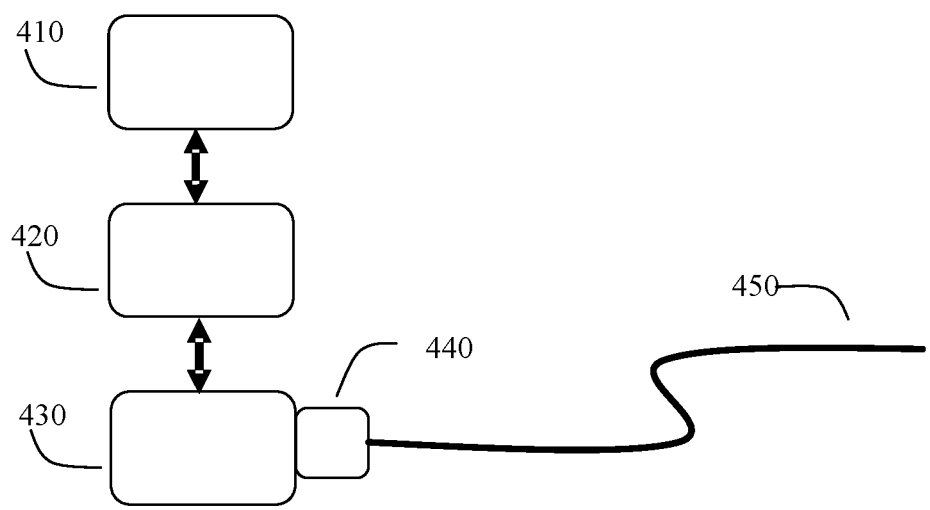
FIG. 4 shows a laser system for implementing a Flash Vaporization based surgical device, in accordance with embodiments.

FIG. 4 shows the laser system of FIG. 3 for implementing a Flash Vaporization based surgical device. The laser system has a user interface 410 to adjust system parameters and to control the laser energy emission. The user interface 410 is in communication with the controller 420. The controller operates the laser resonator 430 to provide the appropriate output selected via the user interface 410. The output of laser energy from the resonator 430 is directed to a device coupler 440. The device coupler 440 directs the laser energy into a delivery system 450. A representative delivery system 450 comprises a 100 um core silica fiber used in contact, or near contact, with the target tissue. A representative non-contact delivery system 450 comprises a silica core fiber with a focusing element to generate a 100 um treatment spot about 2 cm from the tip of the silica fiber. In other embodiments, fiber tip optical components can be utilized for spot shaping and beam pointing.

Figure 5:
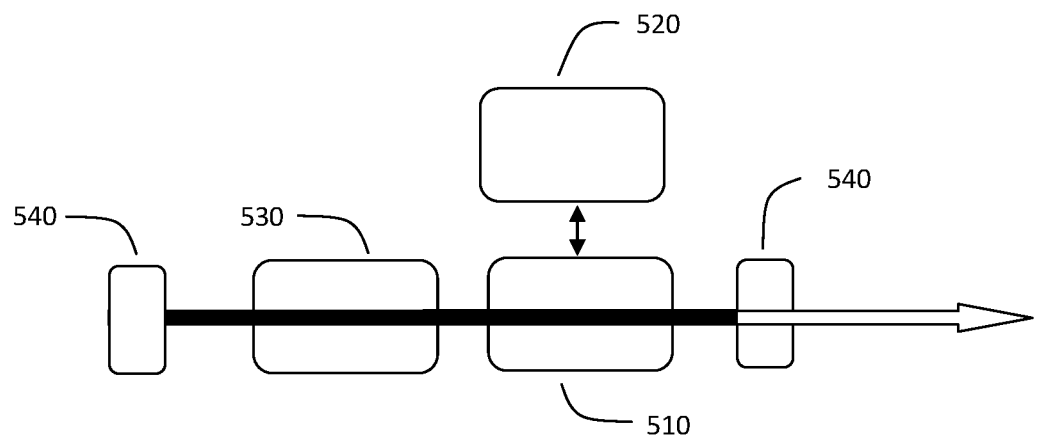
FIG. 5 shows a laser resonator for implementing Flash Vaporization, in accordance with embodiments.

FIG. 5 shows components of the laser resonator 430 for implementing flash tissue vaporization, having a gain medium 510, pump source 520, modulator 530 and at least two mirrors 540. Non-limiting examples of the gain medium 510 include solid state, gas, liquid, semiconductor based, or waveguide based gain mediums. The gain medium 510 may be selected to provide a specific wavelength or wavelength range that is desirable for interaction with the target tissue. Non-limiting examples of solid state gain medium 510 for the preferred wavelength range of 1.8 um to 2.5 um are Ho:YAG, Tm:YAG, Tm:YAP, Tm:GaVO4 and Tm:YLF. A solid state gain medium is an embodiment due to the ability to generate laser energy with highly efficient pumping processes within wavelength ranges that may target chromophore present in a wide variety of tissue. Solid state gain mediums also enable small and low cost implementation. The lower cost and size of solid state lasers is appealing to the surgeons and facilities using the equipment. Non-limiting examples of the pump source 520 include a laser diode, arc lamp, flash lamp or electrical stimulation. A laser diode is a preferred pump source 520 offering low maintenance requirements and an efficient means to pump the gain medium 510. Furthermore an end pumping configuration may be employed to improve the efficiency of the pumping process. A modulator 530 may be used to provide pulsed laser energy and may be implemented intracavity or externally. Non-limiting examples of modulators 530 include acousto-optic, electro optic, saturable absorbers or mechanical means. An embodiment may be an intracavity acousto-optic or electro-optic modulator. The electro-optic modulator may have further advantages when the laser resonator 430 produces polarized energy. The laser resonator 430 preferably has two mirrors 540. One mirror reflects approximately all of the laser energy while the second mirror partially reflects the laser energy serving as an output coupler to extract laser energy from the laser resonator. A two mirror resonator often reduces the laser resonator complexity and reduces the overall cost of the laser system. Additional laser resonator configurations with more than two mirrors may also be used. Optimizing the efficiency and simplicity of the laser resonator 430 is a factor in the commercial viability of a laser based surgical tool. A representative laser resonator configured for flash vaporization includes a gain medium 510 comprising Tm:YAP configured to lase efficiently at 1.94 um with a pump source 520 comprising a fiber coupled laser diode configured for end pumping the gain medium 510. The representative laser resonator further includes a modulator 530 comprising an acousto-optic Q-switch and two mirrors 540, one substantially reflecting all the light at 1.94 um and the second partially reflecting light at 1.94 um to function as an output coupler.

Thus, one species of a more generic class of laser systems capable of use for flash vaporization as described herein includes a Tm:YAP gain medium 510 arranged to produce an output wavelength near 1940 nm, operating with an energy per pulse in the range of 1 to 10 mJ per pulse in pulse widths less than 100 nsec, with a beam delivery tool 350,

340, such as an endoscope with a fiber optic or other waveguide, arranged to deliver a spot size of 50 to 200 microns to a target tissue. A wavelength near 1940 nm has an optical penetration depth in water of about 80 microns. Because water is a primary component of most tissues, the penetration depth in tissue can be approximately the same. Using a spot size and an 80 micron penetration depth, one can determine the dimensions of an interaction volume within the tissue at the treatment site for a laser pulse. Using a pulse width less than 100 nsec, such as between 10 nsec and 50 nsec for a representative procedure, results in a condition of thermal and mechanical confinement of the energy dissipation from the laser pulse, within that interaction volume. Using an energy per pulse on the order of 0.5 to 40 mJ is sufficient in this example to generate greater than $10^{10}$ W/cm$^3$ within the interaction volume and raise the temperature of the water in the interaction volume above the spinodal limit, which can cause confined spinodal decomposition of the water. The spinodal decomposition results in an instantaneous phase change that creates substantial pressure in a range of about 200 bars to 10 kBars within the interaction volume at the treatment site. Energy in the pulse is translated via spinodal decomposition into kinetic energy that can eject the tissue without visible thermal damage to tissue adjacent to the ejected volume caused by thermal or acoustic waves induced by the ejection or the laser pulse. This effect is termed herein Flash Vaporization. The laser system according to this species can be operated with repetition rates from single shot to 2000 Hz, and because of the substantial volume of tissue ejected with each pulse, cutting rates using Flash Vaporization that have not been possible using known prior art techniques can be achieved.

Other species of laser systems within this more generic class includes lasers 430 operating in wavelengths that have similar optical penetration depths in tissue having water as a primary component, including wavelengths between 1400 and 1520 nm or between 1860 and 2500 nm. Wavelengths in this range are also characterized by the fact that they are readily deliverable using silica waveguides on the order of 50 to 200 microns in core diameter within the energy per pulse in the range of 0.5 to 40 mJ per pulse and pulse widths between about 10 nsec and 200 nsec. A controller 420 and a visualization monitor (user interface) 410 can be utilized for control of laser parameters and surgical procedures. In some embodiments, the controller 420 can be operated to control energy per pulse within a range from about 100 uJ to about 100 mJ. Furthermore, many embodiments for flash tissue vaporization using water as the chromophore utilize pulse energies from 500 uJ to 40 mJ. Specific embodiments for Flash Vaporization can use water as the chromophore and a wavelength near 1.94 µm and pulse energies from 1 mJ to 10 mJ. Because of the availability and biocompatibility of silica waveguides, these species of laser systems can be readily utilized in a wide variety of endoscopic laser surgeries.

It is recognized that different tissue types require different parameters to achieve flash vaporization and eject substantially all of the material within the interaction volume. Thus, a more generic class of laser systems as described herein can be characterized by including a laser to generate a pulsed beam of light energy, each pulse of the beam to irradiate a volume of tissue and having a duration and an amount of energy to inhibit mechanical energy, or stress, and thermal energy propagation from the volume such that the volume of the tissue is ejected with spinodal decomposition; and a controller coupled to the laser to generate the pulsed light beam in response to commands from the controller. The system can be combined with an endoscopic delivery tool, including one or more optical fibers. Laser surgery based on flash vaporization can be performed within a complex parameter space described in more detail below. The discovery of commercially feasible operating conditions for lasers and delivery tools as described herein enables for the first time, a new variety of "cold ablation" surgical techniques.

The spinodal decomposition process generates pressure within the target tissue volume. The pressure is generated, in part, when the chromophore, for example water, in the target volume reaches or exceeds the spinodal threshold, thus initiating spinodal decomposition, on a time scale sufficient to substantially prevent propagation of thermal or mechanical energy beyond the target volume. The pressure generated ejects material from the target site. The amount of pressure to adequately or optimally eject substantially all of the target volume is, in part, dependent upon the mechanical properties of the tissue itself. Various tissue types have different mechanical properties, in part, due to the collagen structure of each tissue type. A comparison of skin to kidney is one example. Skin has a higher tensile strength than kidney. The higher tensile strength of skin is, in part, due to its function, and the environment to which it is exposed. Additionally, skin typically has a lower water content than kidney tissue, resulting in a variation of the effective $\mu_a$ as compared to kidney when water is used as the chromophore. The difference in the effective $\mu_a$ and tensile strength may result in different pulse parameters within the flash vaporization regime to remove the two tissue types. The variation in pulse parameters, in part, reflects the different pressures needed to overcome the tensile strength of each tissue type to eject substantially the entire volume of tissue, including the threshold pressure and the optimal pressure range. Bone is another example where different pressures may be required to eject substantially all of the tissue in the target volume. Bone typically has a lower water content than soft tissue, which may affect the effective $\mu_a$ when water is the chromophore. The relevant mechanical properties of bone may be related to the force required to fracture bone within the target volume rather than pure tensile strength. The parameters for flash vaporization and the resulting pressure generated may be different for bone when compared to soft tissue.

The localized temperatures generated in the target volume during a flash vaporization event are near or exceed the liquefaction threshold for collagen. At or above the liquefaction threshold for collagen the structural integrity of the tissue may be compromised, weakening the collagen structure. The weakened structures still exhibit variation in mechanical properties for different tissue types. Efficient removal of specific tissue types can be achieved, in part, by generating pressure in the target volume that is sufficient and/or optimal for tissue ejection. Achieving flash vaporization with the ability to generate a range of pressures may be a factor in effectively targeting a wide variety of tissue types.

Equation 4 can be recast by substituting $E/A_r$ for $\varphi$, yielding equation 8, for pulses shorter than 1 usec.

$$T = \frac{\mu_a E e^{-\mu_a z}}{C_v \rho A_r} \qquad \text{Equation 8}$$

where:
T=temperature (° C.),
E=energy (J),
$A_r$=area (cm$^2$)
Cv=Where Cv is the isochoric specific heat (saturated liquid heat capacity at constant volume) of the chromophore (H$_2$O) (J/g° C.),
ρ=density (g/cm$^3$) and
z=depth (cm)
$\mu_a$=absorption coefficient (cm$^{-1}$), The pressure generated in the target site can be calculated from equation 9 for pulses shorter than 1 μsec.

$$P = A\mu_a \Gamma \varphi e^{-\mu_a z} \text{ where:} \qquad \text{Equation 9:}$$

P=Pressure, $$A = \frac{1-e^{-\tau}}{\tau},$$

$$\tau = \frac{t_p}{t_o},$$

$t_p$=pulse width, $$t_o = \text{characteristic pulse width} = \frac{1}{\mu_a v_s}$$

$v_s$=sound velocity (cm·sec$^{-1}$)
Γ=Grüneisen parameter (dimensionless),
φ=Fluence
$\mu_a$=absorption coefficient (cm$^{-1}$),
z=depth (cm)

In one embodiment the temperature and/or pressure throughout the interaction volume are considered, specifically the temperature and/or pressure at the optical penetration depth where $$z = \frac{1}{\mu_a}.$$

To achieve the spinodal decomposition threshold temperature at the optical penetration depth, $$z = \frac{1}{\mu_a},$$

T can be recast as Equation 10, $$T = Te, \text{ where:} \qquad \text{Equation 10}$$

T=temperature
e is Euler's number=2.71828

Now the temperature within the full optical penetration depth for each pulse can be determined to meet or exceed the spinodal decomposition threshold thus, in part, initiating flash vaporization throughout the interaction volume.

Similarly to achieve, at least, the threshold pressure at the optical penetration depth, $$z = \frac{1}{\mu_a},$$

needed to eject a given target tissue, P can be recast as Equation 11, $$P = Pe, \text{ where:} \qquad \text{Equation 11.}$$

P=pressure
e is Euler's number=2.71828

Now, the pressure within the full optical penetration depth for each pulse can be determined to meet or exceed the pressure threshold needed to eject substantially all the tissue throughout the interaction volume.

Equation 10, in part, determines the lower temperature limit for flash vaporization in H$_2$O throughout, substantially, the entire interaction volume. However the pressure generated may not be enough to overcome the mechanical strength of the target tissue. It may be necessary to adjust the pulse parameters to achieve threshold or optimal pressure to eject substantially all of the tissue within an interaction volume. Additionally each different target tissue type may have different threshold and/or optimal pressures for ejecting the respective tissues. If we re-cast the pressure equation to include the relevant parameters we can see more easily which parameters will have the largest effect.

We have $\tau = \frac{t_p}{t_o}$ & $t_o = \frac{1}{\mu_a v_s}$ thus $\tau = t_p \mu_a v_s$ and $$\varphi = \frac{E}{A_r} \text{ where } A_r = \pi \omega^2$$

So:

$$P = \frac{1 - e^{-(t_p \mu_a v_s)}}{t_p v_s} \cdot \frac{\Gamma E}{\pi \omega^2} \qquad \text{Equation 12}$$

where:
P=pressure
E=energy (J),
$\mu_a$=absorption coefficient (cm$^{-1}$),
$t_p$=pulse width (sec),
ω=radius of incident spot (cm)
$v_s$=sound velocity (cm/sec)
Γ=Grüneisen parameter (dimensionless), We notice immediately that P changes exponentially as:
  the pulse width
  the sound velocity
  the absorption coefficient
inversely with the square of the spot radius ω
linearly with energy The velocity of sound is a property of the target chromophore and cannot be readily changed for a given type of target tissue. The wavelength directly affects the absorption coefficient and may be used independently or in part to achieve a desired pressure. In one embodiment where the wavelength remains constant, any one or combination of pulse duration, energy per pulse and/or spot size may be changed to achieve a desired pressure for ejecting a specific target material. Each parameter indicated in equation 12 may individually or in combination be adjusted to achieve a desired pressure. Within the multivariable parameter space that achieves a desired pressure, generating and/or delivering a pulse with certain parameters may be impractical. For example a certain range of pulse energy and pulse durations may achieve a desired pressure according to equation 12, but no laser source may exist to achieve the particular pulse energy and pulse width combinations.

In tissue selective flash vaporization, pulses of the pulsed laser beam have a wavelength with an associated optical penetration depth D in tissue of the first soft tissue type, an energy per pulse, a fluence φ, a spot area and a pulse duration $t_p$ toward an interaction volume of a target tissue; and including generating pressure within the interaction volume of the target tissue of the first soft tissue type, which causes ejection of the target tissue within the interaction volume and heating the interaction volume above a spinodal decomposition threshold at the optical penetration depth using the laser pulses, wherein the wavelength is between 1400 and 1520 nm or between 1860 and 2500 nm and the energy per pulse between 0.5 milliJoules and 40 milliJoules, wherein the interaction volume is a function of the optical penetration depth D and the spot area of the pulses of the pulsed laser beam incident on the target tissue, where the spot area has a minimum width W, and wherein the optical penetration depth D is a function of an absorption coefficient $\mu_a$ of the target tissue that is determined by tissue properties and the wavelength, and wherein the optical penetration depth and minimum spot width satisfy a condition that D is within a range of ⅙ W to 2 W, the pulse duration $t_p$ meets stress confinement conditions for the interaction volume including:

$t_p < 1/\mu_a v_s$ and
$t_p < W/2v_s$, where $v_s$ speed of sound in the target tissue, and further that the pulse duration t is less than 200 nsec; wherein the energy per pulse of the laser pulses in the heating of the interaction volume heats water within the interaction volume to induce a phase transition by spinodal decomposition within the interaction volume creating said pressure, and the fluence φ, satisfies:

$$\phi = \frac{t_L}{1 - e^{t_L}} \frac{P}{\Gamma \mu_a}$$

for the first soft tissue type but not for an adjacent second soft tissue type, where:
P=pressure to eject the target tissue
$t_L = t_p \mu_a v_s$
Γ=dimensionless strength parameter of the target tissue.

Similarly, the ability, in practice, to deliver a pulse to a target tissue should be considered. For example, even in the absence of a waveguide, certain subsets of parameters within a parameter space achieving, at minimum, flash vaporization and tissue specific pressure thresholds may generate plasma at the tissue or in air which may interfere with the delivery of the pulse to tissue and therefore ultimately may not satisfy the conditions within the tissue volume for flash vaporization and/or pressure to eject the target tissue.

A waveguide, in some instances, may be selected such that a range of pulse parameters can be successfully transmitted through the waveguide and subsequently adjusted, typically by focusing elements, to achieve flash vaporization with a pressure sufficient to eject, substantially, the entire target volume.

For many surgical applications it may be advantageous to use a waveguide where the waveguide core is roughly the same diameter as the treatment spot size. One embodiment where the waveguide core and treatment spot size are similar is when the waveguide is used in contact to or near contact to the target tissue.

Silica fibers are a dominant type of waveguide used to deliver laser energy for endoscopic applications. Silica fibers are readily available, flexible, biocompatible and low cost. Silica fiber waveguides are a preferred embodiment for utilizing flash vaporization for many tissue cutting applications, including endoscopic procedures. The pulse parameters used to achieve flash vaporization and/or pressure sufficient to eject the target material have, in part, high peak power. High peak power can damage silica based waveguides. A preferred embodiment is therefore a range of laser pulse parameters that both achieve flash vaporization with an appropriate pressure to eject the material for a given target and can be reliably transmitted down a silica based fiber without catastrophic damage to the silica fiber. The theoretical bulk damage limit for silica fiber is known across a broad range of pulse durations, including a subset of pulse durations suitable for flash vaporization. In practice the theoretical limits have not been fully achieved. Studies have shown the practical relationship between pulse energy and pulse width follows equation 13

$E_i = a d^b t_{min}^c$ where:                     Equation 13:

Where: a, b and c are coefficients that have been determined experimentally
a=3921.5
b=0.95
c=0.5
$E_i$=energy (J)
$t_{min}$=pulse width (sec)
d=fiber core diameter (cm)

For example, by knowing the target soft tissue type and selecting a wavelength, essentially $\mu_a V_s$, $C_v$, ρ can be determined. Then by substituting equation 13 into the relevant previous equations, a parameter space, if it exists for a given soft tissue type, wavelength and fiber damage threshold, can be determined such that conditions for flash vaporization with sufficient pressure to eject the target material can be met, including delivery with a silica fiber. By knowing the ablation threshold for a second soft tissue type, and selecting the laser parameters to produce a pulsed laser beam that falls between the ablation thresholds of the first and second soft tissue types, tissue selective ablation is accomplished.

Figure 6:
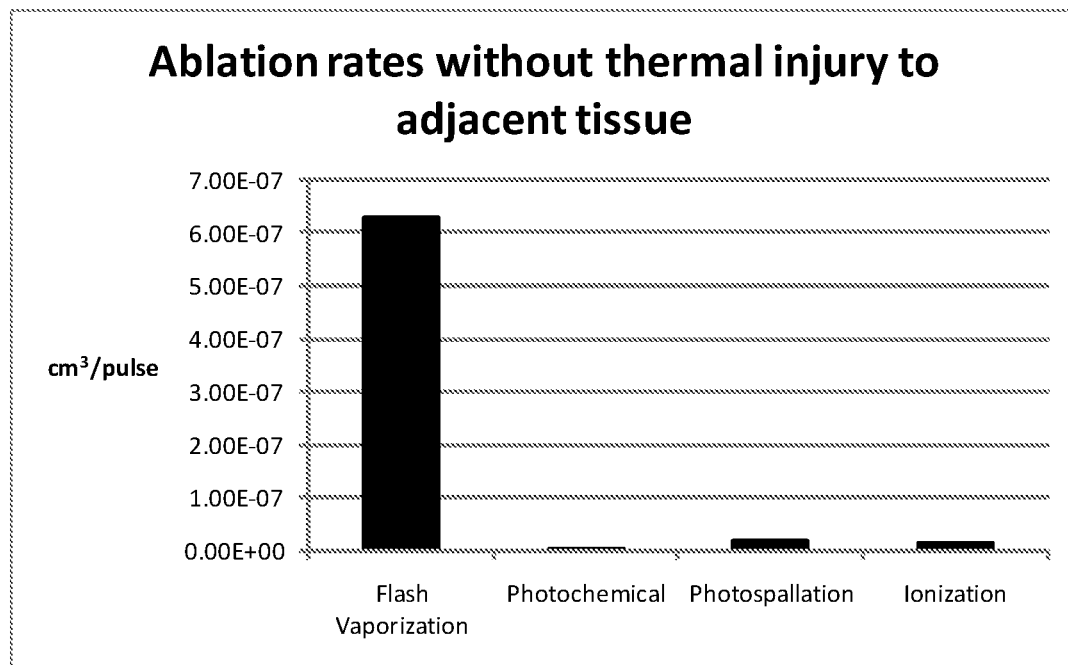
FIG. 6 shows a bar chart comparing cutting rates for various forms of resection, in accordance with embodiments.

Cutting Rate Experiment:

A flash tissue vaporization based laser system operating at a 1.94 um wavelength was built and used to conduct ex-vivo tissue cutting tests. The pulse energy used was approximately 3.5 mJ and was delivered through a silica based fiber optic waveguide, and the pulse repetition rate was 400 Hz. The fiber tip was positioned in a mount and held in a fixed location. The movable test stand with a porcine kidney tissue sample was moved through the beam immediately in front of the fiber tip. The approximate length of the tissue sample was 2 cm with a thickness of approximately 2 mm. The flash vaporization system cut through the entire sample in 8 seconds. The system made a 2.5 mm long by 2 mm deep cut each second. The volume of tissue removed per pulse was $6.28 \times 10^{-7}$ cm³/pulse. This cutting rate is dramatically faster than prior art laser systems. For example, an excimer laser system with similar pulse repetition rates and incident spot size with the fluence optimized to operate in a mode without adjacent thermal injury yields a rate of $3.14 \times 10^{-9}$ cm³/pulse, 200 times slower. Similarly, a photospallation based Erbium YAG system with similar pulse repetition rates and incident spot size with the fluence optimized to operate in a mode without adjacent thermal injury yields a volume removed per pulse of $1.57 \times 10^{-8}$ cm$^3$/pulse, 40 times slower. A high power research oriented femtosecond system with similar pulse repetition rates and incident spot size with the fluence optimized for ablation without adjacent thermal injury yields a rate of $1.49 \times 10^{-8}$ cm$^3$/pulse, over 40 times slower as well. FIG. 6 shows a bar chart comparing cutting rates for various forms of resection without substantially any adjacent tissue injury. The photochemical, photospallation and ionization based systems do not have a suitable means for fiber delivery for typical surgical applications and are typically limited to line-of-sight delivery.

Figure 7A:
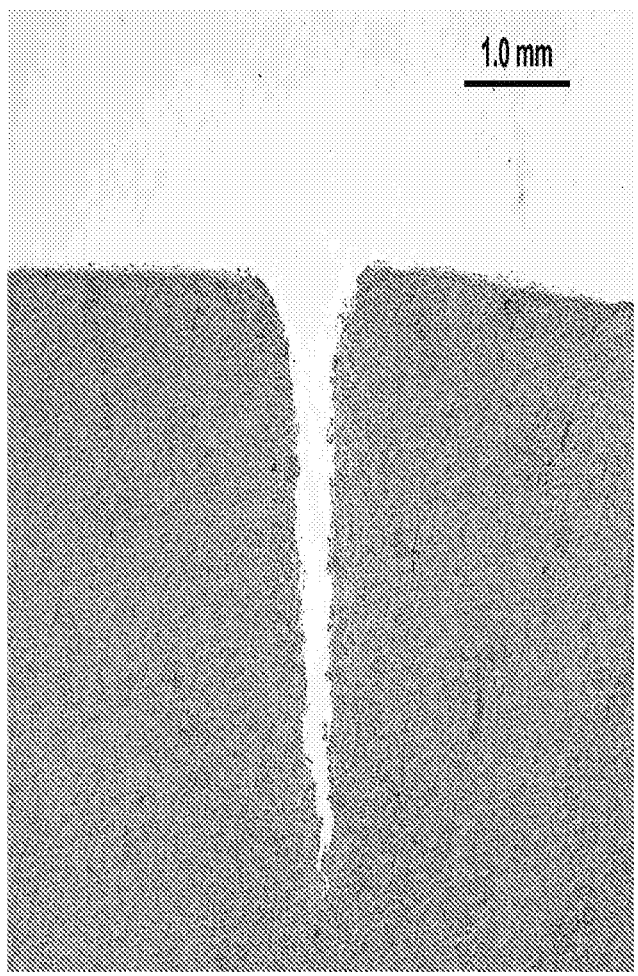
FIGS. 7A and 7B are images showing histology obtained from tissue resection performed with a laser system, in accordance with embodiments as described herein.
Figure 7B:
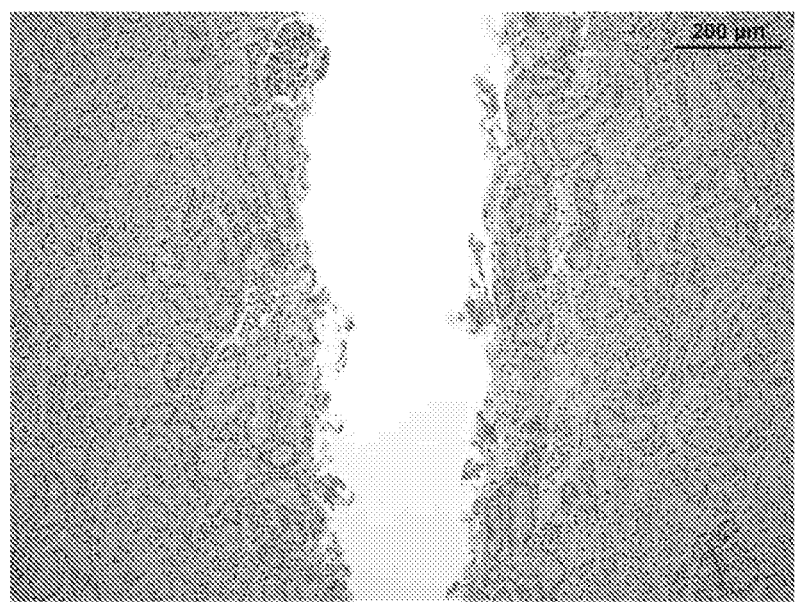

FIG. 7a is an H&E stained histology of a cut made in ex-vivo porcine kidney with the Flash Vaporization system. The cut was approximately 3 mm deep by 5 mm long and took approximately 3 seconds to perform with an average power of approximately 1.4 watts and a depth to width ratio of 1.2:1. The histology shows a clean cut with no apparent thermal injury to the tissue adjacent the cavity left by the ejected tissue. FIG. 7b is a higher magnification image of the same tissue sample. The cut surface shows no apparent thermal injury. Flash Vaporization enables previously unobtainable high speed cutting rates for deeper incisions with no apparent thermal injury to the adjacent tissue. Also, no mechanical injury is seen, except on the microscopic scale that would not materially lengthen healing rates.

For some surgical procedures it may be desirable to remove a large mass of tissue directly via Flash Vaporization rather than by excision. For example a surgical treatment for Benign Prostatic Hyperplasia may involve removal of a large mass of prostate tissue. The removal of prostate tissue can be achieved either via an excision style process or a mass tissue vaporization process, depending on the surgeon's preference. Removal of tissue in the colon is another example where removal directly via Flash Vaporization may be advantageous. Sessile colon tumors are embedded in the inner wall of the colon and may be difficult to remove by excision. The ability to vaporize the tumor in layers, without collateral damage, from the surface down to healthy tissue may be advantageous. Using tissue selective ablation, the layers of different soft tissue types underlying the tumor can be used as an ablation stop, further preventing damage to health tissues.

Referring to equations 7 and 12 and the related equations described herein there is at least one combination of parameters that provides the optimal tissue ablation efficiency, maximum grams of tissue ablated per joule. When operating at the optimal efficiency, the maximum tissue vaporization rate can be achieved. The tensile strength of tissue types varies throughout the body, thus it is evident that the optimal parameters required to remove the target tissue will vary. This is achieved by optimizing the pressure in the target volume. For example the pressure required for optimum vaporization of the dermis is significantly higher than required for kidney.

The maximum speed at which tissue can be vaporized via Flash Vaporization corresponds to the optimal ablation efficiency. Therefore, a problem exists when the surgical procedure requires/desires a rate of ablation that is greater than the rate of ablation corresponding to the peak ablation efficiency. To achieve ablation rates that exceed the maximum ablation rate described above, a novel delivery device with two or more fiber optic waveguides may be used. As spot size increases, the energy per pulse needed to achieve ejection by spinodal decomposition increases significantly. This limits the size of a laser spot than can be practically used in laser surgery applications.

Species of laser systems described herein are configured to remove larger volumes of tissue per unit time. Such species utilize lasers capable of producing outputs that are a multiple of the energy per pulse to be applied by each pulse. In such species, a delivery tool including multiple waveguides can be coupled to the laser system for delivery of multiple spots, preferably adjacent, of laser energy to the treatment site in parallel or in rapid sequence. As there is essentially no residual energy in the tissue after ejection, the multiple spots are treated essentially independently. High repetition rates and multiple spots can be used to achieve very high tissue removal rates.

A laser source may be capable of producing energy/power well beyond the amount required to achieve optimal ablation efficiency. Delivering a laser pulse to tissue with a fluence, for instance, greater than the peak efficiency, reduces the ablation efficiency and in some cases may even exceed the damage limits for a single fiber optic waveguide. By dividing a laser pulse generated within the laser source and coupling the pulse into multiple fibers each individual fiber can simultaneously receive a portion of the pulse energy. Furthermore, by aligning the individual fiber outputs to separate regions of the target tissue, typically adjacent to one another, each fiber can be configured such that the tissue at each fiber's individual treatment site is ablated with optimal ablation efficiency. Utilizing a laser system with multiple delivery fibers allows most or all of the available laser energy generated by the laser source to be applied to tissue achieving Flash Vaporization with optimal ablation efficiency. Multiple delivery fiber configurations increase the system's overall ablation rate to meet clinical needs where it is desirable to directly vaporize tissue faster than a single delivery fiber can achieve while maintaining Flash Vaporization with optimal ablation efficiency.

Figure 8:
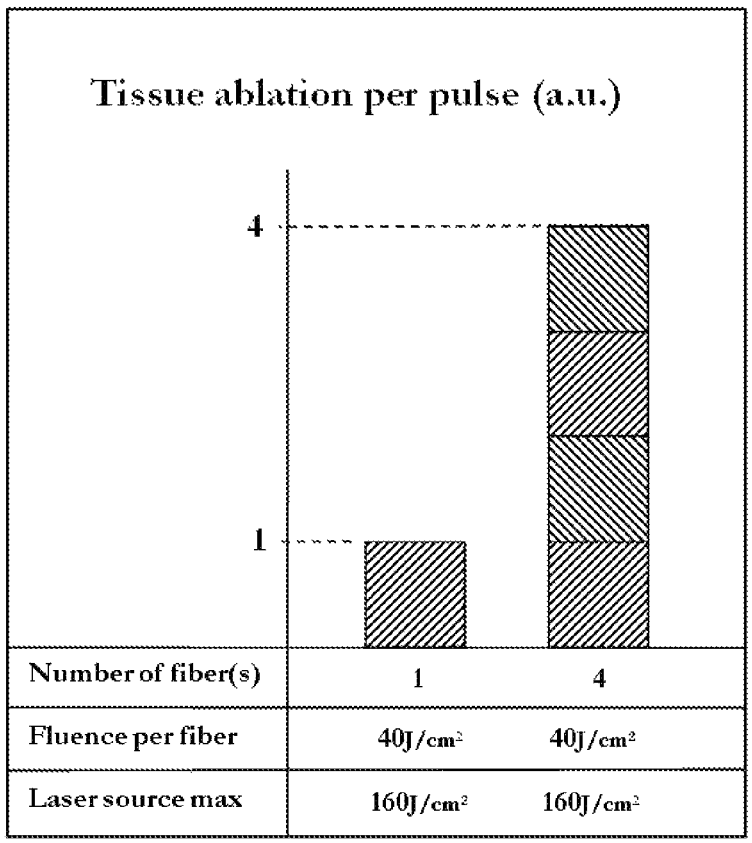
FIG. 8 shows tissue removal for a single fiber Flash Vaporization system versus a 4-fiber Flash Vaporization system.

For example, it may be necessary to ablate a large brain tumor. The use of parallel pulse delivery to achieve high ablation rates can be understood with reference to the table shown in FIG. 8. Assume Flash Vaporization at the optimal ablation efficiency is achieved with a fluence of about 40 J/cm$^2$. As discussed, increasing the fluence beyond 40 J/cm$^2$ does not improve the ablation speed. An exemplary laser may be capable of generating a pulse within the Flash Vaporization parameter space that well exceeds the 40 J/cm$^2$, for example a pulse that would equate to 160 J/cm$^2$, 4 times greater than what is required for optimal efficiency. By generating a pulse capable of supporting 160 J/cm$^2$ and then dividing the pulse simultaneously and roughly equally among 4 individual fibers, each fiber can deliver to tissue a fluence of 40 J/cm$^2$, at optimal efficiency in parallel. When the fiber output ends are arranged to treat separate tissue regions, typically adjacent to one another, 4 times more tissue per pulse is removed while maintaining optimal ablation efficiency.

The increased rate of tissue ablation achieved by utilizing multiple fibers has been described for an individual pulse, but is applicable to a sequence of pulses as well. For faster tissue ablation, the multiple fibers are typically an integrated part of the delivery device with each fiber output corresponding to a separate treatment site, typically adjacent to one another. The number of fibers utilized is scalable within the limits described.

In the example of sessile colon polyps one could choose to use a fiber bundle arranged in a semi-circular fashion with five fibers, where the laser can produce a pulse capable of generating a fluence five times larger than the single fiber optimal ablation efficiency fluence. The pulse can be divided equally into 5 parts and then coupled simultaneously into 5 individual fibers. For each laser pulse generated, 5 times more tissue is removed than can be achieved with a single fiber.

Figure 9:
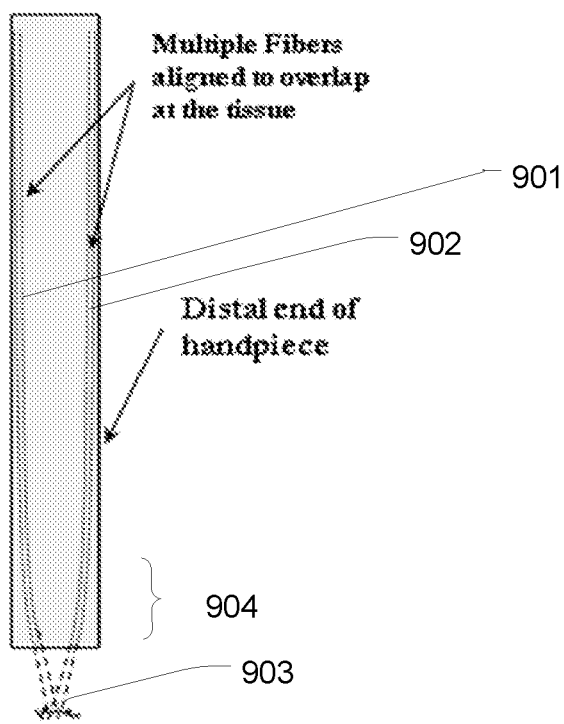
FIG. 9 shows a multi-fiber delivery system where the individual fiber outputs are overlapped at the treatment site.

Some tissue types have relatively high mechanical strength and require higher pressures to break apart the tissue matrix. A significant limitation occurs if the Flash Vaporization parameters required to achieve the necessary pressure exceed the power handling capabilities of a single silica fiber, as described in Equation 13. For example, the collagen of the dermal matrix is very strong and elastic. The pressure required to achieve Flash Vaporization in the dermis is higher than most other soft tissues. For the dermis example, a reasonable assumption for the fluence required for Flash Vaporization might be 200 $J/cm^2$ this however exceeds the capability of the fiber; thus we are presented with a challenge. This problem can be readily addressed by utilizing multiple fibers arranged in a configuration such as that illustrated in FIG. 9. Multiple fibers 901, 902 configured so that the output overlap in a single spot in the region 903 on the treatment site enables Flash Vaporization pressures far in excess of that achieved by a single fiber. An exemplary laser would generate the requisite energy for optimization of fluence at the target through two or more fibers. At or near the distal end 904 of the device, the output beams of the fibers are organized to overlap one another at the treatment site. For example each fiber carries a pulse corresponding to the equivalent of 100 $J/cm^2$, well below the fiber damage threshold. The fibers are configured such that the output beams overlap completely thus achieving 200 $J/cm^2$ at the treatment site. Using multiple fibers enables Flash Vaporization to occur with fiber delivery in tissues where single fiber delivery cannot achieve Flash Vaporization. One embodiment for the delivery device is to have the fibers bent and/or angled near the output such that the output beams overlap completely at the treatment site, as illustrated in FIG. 9. The delivery device may have slots, grooves or some physical means to align and secure each fiber such that the output beams are overlapped at the treatment site.

Figure 10:
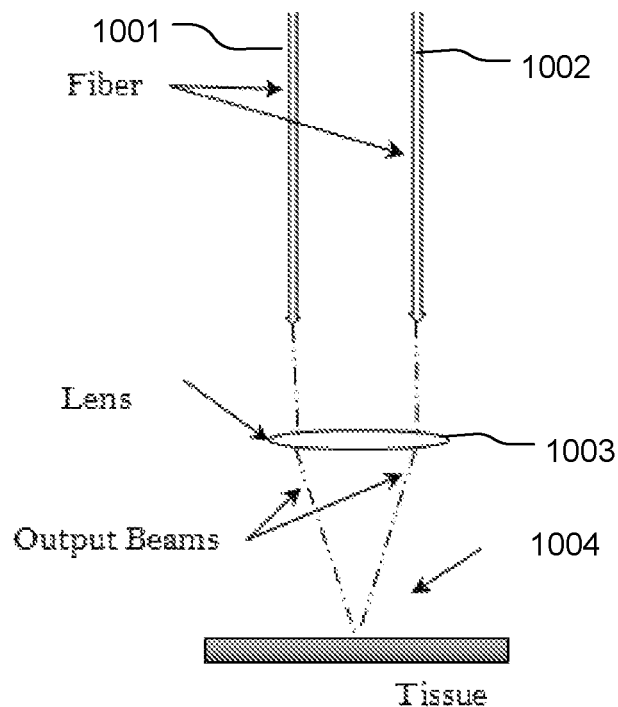
FIG. 10 shows an alternative multi-fiber delivery system where the individual fiber outputs are overlapped at the treatment site.

An alternative embodiment may employ focusing optics near the device tip such as shown in FIG. 10. In FIG. 10, a plurality of fibers 1001, 1002 is arranged in a manner such as might occur through an endoscope. At the distal end, a lens 1003 is positioned to redirect the outputs of the plural fibers 1001, 1002 so that they overlap on a spot 1004 on the treatment site on the tissue. Each fiber 1001, 1002 is positioned and secured in the delivery device such that the output beam passes through an optical element (e.g. lens 1003) that in part ensures the output beams of each fiber overlap at the treatment site. The optical element may be an integral part of the fiber tip such as a shaped tip, graded index fiber tip, tapered tip or other bonded, fused, attached or modified tips contributing to directing light. Additionally the optical element may be a single lens, individual lenses for each fiber, or any other configuration of optical element(s) that ensures overlap at the treatment site for each fiber output as illustrated in FIG. 10.

Achieving higher pressures during Flash Vaporization via the recombination of multiple fiber outputs can employ two or more fibers, one or more optical elements and/or numerous mechanical positioning and mounting configurations.

Figure 11A:
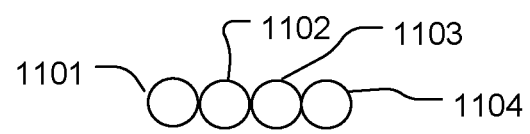
FIGS. 11A and 11B show a multi-fiber delivery device tip with the outputs arranged linearly and adjacent to one another and an exemplary direction of motion.

FIG. 11a illustrates a linear arrangement of fiber tips 1101, 1102, 1103, 1104 that can be utilized in a delivery tool, to provide for increased rate of cutting. The fiber tips 1101, 1102, 1103, 1104 in this example are positioned in a line, and adjacent to one another. Utilizing multiple fibers for faster tissue ablation additionally enables customized tip geometries that can be shaped to accommodate the needs of a given procedure.

Figure 11B:
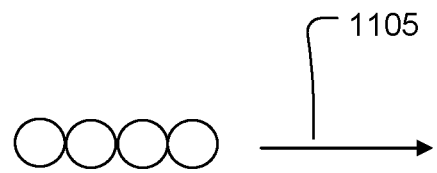

When a delivery device is configured in a line and is moved such that the line is along the cut direction represented by arrow 1105, see FIG. 11b, a scalpel-like cutting effect is achieved. The direction of motion mimics a standard scalpel, enabling cuts to be made faster than achievable with a single fiber.

Figure 12:
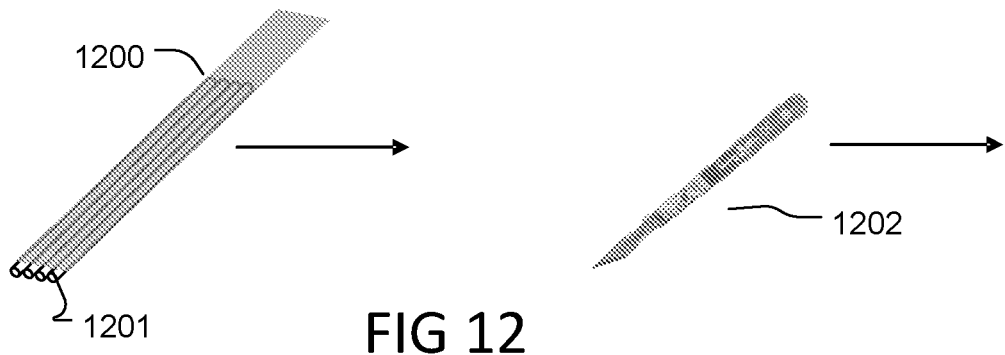
FIG. 12 shows an exemplary multi-fiber device configured to mimic a scalpel.

Alternatively, the fiber tips can be staggered to provide an angle with respect to the tissue. FIG. 12 is a perspective view of a four-fiber delivery tool 1200 in which the fiber tips 1201 are arranged in a staggered configuration, where a first fiber extends distally relative to the laser source by a small stagger relative to a second fiber, and so on in a stairstep configuration through all of the fibers in the line. The sizes of the stairstep can be equal or varied as suits the needs of a particular arrangement. Representative sizes of the stairstep can be on the same order as the diameter of the fibers or smaller, for example. In the configuration of FIG. 12, the direction and angle of the device handle can mimic a scalpel 1202 ergonomically.

Figure 13:
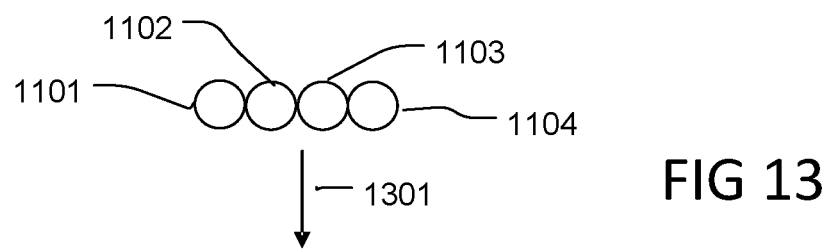
FIG. 13 shows an alternative direction of motion for a linear fiber tip arrangement.

With a linear device tip configuration, mass vaporization can be achieved by moving the device in the direction perpendicular to the fiber arrangement. As represented in FIG. 13, by the arrow 1301, a linear device tip including a plurality of fibers, such as fibers 1101-1104, can be moved in a direction orthogonal to the line of fibers.

Figures 14A, 14B, 14C:
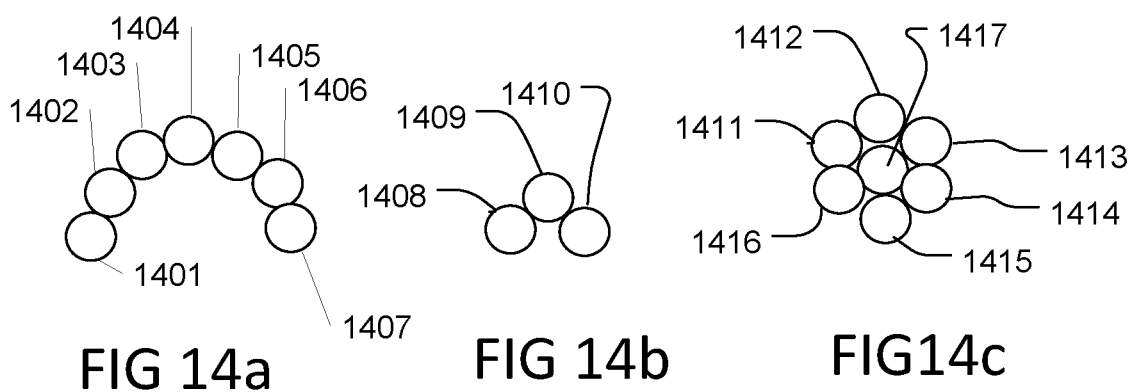
FIGS. 14A, 14B, 14C show exemplary multi-fiber device tip configurations for rapid tissue ablation.

When this configuration is moved across a target tissue, it provides rapid ablation of a strip width equal to the width of the fiber arrangement. FIG. 14a illustrates an arrangement of fiber tips 1401-1407 in a semicircular shape, as an alternative beam delivery tool. FIG. 14b illustrates yet another alternative, in which three fiber tips 1408-1410 are arranged in a nonlinear triplet. FIG. 14c illustrates a tightly packed cluster of fiber tips, where six fibers 1411-1416 surround a central fiber 1417.

Figure 15A:
FIGS. 15A-15B show directions of motion and exemplary multi-fiber device configurations.
Figure 15B:
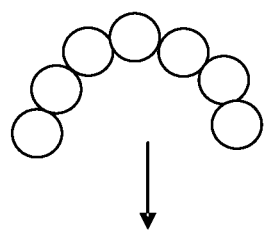

Each tip configuration can be chosen to accommodate the clinical need. The treatment spots created by each individual fiber would be unique and in general adjacent to one another. For example to debulk a sessile colon polyp a linear or curved arrangement may be employed such that the tip is drug across the tissue achieving vaporization over a large surface area per pass than a single fiber, as illustrated generally in FIGS. 15a and 15b.

Figure 16:
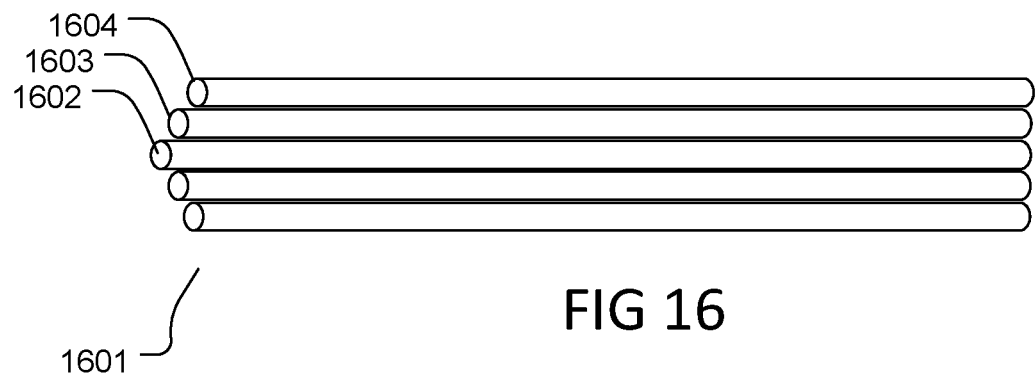
FIG. 16 shows an exemplary multi-fiber device tip configuration for generally spherical tumors.

For vaporization of tumors with a generally spherical shape, a multi-fiber tip 1601 may be used where the central portion 1602 protrudes further into the tissue than the fiber tips (e.g. 1603, 1604) closer to the edges, as illustrated in FIG. 16.

Figure 17:
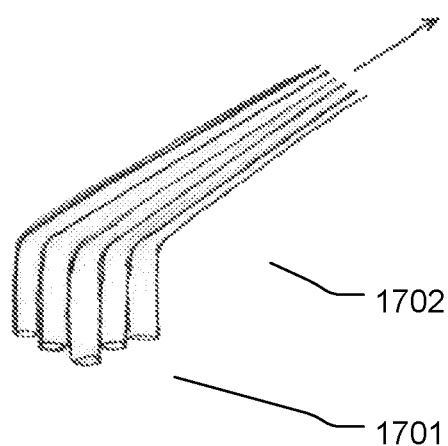
FIG. 17 shows an exemplary multi-fiber device tip configuration for generally cylindrical tumors.

For vaporizing tissue along the longitudinal axis of a generally cylindrical shape, such as in transurethral prostate resection, a tip 1701 with fiber tips arranged in a curved configuration can be used, with a near right angle bend 1702 employed to direct energy laterally, and quickly vaporize a large mass of tissue, as shown in FIG. 17.

Figure 18:
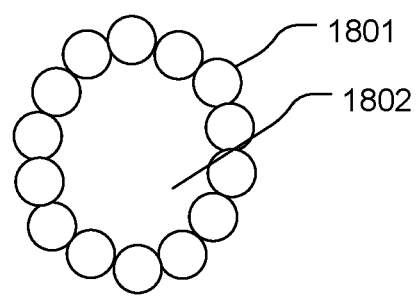
FIG. 18 shows an exemplary multi-fiber device tip configuration for pace maker lead removal.

For removal of pacemaker leads, a device that can be inserted coaxially with the wire lead is desirable. FIG. 18 shows a delivery device with a circular fiber arrangement 1801, with an open center 1802, which may enable Flash Vaporization of the tissue adhered to the wire's outer surface, allowing the lead to be detached and removed.

A tight circular formation can be used when mass tissue vaporization is needed and a painting motion over the diseased tissue is desirable. Using a painting motion the surgeon can control the depth of vaporization by hand to achieve a desired margin, for example to efficiently resect a tumor with large variations in depth, as shown in FIG. 14c.

In order to use multiple delivery fibers, a means to direct all or a portion of the laser energy into two or more fibers is necessary. Passive components such as partial reflectors are non-limiting examples of components that may be used to direct predetermined portions of the laser beam into multiple directions. Active components such as rotating mirrors are non-limiting examples of active means to direct portions of the laser beam in multiple directions. The beam path may be serial, parallel or any permutation of serial and parallel. The percentage of light from the source that is transmitted and ultimately coupled to each fiber may be static as determined by a beam directing component. Alternatively, active components such as shutters, modulators, attenuators and the like may be used to control when and what percentage of the source light is coupled into any individual fiber.

Figure 19:
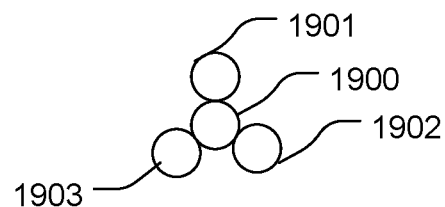
FIG. 19 shows an exemplary multi-fiber device tip configuration for using a painting motion to rapidly ablate tissue.
Figure 20:
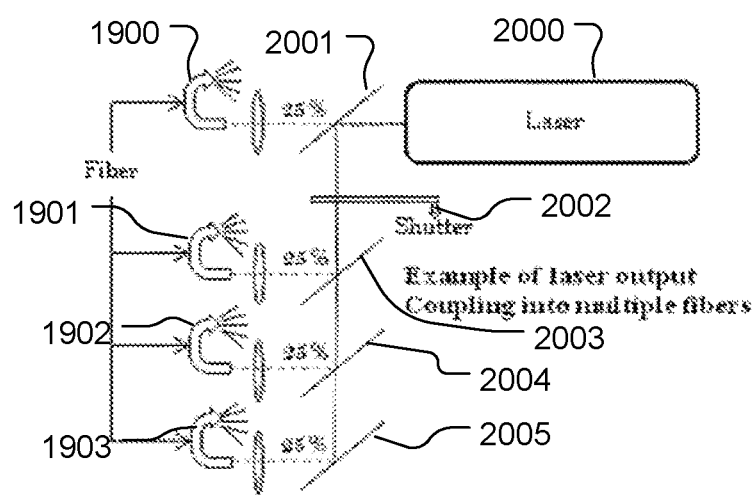
FIG. 20 shows an exemplary means to couple laser energy into multiple delivery fibers.

For example, a 4-fiber arrangement such as shown in FIG. 19, including fibers 1900-1903, may be desirable for large volume tissue ablation. This arrangement can be used with a system like that of FIG. 20. In this example the laser source 2000 generates a pulse that can be divided equally into 4 fibers while providing tissue ablation via Flash Vaporization for each fiber at adjacent tissue sites. In the arrangement of FIG. 20, the laser source 2000 generates output that intersects beam splitter 2001, which passes 25% of the energy through a fiber coupling lens into fiber 1900. The remaining 75% of the energy is directed past the shutter 2002 to a second beam splitter 2003, which deflects one third of the remaining 75% (i.e. 25% of the original energy) through a fiber coupling lens into the fiber 1901. The remaining 50% of the original energy is directed to a third beam splitter 2004, which deflects one half of the remaining 50% (i.e. 25% of the original energy) through a fiber coupling lens into the fiber 1902. The final 25% of the original energy is directed to the reflector 2005, through a fiber coupling lens into the fiber 1903. When mass tissue vaporization is required, the shutter 2002 is open and all four fibers will Flash Vaporize the target tissue. When precise cutting is needed, the shutter 2002 is closed and only one fiber receives a portion of the source pulse to Flash Vaporize the target tissue. Of course other arrangements of shutters and beam splitters can be utilized to implement a desired control sequence.

Using multi-fiber delivery techniques with the laser system for tissue-type selective ablation can provide for fast, and self-aligned ablation along a tissue type boundary.

For embodiments with two or more laser sources, similar fiber coupling techniques can be used.

Utilizing multiple fibers greatly expands the clinical capabilities of a Flash Vaporization tissue removal system.

Embodiments of the present invention can utilize flash vaporization to quickly and efficiently cut and resect one or more of many tissue types, for example without substantial thermal or mechanical damage to the tissue adjacent to the cut into the tissue. Removing tissue with decreased damage to the adjacent tissue regions can improve clinical outcomes, reduce the risk of adverse events and expedite the patient's recovery. A laser can produce pulses of light energy to eject a volume of the tissue, and the energy can be delivered to a treatment site through a waveguide, such as a fiber optic waveguide. The incident laser energy can be absorbed within a volume of the target tissue with a tissue penetration depth and pulse duration such that the propagation of the energy from the tissue volume is inhibited and such that the target chromophore within the volume reaches the spinodal decomposition threshold and subsequently ejects the volume, for example without substantial damage to tissue adjacent the ejected volume.

In a first aspect, embodiments provide a method of removing tissue with light energy. A pulsed beam of the light energy is directed toward the tissue. Each pulse irradiates a volume of tissue and has a duration and an amount of energy to inhibit stress and thermal energy propagation from the volume such that the volume of the tissue is ejected via the mechanism of spinodal decomposition.

In many embodiments, a pulsed beam of the light energy is directed toward the tissue. Each pulse irradiates a volume of tissue with a given energy and a duration short enough that most if not substantially all of the stress and thermal energy is confined within the volume and the tissue is ejected via the mechanism of spinodal decomposition. Furthermore, energy, pulse duration, and additional parameters described herein are selected for a given target tissue to achieve spinodal decomposition with substantial stress and thermal confinement, generating sufficient and/or optimal pressure within the target tissue to exceed the mechanical strength, tensile strength in some instances, of the target tissue such that substantially all the tissue within the interaction volume is ejected. Additionally the sufficient and/or optimal pressure may vary depending on the target material's characteristics.

In many embodiments, the target volume is heated with substantial stress and thermal confinement above a threshold of spinodal decomposition to a temperature of at least about 300 degrees C., such that a temporally and spatially uniform phase transition occurs within the volume to eject the volume without substantial energy deposition to tissue adjacent to the target volume. The temporally and spatially uniform phase transition within the entire target volume can create a confined recoil stress so as to efficiently remove the volume without depositing substantial energy in the surrounding region.

In many embodiments, the volume is ejected without substantial stress propagation of mechanical energy from the volume and without substantial thermal diffusion of thermal energy from the volume. The pulse duration may correspond to a dimension across the volume and a stress wave propagation time across the volume so as to substantially inhibit propagation of a stress wave from the volume.

Flash vaporization can be induced, given an optical penetration depth, OPD, as a function of the wavelength of the beam and the absorption coefficient for that wavelength in a primary chromophore such as water in the tissue, using a cross-sectional dimension of the beam at the target tissue sized to define an interaction volume such that on spinodal decomposition of the chromophore, the resulting pressure induced kinetic energy, causes ejection of remaining tissue in the target volume. Also, as a result of the size of the volume of tissue ejected by each pulse, and the pulse repetition rates applied, the rate of cutting accomplished using flash vaporization can be comparable to that possible when making fine incisions using a scalpel. Flash vaporization can be induced using a pulse duration short enough to maintain substantially stress confined interaction with the tissue, such that damage to surrounding tissue caused by tearing or other stress is not visible or not significant in terms of its effect on healing rates. Also, flash vaporization can be induced using a pulse duration short enough to maintain substantially thermally confined interaction with the tissue in the target volume, such that damage to surrounding tissue caused by heat is not visible or not significant in terms of its effect on healing rates. Flash vaporization can be induced using a wavelength suitable for delivery using silica optical fibers, or other flexible waveguides, while the pulse duration is long enough to allow delivery through the waveguide with only minimal damage or wear, so that fiber delivery is practical and preferred.

In many embodiments, each volume is irradiated with each pulse to define a depth and cross-section size of the volume based on the tissue's OPD, the pulse duration and the cross-section beam size such that the volume is substantially stress confined and substantially thermally confined to eject the tissue via the mechanism of spinodal decomposition. The light energy can be transmitted through an optical fiber, and the light energy may comprise a wavelength from about 1.4 microns to 1.52 microns or from about 1.86 to about 2.5 microns to define the volume based substantially on water absorption.

Representative durations of each pulse can be within a range from about 100 picoseconds to about 1 micro second. More typical pulse durations of each pulse can be within a range from about 500 picoseconds to about 200 nanoseconds.

In many embodiments, the volume ablated with each pulse is within a range from about $1\times10^{-8}$ cm$^3$ to about $1\times10^{-5}$ cm$^3$. In alternative embodiments the volume ablated with each pulse can be within a range from about $1\times10^{-7}$ cm$^3$ to about $1\times10^{-6}$ cm$^3$.

In many embodiments, the volume corresponds to a depth and a width ejected with each pulse and a ratio of the depth to the width is within a range from about 2:1 to 1:6. The volume may correspond to a depth and a width ejected with each pulse and a ratio of the depth to the width can be within a range from about 2:1 to about 1:4, as in the case of 1940 nm wavelength in tissue having water as a primary chromophore delivered via fibers having core diameters of 50 to 200 um in contact with, or near, the target tissue.

In many embodiments, the amount of energy of each pulse is within a range from about 100 micro Joules to about 100 milliJoules. In alternative embodiments the amount of energy of each pulse can be within a range from about 500 micro Joules to about 30 milliJoules. In additional embodiments the amount of energy of each pulse can be within a range from about 1 milliJoule to about 10 milliJoules.

In many embodiments, the tissue comprises collagen which may reach or exceed the liquefaction threshold with each pulse of the light energy.

In many embodiments, the tissue comprises one or more of vascular soft tissue, cartilage or bone.

In many embodiments, an elongated incision having a length and a depth is formed in the tissue with the light energy, and the length and the width correspond to an area of the incision into the tissue and wherein tissue removal rate is at least about $10^{-8}$ cm$^3$/pulse up to $10^{-4}$ cm$^3$/pulse. Pulse repetition rates from single shot to 2000 Hz are representative. For fine or microscopic cutting, repetition rates less than 100 Hz may be used, including single pulse triggering to cause pulse-by-pulse operation.

In many embodiments, the light energy is transmitted through at least one optical fiber with an energy transmission efficiency of at least about 80%.

In another aspect, embodiments provide an apparatus to treat tissue. A laser generates a pulsed beam of light energy comprising a plurality of light energy pulses. Each pulse irradiates a volume of tissue and has a duration and an amount of energy so as to substantially inhibit stress and thermal energy propagation from the volume such that the volume of the tissue is ejected via the mechanism of spinodal decomposition. A controller is coupled to the laser to generate the pulsed light beam in response to commands from the controller.

In many embodiments, at least one optical fiber is coupled to the laser, and the plurality of pulses of the pulsed beam transmitted through the fiber to the tissue such that each pulse transmitted through the fiber is capable of irradiating a volume of tissue and has a duration and an amount of energy so as to substantially inhibit stress and thermal energy propagation from the volume such that the volume of the tissue is ejected via the mechanism of spinodal decomposition.

Flash vaporization is a unique and clinically important new capability. As described herein, different target tissue may have different mechanical properties, requiring different amounts of threshold and/or optimal pressure to be generated within the treatment volume to eject substantially all of the material. It is desirable to provide surgeons with a cutting system that enables flash vaporization with efficient tissue ejection across a variety of tissue types. The versatility to cut a diverse variety of tissue types without substantially any thermal or mechanical damage to the tissue adjacent to the target volume enables surgeons provide better outcomes, less risk and shorter recovery periods for their patients.

Although specific reference is made to flash tissue vaporization, the flash vaporization as described herein can be used to flash vaporize many types of material, such as non-tissue material comprising water, for example.

A process is described including selecting a pressure to match tissue types; and adjusting the pressure to at least eject substantially all the target volume, wherein different tissue types have different threshold pressures. Also, a process is described including adjusting pressure with constrained ranges of wavelength, pulse duration, energy per pulse, and spot size parameters to at least achieve an ejection threshold for the target tissue.

As described in detail below, a laser surgery system which produces pulse sequences that are configured to cause removal of certain tissue types while simultaneously not causing removal of other tissue types in the target field of the surgery is based on utilizing Flash Vaporization, including inducing spinodal decomposition, as described herein.

Differences between ablation thresholds to induce ejection pressures (as selected by setting laser parameters) for different tissue types and the effect of the laser pulses on tissue types, including different soft tissue types, having thresholds close to, but below the ablation thresholds of the target tissues is substantial for flash vaporization. Soft tissue types include tissue types that connect, support, or surround other structures and organs of the body. Soft tissue includes muscles, tendons, ligaments, fascia, nerves, fibrous tissues, fat, blood vessels, and synovial membranes, and excludes bones, tooth enamel, dentin and cementum.

As a result, setting laser parameters above threshold for a first tissue type, but below threshold for a second tissue type, where the second tissue type can include soft tissue types, a new surgical technique is provided, by which the second tissue type behaves as an ablation stop defining a boundary of the ablation along the boundary between the tissue types. The second tissue type is not destroyed, and in at least some cases not seriously harmed by laser pulses set at the threshold for the first tissue type, while the first tissue type is ablated by flash vaporization without substantial thermal damage to adjacent tissues of either the first or second tissue types.

Embodiments of the present invention provide improved methods and apparatuses so as to provide versatile and effective tissue removal. A surgical laser system may comprise dynamic pulsing control of pulse width and intensity coupled to a user interface, such that the user can select a broad range of tissue treatment, including and in addition to tissue selective flash vaporization. For example, the system may allow a user such as a surgeon to select a target tissue response ranging from cold ablation, including tissue selective flash vaporization, through to coagulation. The target tissue response may comprise a user selectable response desired by the surgeon based on visual feedback from a surgical image such as an endoscopic image. For example, the tissue response can range from cold ablation, including flash vaporization, without substantial coagulation to coagulation with minimal ablation. The cold ablation, including flash vaporization, may comprise cutting soft or hard tissue with short pulses having a duration of no more than about 500 ns, for example, such that the tissue may be cut without substantial thermal deposition and without substantial thermal damage to the underlying tissue of the ablation site. The laser beam may comprise a wavelength absorbed substantially with the tissue, for example such that a majority of the energy of the laser beam is absorbed within about 100 microns of tissue penetration. For example, the laser beam may comprise a wavelength within a range from about 1.8 to about 2.2 μm, such that the energy of the beam can substantially ablate the tissue with short pulses having a duration of no more than about 500 ns and such that the energy of the laser beam can induce thermal damage to the tissue with a continuous wave or repetitive pulses with a period less than about 2 ms. The thermal damage of the tissue may comprise substantial coagulation with a continuous wave or repetitive pulses with a period less than about 2 ms, for example, such that a substantial majority of the energy incident on the tissue results in thermal deposition and coagulation of the tissue with minimal tissue ablation. The user may select intermediate treatment modes where the corresponding tissue response is such that tissue is cut with moderate thermal deposition, for example. This substantial breadth of the targeted tissue response from cold ablation, including flash vaporization, to coagulation can be achieved, for example by dynamically varying the pump source and q-switch pulse parameters. The pump source and q-switch parameters can be varied independently, together, or in combinations thereof, for a selected exposure setting. For example the pump source parameters of the laser gain medium and q-switch parameters can be varied together when the tissue is treated, so as to provide the wide range of user selectable treatment.

The system may comprise a small core waveguide, for example less than about 100 μm, so as to provide very efficient cutting and coagulation, and to provide substantial accessibility to treatment sites with decreased invasiveness, for example endoscopic procedures to the sinus cavity accessed through a nose of the patient. The waveguide can be coupled to the laser such that the tissue at the treatment site is treated with the laser beam output in accordance with the targeted tissue response, for example one or more of cold ablation, including flash vaporization, ablation with coagulation, or coagulation without substantial ablation. As the user can change the targeted tissue response during treatment, for example in response to endoscopic images shown on a display, many surgeries can be performed with decreased invasiveness and improved results.

The user selectable cutting or coagulation of tissue can be achieved in many ways, for example, by pulsing the laser output beam in variable timing patterns and combinations. The pulses can be generated by pulsing the pump source, pulsing the laser beam with the q-switch, or pulsing both. The laser system may include a pump source such as laser diodes coupled to a gain medium, a q-switch, mirrors sufficient to create a resonate cavity with the gain medium disposed therein, optics to focus the output laser beam into a delivery device such as a waveguide, a controller with a tangible medium, and a user interface. The waveguide may comprise an optical fiber coupled to the laser output so as to direct the laser output from the laser source to the treatment site. The system may further comprise an insertion device that at least one of houses or holds the waveguide for insertion of the waveguide into the body. The insertion device may be shaped to accommodate access and placement of the waveguide for performing specific surgical procedures, such as surgery of the sinus cavity.

Embodiments of the present invention provide improved methods and apparatuses so as to provide versatile and effective tissue removal. The surgical laser system as described herein can be used with many surgical procedures and can be used to access many surgical locations of a patient, for example internal surgical locations. The surgical laser system has a user interface that allows the user to select a treatment based on a desired tissue response such as cold ablation, including flash vaporization, coagulation or ablation with intermediate levels of thermal damage. The laser system comprises circuitry coupled to the user interface and the laser, such that the circuitry can adjust the laser treatment parameters based on the tissue response identified by the user. The laser treatment parameters adjusted with the circuitry can include one or more of the pulse duration or exposure duration with continuous wave output, the output beam intensity, the intensity of the pumping of the gain medium, or pulsing of the gain medium, for example. The user can view an image of the tissue site, for example with an endoscope comprising viewing optics and the tissue treatment waveguide, and the user can select the desired tissue response based on the endoscopic images, such that the tissue can be cut with cold ablation, including flash vaporization, coagulated, or cut with a desired level of thermal damage as targeted by the user.

Figure 21:
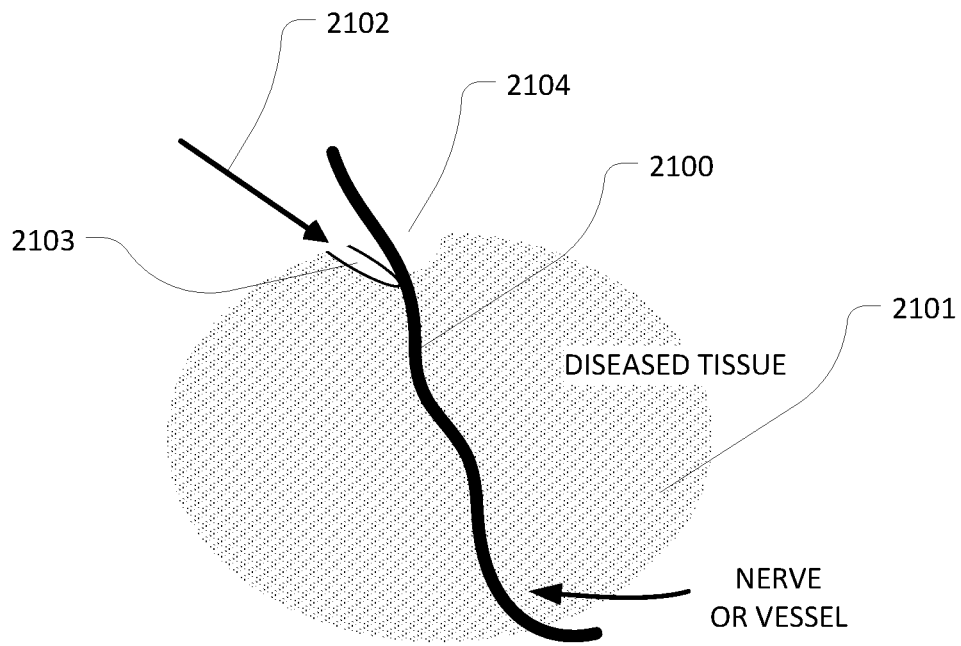
FIG. 21 illustrates tissue selective ablation surrounding a nerve or vessel.

FIG. 21 schematically illustrates a surgical field including a diseased tissue 2101 (a first type of soft tissue) penetrated by a nerve or vessel 2100 (a second type of soft tissue). Thus, the nerve or vessel 2100 is surrounded by diseased tissue. In this setting, it may be desirable to remove the diseased tissue 2101 without damaging the nerve or vessel 2100. In order to accomplish this, laser parameters of the laser system are set above threshold for flash vaporization of the diseased tissue 2101, and below threshold for flash vaporization of the outside layers (e.g., perineural tissue type or tunica externa tissue type) of the nerve or vessel 2100.

As the pulsed laser beam 2102 is delivered into the surgical field along the boundary between the diseased tissue and the nerve, pulses on delivery to the diseased tissue 2101 (schematically in the region 2103) are ablated by flash vaporization of the diseased tissue 2101 resulting in void 2104. As the laser beam is moved along the boundary, the pulses on delivery to the outside layers of the nerve or vessel 2100 do not result in ablation or destruction of the outside layers of the nerve or vessel. Using the ablation phenomena of flash vaporization, the pulsed laser beam 2102 on delivery to target tissue of the first type (diseased tissue 2101) delivers a volumetric power density to an interaction volume in the target tissue of the first tissue type that induces spinal decomposition in the tissue and kinetic energy confined within the interaction volume to eject tissue of the first tissue type. However, pulses of the pulsed laser being delivered to tissue of the second type do not create kinetic energy to remove the tissue of the second type, leaving the structure comprised of the second tissue type in place and acting as a flash vaporization stop.

As a result, the outside layers of the nerve or vessel 2100 in the surgical field shown in FIG. 21 act as an ablation stop, fully protecting the functional nerve or vessel tissue, while allowing efficient removal of the diseased tissue surrounding the nerve. Similar effects can be implemented in other types of tissues, including for example tissue types surrounding tendons or ligaments. Thus, the use of tissue-selective flash vaporization allows for selective removal the first tissue type relative to tissue of the second type.

As a result of the selectivity of the ablation process, a surgical technique for nerve mobilization is provided, by which a nerve bed can be ablated along a length of the nerve, allowing a segment of the nerve to be separated from the nerve bed and moved to provide access to structures otherwise underlying the nerve. Likewise, mobilization of vessels or other tissue types can be accomplished.

Figure 22:
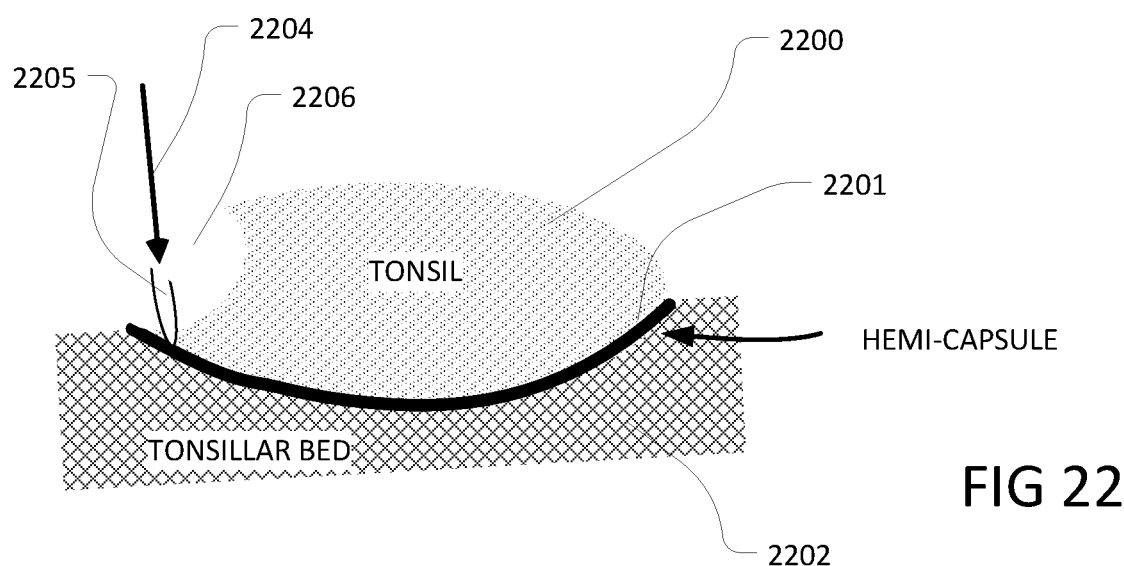
FIG. 22 illustrates tissue selective ablation of tonsillar tissue relative to a tonsillar capsule.

FIG. 22 schematically illustrates a surgical field including a tonsil 2200, a tonsillar hemi-capsule 2201, and a tonsillar bed 2202. In a surgical process to remove the tonsil 2200, laser parameters are set above threshold for the tissue type (e.g. lymphatic or epithelial tissue types) of the tonsil 2200 and below threshold for the tissue type of the tonsillar hemi-capsule 2201.

As the pulsed laser beam 2204 is delivered into the surgical field, pulses on delivery to the tonsil 2200 (schematically in the region 2205) are ablated by flash vaporization of the tissue types of the tonsil 2200 resulting in void 2206. The procedure can continue along the boundary created by the capsule 2201 (also called hemi-capsule) until all of the tonsil tissue is removed in some cases. The pulses on delivery to the capsule 2201 do not result in ablation or destruction of the tissue, fully protecting the underlying tonsillar bed 2202. Using the ablation phenomenon of flash vaporization, the pulsed laser beam 2204 on delivery to target tissue of the first type (tissue types in the tonsil 2200) delivers a volumetric power density to an interaction volume in the target tissue of the first tissue type that induces spinal decomposition in the tissue and kinetic energy confined within the interaction volume to eject tissue of the first tissue type. However, pulses of the pulsed laser being delivered to tissue of the second type (capsule 2201) do not create kinetic energy to remove the tissue of the second type, leaving the structure comprised of the second tissue type in place and acting as flash vaporization stop.

Figure 23:
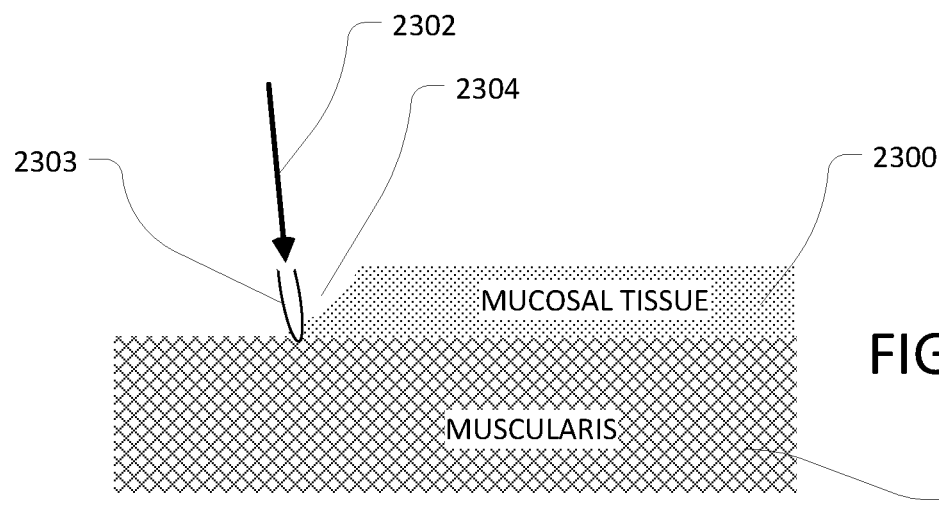
FIG. 23 illustrates tissue selective ablation of layered tissues.

FIG. 23 schematically illustrates a surgical field including multiple layers of tissues of different tissue types, in this example a layer of mucosal tissue 2300 and a layer of muscularis 2301. In a surgical procedure to remove the layer of mucosal tissue 2300, using tissue-selective ablation as described herein, the layer of muscularis 2301 can be preserved and act as a ablation stop. In this procedure, laser parameters are set above threshold for the first tissue type of the top layer (mucosal tissue 2300), and below threshold for the second tissue type of the underlying layer (muscularis 2301). A procedure can involve moving the laser beam so that it ablates the mucosal tissue 2300 exposing the boundary between the mucosal tissue 2300 and the muscularis 2301. The laser beam 2302 can be moved along the boundary (schematically in the region 2303) resulting in creation of the void 2304, and relying on the ablation stop characteristics of the muscularis 2301 for the particular settings of the laser as mentioned above, to protect the muscularis 2301.

The pulses on delivery to the muscularis 2301 as the beam is moved along the boundary do not result in substantial damage to the muscularis 2301, and in some cases do not result in any ablation. Surgically beneficial results are achieved if the ablation rate of the mucosal tissue 2300 is at least four times faster than that of muscularis 2301, allowing the surgeon to observe exposure of the muscularis 2301 and a smaller amount of ablation or thermal damage along the boundary, but that does not cause significant damage to the layer of tissue, and move the beam away from the muscularis as the upper layer is removed completely.

This technique is available for other types of layered tissue types, including the tonsil example discussed with reference to FIG. 22, and other layered tissue settings. This technique operates when the layers of tissues include a first type of soft tissue in the top layer, and a second type of soft tissue in the underlying layer.

Figure 24:
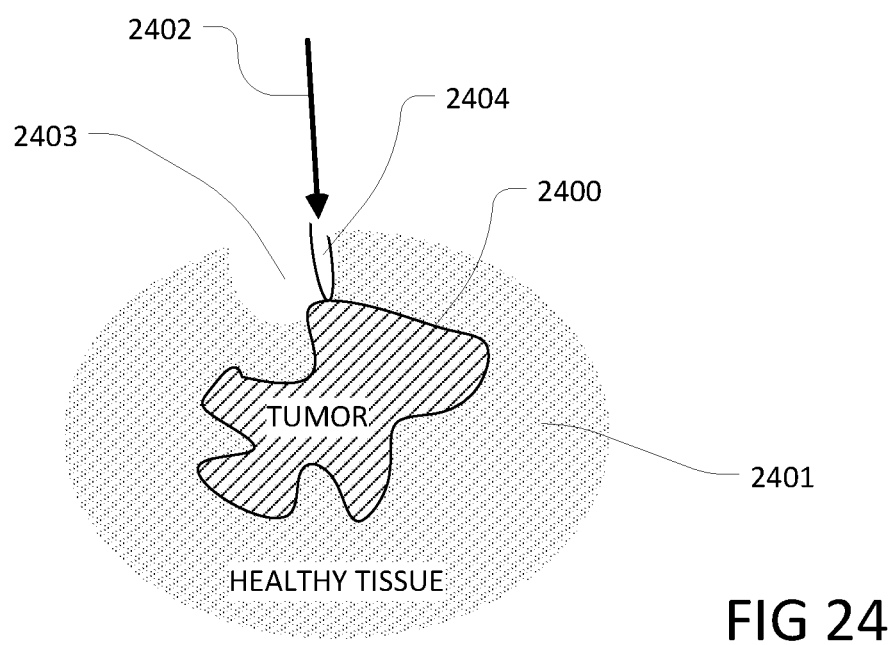
FIG. 24 illustrates tissue selective ablation surrounding a tumor.

FIG. 24 schematically illustrates a surgical field including healthy tissue 2401 surrounding a tumor 2400. In a surgical procedure to remove the tumor 2400, it may be desirable to remove a margin of healthy tissue along the boundary of the tumor. In this procedure, laser parameters are set above threshold for the first tissue type (healthy tissue 2401), and below threshold for the tissue type of the tumor 2400. The procedure can involve moving the laser beam 2402 so that it ablates the healthy tissue 2401 along the boundary between the healthy tissue and the tumor 2400, thereby exposing the boundary of the tumor 2400. This allows observation of the boundary of the tumor (schematically in region 2404) resulting in the void 2403, and as the procedure is executed around the tumor 2400 providing improved likelihood of removing a margin of healthy tissue surrounding the tumor 2400 along all the boundaries of the tumor.

Figure 25:
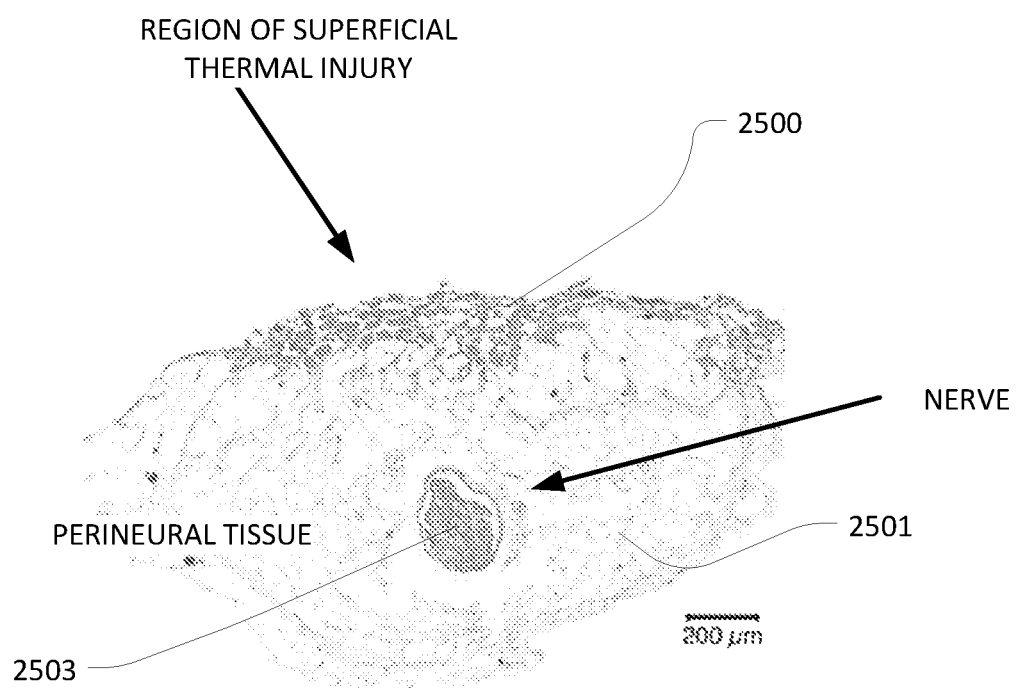
FIG. 25 is an image showing histology obtained from delivering below threshold flash vaporization pulses to a nerve sheath, without substantial damage.

FIG. 25 is a histological image showing a cross-section of a canine laryngeal nerve after prolonged exposure (1 second) to a pulsed laser beam having laser parameters above threshold for surrounding connective tissues as discussed above, and below threshold for the outside layers of the nerve. As seen in the image, the nerve bundle includes perineural tissue 2501 that surrounds and protects functional tissue 2503 of the nerve. In this example, the pulsed laser beam delivered repeated pulses to the outside surface of the nerve. As can be seen, even after repeated pulses, only superficial thermal injury is caused to the perineural tissue in the region 2500. The functional tissue 2503 of the nerve is fully protected. Thus, it has been demonstrated that the tissue-selective flash vaporization as described herein can provide a margin of safety for surgeons operating near nerves or in tissue surrounding nerves. Also, the technology can be used for mobilizing nerves with very low risk. Also, the technology can be used to remove tissue surrounding the nerves providing clear margins into the perineural tissue.

Figure 26:
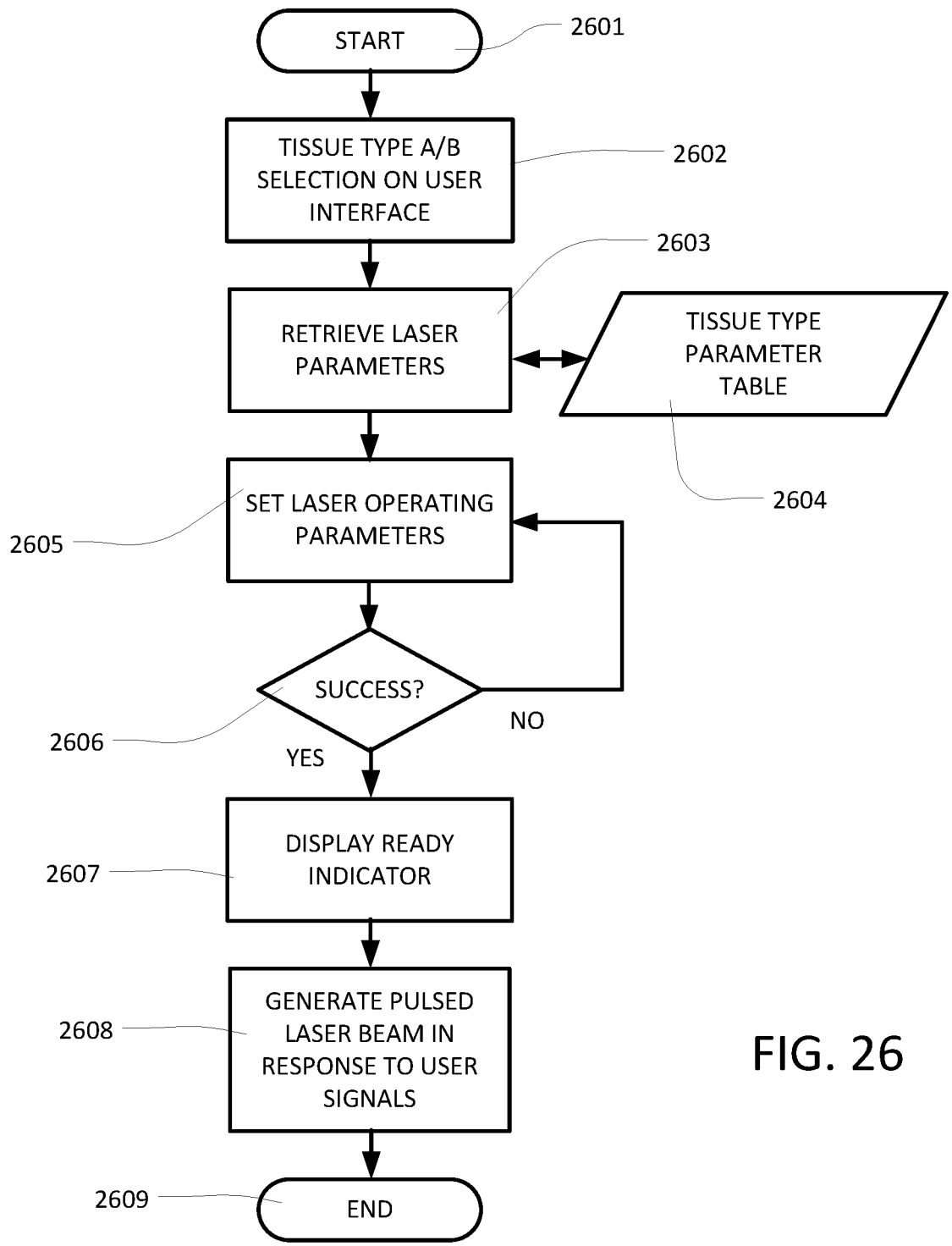
FIG. 26 is a flow chart for a method of tissue selective ablation.

FIG. 26 is a flowchart of a method for operating a laser for tissue-type selective surgery as described herein. The method is started by accepting a user input signal on the laser, such as turning on the power or providing an initiation command (2601). A user interface is displayed prompting the user to select a first tissue type (tissue type A) and a second tissue type (tissue type B) (2602). In response to user input selecting tissue type A and type B, the system retrieves tissue type laser parameters (2603) from a tissue type parameter table (2604). The tissue type parameter table 2604 can be stored in memory on a processor coupled to the laser system, or accessible to a processor coupled to the laser system via a communication network, or otherwise made available. Tissue type parameter table 2604 can store laser parameters configured to exceed the ablation threshold of tissue type A, while remaining below the ablation threshold of tissue type B. In some embodiments, the selection of tissue type can involve identification of a surgical procedure, in which the tissue types are implicit. In some embodiments, the laser parameter table 2604 maintains laser parameters for the ablation threshold of the tissue type to be removed, and minimally above that tissue type so as to preserve all or most tissue types that have higher ablation thresholds. In other embodiments, the laser parameter table 2604 maintains laser parameters for the ablation threshold of the tissue type to be removed relative to the tissue type to act as the ablation stop, so that the laser parameters can be more than minimally above the tissue type to be removed for some tissue type pairings.

After retrieving the laser parameters, the laser operating parameters are set in the laser system (2605). Next, an algorithm for verifying successful setting of the parameters can be executed. If the parameters are not successfully set (2606), then an algorithm to retry the laser parameter settings can be executed, returning to block 2605, for example. If the parameters are successfully set (2606), the laser system can display a ready indicator for the user, such as an update to a user interface notifying the operator that the system is ready for the specified surgical procedure (2607). When the system is ready, the system generates a pulsed laser beam according to the set laser parameters in response to user input signals, such as operation of a foot pedal or trigger by the surgeon (2608). If the procedure is completed, a user input signal can be accepted indicating the end of the procedure (2609).

The process described with reference to FIG. 26 assumes a human operator. This procedure can also be executed under robotic control, relying on machine vision or other process control technologies to move the pulsed laser beam along the boundary between the tissue types.

Figure 27:
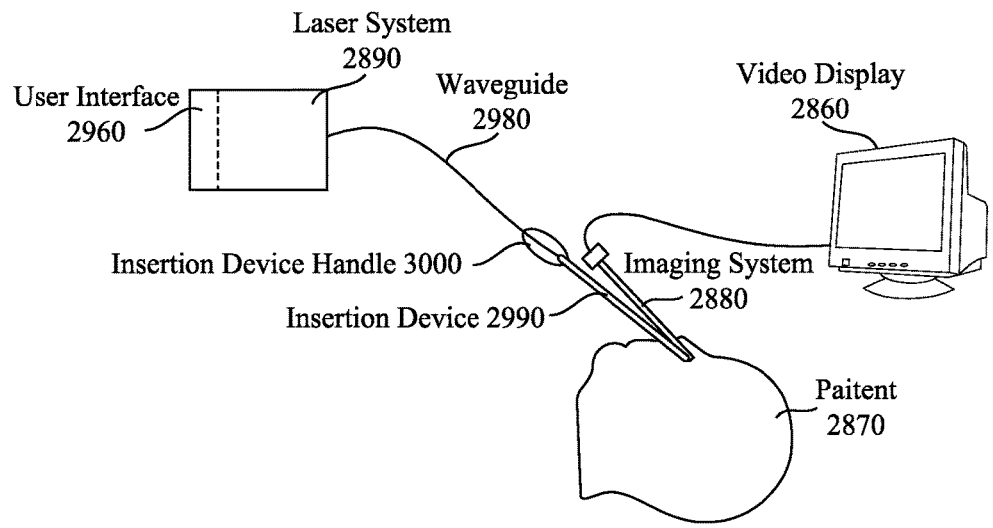
FIG. 27 shows a laser surgery system with an endoscopic probe inserted into a nasal cavity of a patient, according to embodiments of the present invention.

FIG. 27 shows the disclosed invention being used for sinus surgery. The patient 2870 has an imaging system 2880 inserted in a nostril. The imaging system 2880 may be a direct viewing type or it may have a camera with a video display 2860 such that the surgeon can view the inside of the sinus cavity. An insertion device 2990 with an insertion device handle 3000 and a waveguide 2980 is also inserted into the sinus cavity. The proximal end of the waveguide 2980 is attached to a laser system 2890 with a user interface 2960. The user can adjust the user interface setting to achieve the desired clinical effect. In one approach, flash vaporization as described above is utilized to remove tissue in the sinus cavity. The user interface 2960 also provides a means to activate the laser system to deliver energy to the treatment site via the waveguide 2980 and insertion device 2990.

Figure 28:
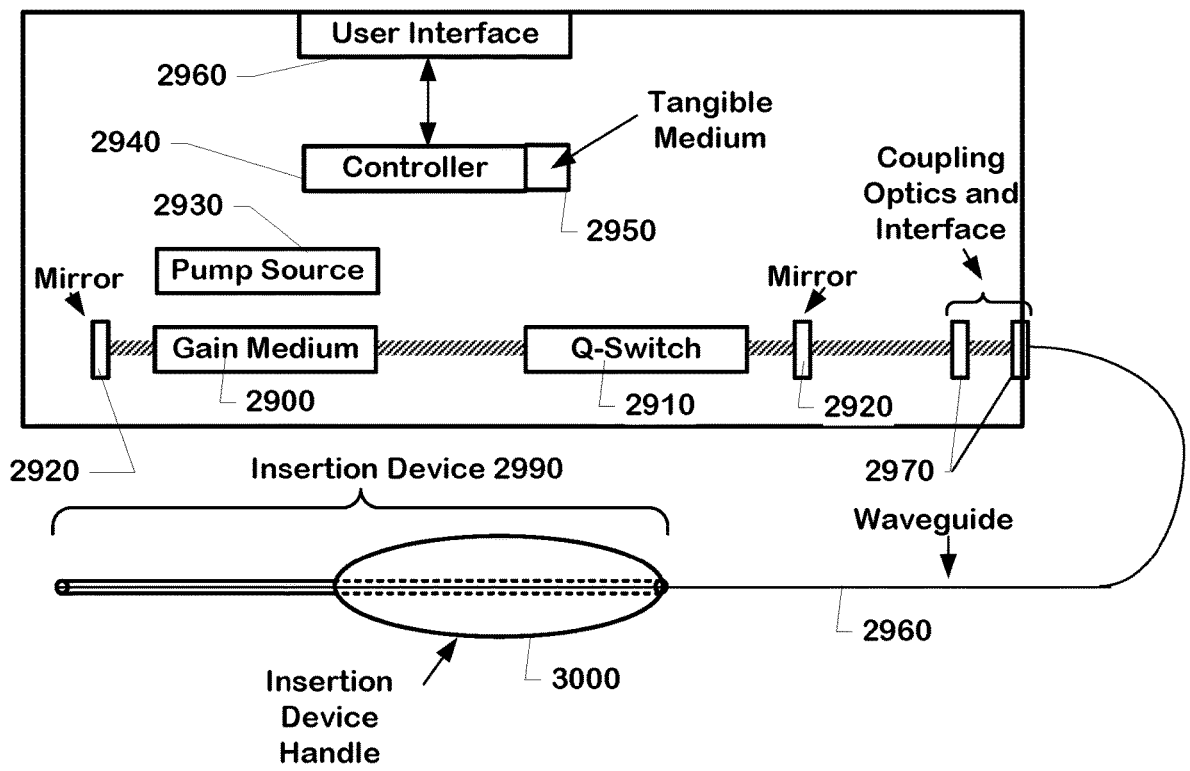
FIG. 28 shows the laser system of FIG. 27 for implementing a versatile and effective surgical tool with enhanced clinical capabilities, according to embodiments of the present invention.

FIG. 28 shows the laser system of FIG. 27 for implementing a versatile and effective surgical tool with enhanced clinical capabilities usable for tissue selective ablation in a variety of surgical settings and for a variety of tissue types. The laser system has a gain medium 2900 and q-switch 2910 disposed between at least two mirrors 2920 aligned to form a resonant cavity. A pump source 2930 provides energy to excite the gain medium 2900. A controller 2940 with a tangible medium 2950 may communicate or operate the pump source 2930 and the q-switch 2910. A user interface 2960 communicates with the controller 2940. The resulting laser energy passes through coupling optics 2970 to be coupled into a waveguide 2980. The waveguide 2980 passes through an insertion device 2990 used to insert the delivery system into a body. The insertion device may have an insertion device handle 3000 for the surgeon to hold and manipulate the insertion device 2990. In many embodiments, the laser system has a controllable pump source 2930 capable of generating a pulsed laser output beam. Some non-limiting examples of controllable pump sources include: flash lamp, arc lamp, hybrid lamp, diode laser, solid state laser, gas laser, dye laser, fiber laser and direct electrical stimulation. The pump source 2930 may in turn have a power source to operate it. The power source may be controllable to provide pulsed power to operate the pump source 2930 in a pulsed mode. Any means to control at least one of pulse amplitude, pulse duration or pulse period, preferably all three, can be sufficient. Dynamic pulse control may be in the form of one set of pulse parameters, fixed during an exposure, for a given user setting and alternative sets of pulse parameters, fixed during the exposure, for different user settings. Additionally, dynamic pulse control may be in the form of one or all pulse parameters changing during an exposure in a specified way for a given user setting, where each individual user setting may have different parameter changes during an exposure.

Figure 33:
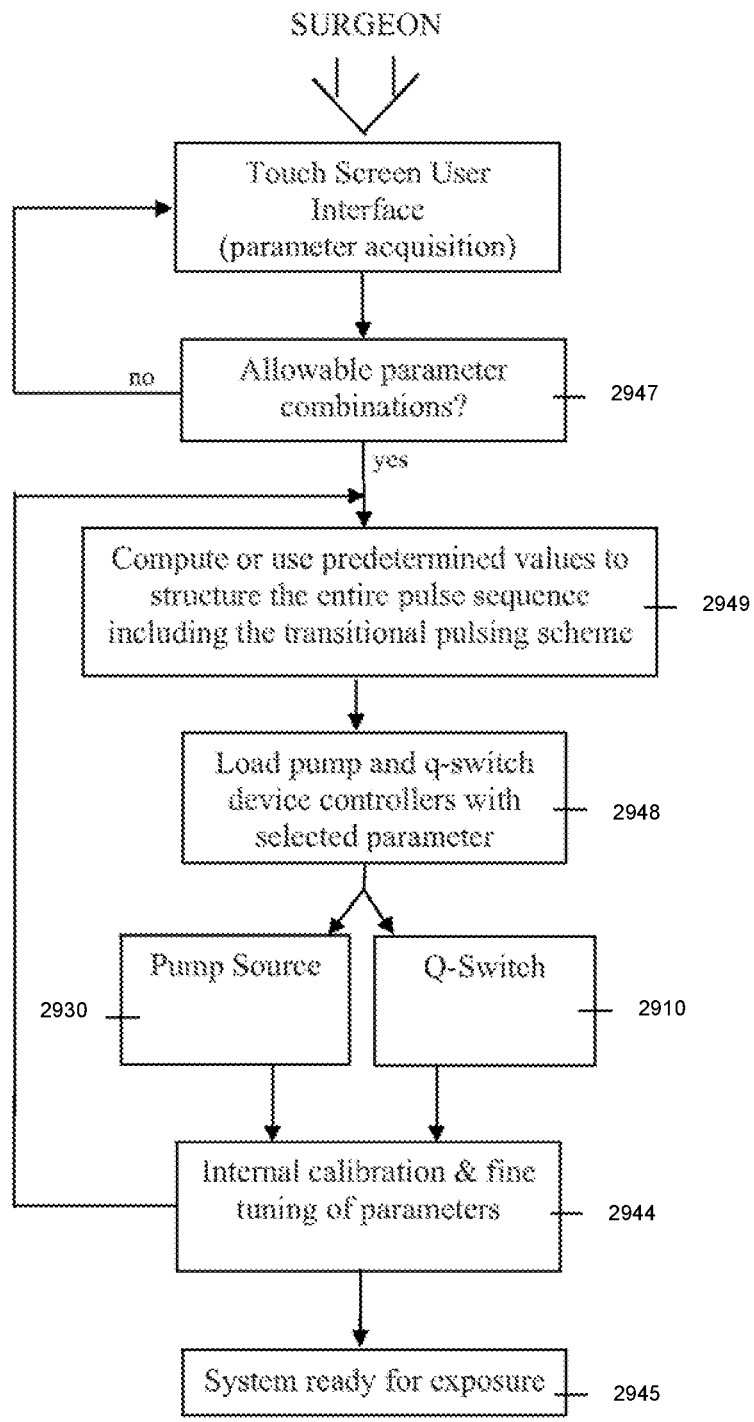
FIG. 33 shows a flow diagram of an exemplary control system for transitional dynamic pulses and a user interface as depicted in FIG. 32, including an exemplary flow diagram for interpreting the user settings and establishing the pulsing scheme with dynamic pulse transitions during an exposure, in accordance with embodiments of the present invention.

In many embodiments, the gain medium 2900 is relevant to the desired tissue effects and potentially relevant to the practical pulse parameters of the pump source 2930 and q-switch 2910. General types of gain mediums may include a solid state crystal, waveguide, polymer, gas, liquid or semi-conductor material. The gain medium 2900 can determine the allowable output wavelength or wavelength range. The wavelength can be relevant to surgical laser systems because the wavelength affects how strongly the light energy can be absorbed by tissue. Gain mediums and their respective output wavelengths can be grouped into three categories: strongly absorbed by water, strongly absorbed by blood, and in between, where absorption in both blood and water is relatively weak, as shown in FIG. 33.

Most tissue, including bone, has a higher water content than blood content so wavelengths strongly absorbed by water tend to be more strongly absorbed in most tissue. One method of enabling a broad dynamic range of tissue effects is choosing a wavelength that is strongly absorbed in tissue, so that in combination with the appropriate pulsing parameters the system can achieve an efficient 'cold' cut whereby leaving, at most, only a shallow coagulation depth or no visible coagulation in the remaining tissue. Wavelengths strongly absorbed in blood and the 'in between' wavelengths can also be used to enable a broad dynamic range of tissue effects, but their ability to create a 'cold' cut is more challenging and typically has a more complex and expensive pulsing implementation. Wavelengths that are strongly absorbed in water are preferred. Certain gain mediums can lase efficiently across a broad range of wavelengths and can thus be tuned to a specific wavelength or wavelength band within its tunable range. Wavelength tuning can be fixed, user adjustable or variable during an exposure. Tuning may enhance the system's ability to achieve a desired clinical goal. Thulium type gain mediums like Tm:YAP, Tm:YAG, Tm:YLF, etc. are typically strongly absorbed in water and can be readily transmitted down optical fibers. Tm:YAP has further advantages for surgical applications since it lases at 1.94 µm (a peak of water absorption) and a broad band of wavelengths above and below the water absorption peak. Tm:YAP also has an upper state lifetime of ~4 ms and therefore can be q-switched over a broad range of frequencies with high energy pulses. Laser systems designed with output wavelengths that are strongly absorbed by water may implement measures to prevent moisture from accumulating on the optical surfaces. Hermetic seal of the laser cavity, desiccants, inert gas purging and other techniques may be used to keep water from ultimately causing damage to the optical surfaces, including coatings. Similar measures may be used at the waveguide coupling interface.

In many embodiments, the system may incorporate a small core flexible waveguide 2980. One advantage of a small and flexible waveguide 2980 is enhanced accessibility. Small waveguides can accommodate small endoscope working channels allowing smaller overall diameters of the endoscopes without compromising clinical functionality. Flexible waveguides accommodate flexible endoscopes allowing access to areas where a straight line of access is difficult or impossible and the flexible scopes can do so without increasing the risk to the patient, for example, access to the maxillary sinus cavity base through the natural opening of the nostril rather than a hole cut into the cheek or gums. Additional examples include natural orifice transluminal endoscopic surgery where, for example, a gallbladder is treated via access into the mouth, down the esophagus, and through the stomach wall. An endoscope with limited flexibility cannot be suitable to reach the gallbladder via that path. Additionally, a flexible and small diameter endoscope can be more easily manipulated once the working tip is located at the treatment site, allowing surgeon to have better control to remove just the desired volume of tissue. Advances in small flexible scopes have enabled new and clinical beneficial ways to access target areas, although this equipment has been primarily for diagnostic purposes, in part, because no suitable surgical tools exist that can function well with the size, length and flexibility specifications to be compatible for performing treatments with these primarily diagnostic tools. An additional advantage of a small waveguide 2980 is that high irradiances or high fluences can be achieved with lower overall power or energy. For efficient ablation of hard or soft tissue some threshold energy for a given area should be exceeded.

With the appropriate choice of wavelength, beam quality and pulse parameters, a small low power system can outperform existing ablation technologies for tissue removal. Additionally, in part due to the small interaction area and proper parameter choices, the collateral damage can be substantially non-existent. If some thermal damage is desired, for instance to control bleeding, then the system parameters, such as enabling dual mode operation, can be adjusted such that some thermal damage occurs even with the small interaction area. High beam quality may enable the laser beam to be launched into a small core fiber optic waveguide 2980. The beam quality is both relative to the ability to focus down to a small enough spot to enter the waveguide 2980 and also to have a low enough numerical aperture to operate with minimal loss or damage when the fiber is bent during use.

The controller 2940 can be a centralized or distributed system that can control directly or indirectly the parameters of, at least, the pump source 2930 or q-switch 2910, preferably both. The controlled parameters may include pulse duration, pulse amplitude and pulse period. The controller 2940 may be capable of varying combinations of these pulse parameters down to an individual pulse basis. The controller 2940 may also operate the system in a non-pulsing mode for example continuous wave or quasi-continuous wave. The controller 2940 may include or communicate with, directly or indirectly, a means to tune the output wavelength. The controller may have a tangible, non-transitory data storage medium 2950, for example known RAM, ROM and flash memory. The controller 2940 may include or communicate with the system's user interface 2960 allowing the user to select a setting that the controller 2940 may interpret and determine and implement the necessary pulsing scheme to achieve the desired tissue effect. The controller 2940 may include or communicate with the power source for the pump source 2930 and/or the q-switch 2910. An exemplary and relatively simple user interface for dynamic pulsing is shown in FIG. 40. The power adjustment 2691, which can be related to the cutting rate, may be a knob, slide, button, touch screen or other meaningful interface mechanism allows the user to select a power setting. A thermal adjustment 2692 mechanism which may also be a knob, slide, button, touch screen or other meaningful interface mechanism would control the level of thermal deposition into the tissue for the given power setting ranging from 'cold', substantially all ablative with little to no residual thermal damage, to 'hot', substantially all thermal deposition with little to no ablation.

The surgeon may determine the appropriate settings based on the clinical need. Once the settings are made, the controller 2940 can prepare the pump pulse configuration, which may include the amplitude, period and pulse duration settings as well as the q-switch pulse configuration, which may include the amplitude, duration and period settings. In this example, the internal dynamic pulse parameter settings are within predetermined ranges for specific user interface input. Those predetermined ranges may be maintained in a portion of the controller tangible medium.

Figure 29:
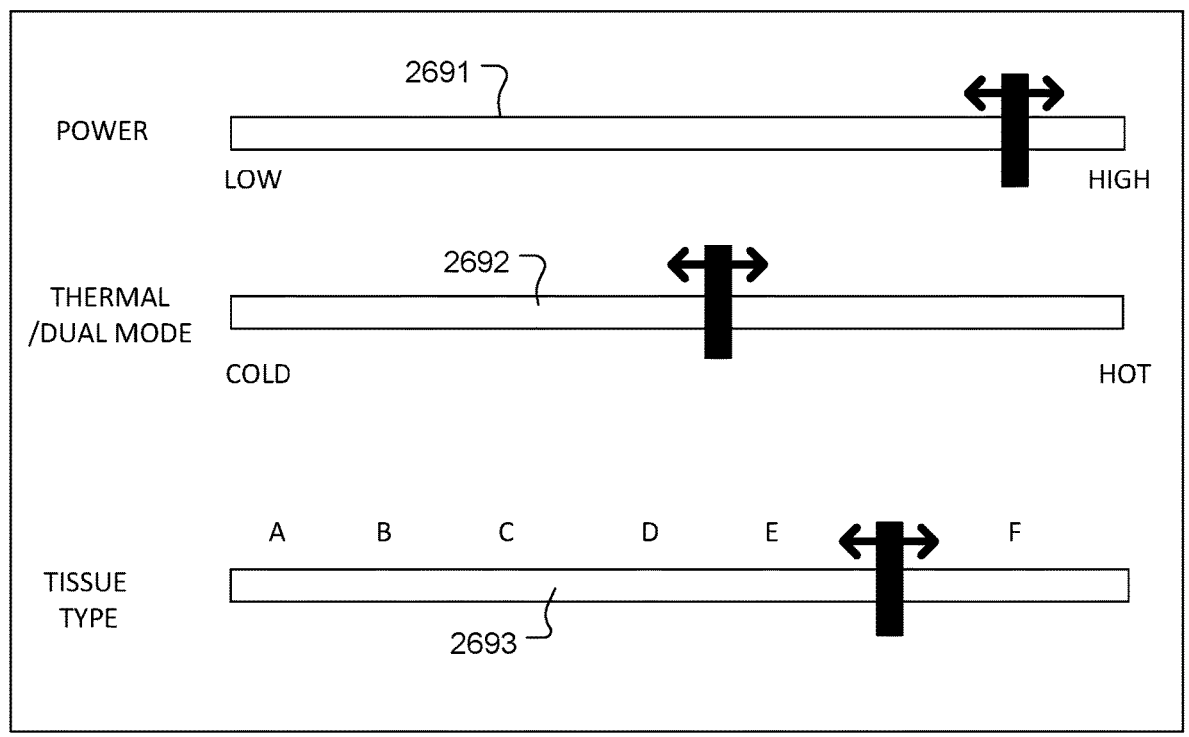
FIG. 29 shows an exemplary simple slide bar user interface with dynamic pulsing, in accordance with embodiments of the present invention.

FIG. 29 illustrates a user input device in the form of a set of touch screen sliders. The user input slide bar has been moved to the appropriate location. Now, based on the slide position the controller 2940 correlates to a predetermined set of parameters. For any inter-related parameter dependencies, for example q-switch pulse amplitude and q-switch period, the controller would determine the range limits and/or the mix of settings to achieve the desired outcomes as selected by the user. The dynamic predetermined settings may be adjusted during an internal calibration 2944 cycle to fine tune the parameters and accommodate the user power setting. When calibration is complete, the system is ready for an exposure 2945. The controller 2940 can coordinate the timing of the dynamic pulse sequences during an exposure. Many alternative user interfaces 2960 and control structures can be used.

In the illustrated example, the touchscreen includes a POWER slide bar 2691 with an input construct that is movable using the touchscreen input along the bar to establish a power setting. Also, the touchscreen includes a THERMAL/DUAL MODE slide bar 2692 with an input construct that is movable along the bar using the touchscreen input to establish dual-mode operations which can control thermal effects surrounding the ablation region, including a soft tissue flash vaporization mode and a bone (hard tissue) flash vaporization mode. For example, using the THERMAL/DUAL MODE slide bar 2692, a dynamic sequence of flash vaporization pulses combined with coagulation pulses can be generated to achieve the desired thermal effects. Also the touchscreen includes a TISSUE TYPE slide bar 2693 in this example. Using the TISSUE TYPE slide bar 2693, an input construct can be moved using the touchscreen interface to select ablation thresholds for a plurality of soft tissue types A-F. A user is able to select a threshold that is between first and second soft tissue types for a given procedure using the TISSUE TYPE slide bar 2693 in this example.

Other user input constructs can be utilized as wells, such as a list of surgical procedures that involve a plurality of tissue types, a list of tissue types in a pulldown menu, or other user input constructs. User input constructs for starting and stopping procedures, and other types of user input signal prompts can be included on the touchscreen. Also, user input can be provided using other types of input devices, such as keyboards, voice recognition, switches, dials and so on.

Figure 30:
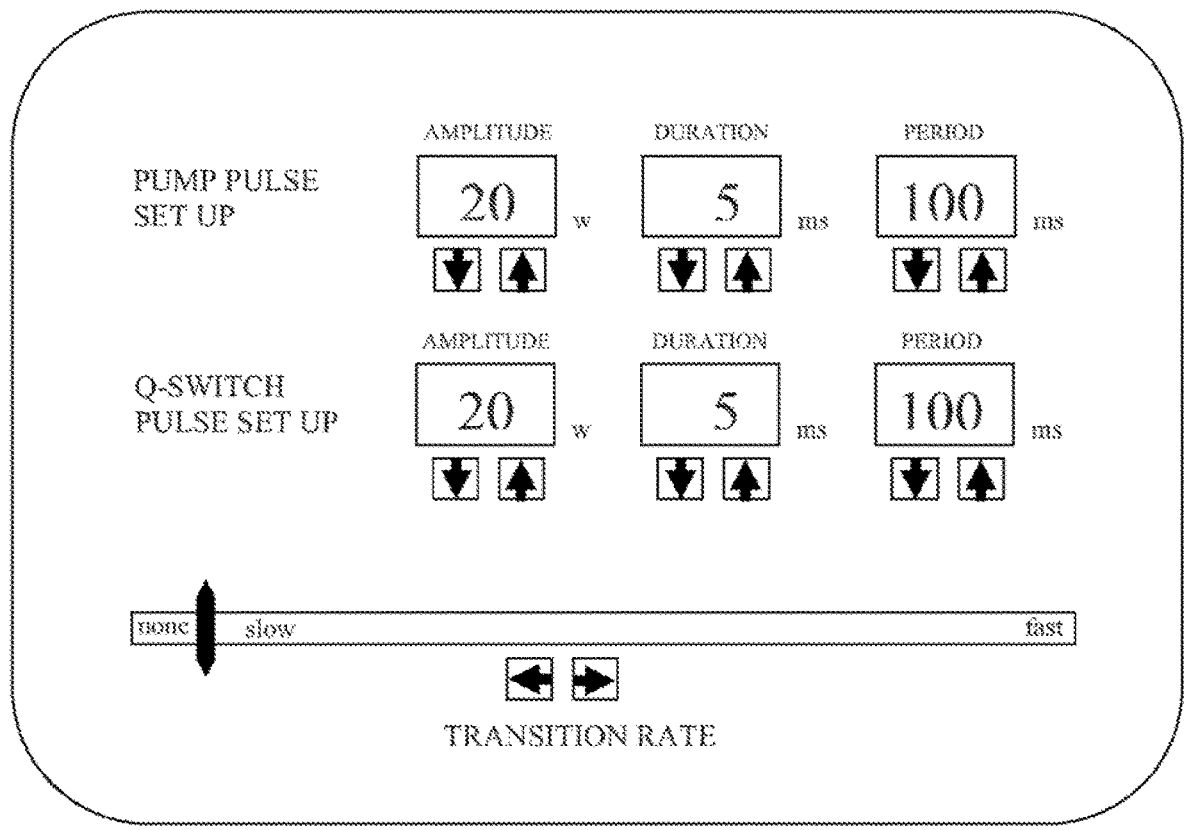
FIG. 30 shows an exemplary touch screen user interface for customizing dynamic pulse parameters without transitions during exposures, in accordance with embodiments of the present invention.

FIG. 30 shows an exemplary touch screen user interface for customizing dynamic pulse parameters without transitions during exposures which can be selected for various thermal effects, such as might be selected using the THERMAL/DUAL MODE slide bar 2692, of FIG. 29. In this example the dynamic pulse structure can be custom designed by the surgeon. The user can press the arrows on the screen to increase or decrease the adjacent parameter. For example, the user may be able to select each pulse parameter: amplitude, duration and period for both the pump pulses and the q-switch pulses. In this example the 'TRANSITION RATE' adjustment is set to 'none' so the user selected parameters remain fixed during the exposure.

Figure 31:
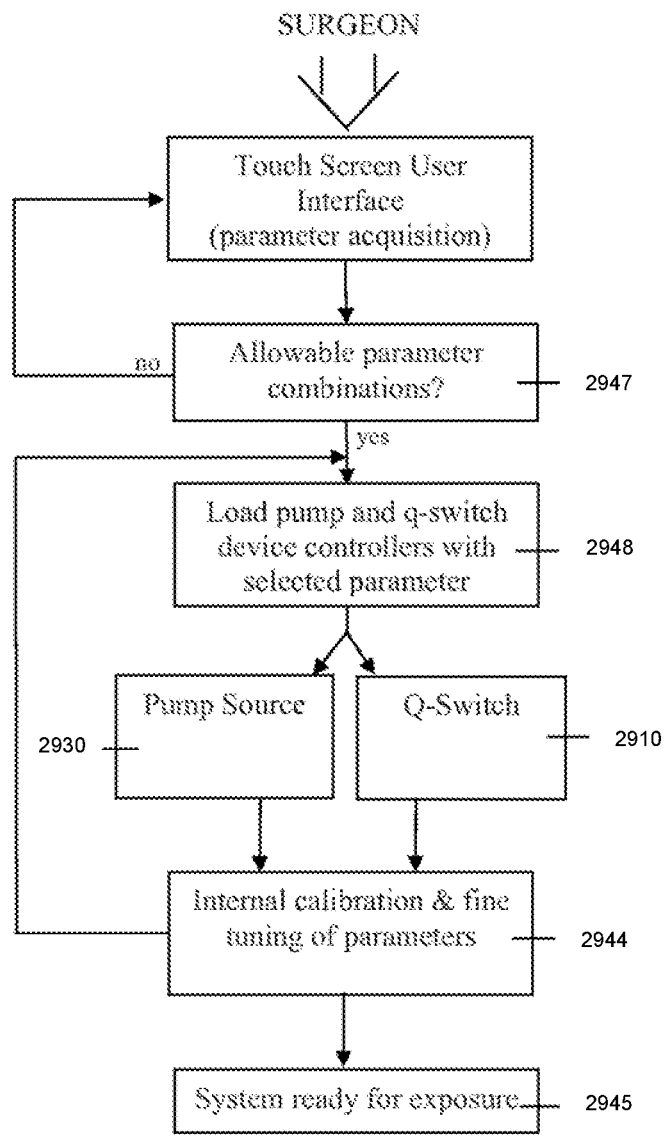
FIG. 31 shows a flow diagram of an exemplary control system for dynamic pulsing with a user interface as depicted in FIG. 30, including an exemplary flow diagram for interpreting the user settings and establishing the dynamic pulsing scheme without transitions during exposures, in accordance with embodiments of the present invention.

FIG. 31 shows a flow chart for an exemplary control system for dynamic pulsing with an user interface as depicted in FIG. 30. The controller 2940 can limit the range of parameters selections to achievable settings, allowable parameter combinations 2947, and manage the hierarchy of priority when selections are made. The system can then load pump and q-switch device controllers with selected parameters 2948. An internal calibration 2944 is performed. If necessary, some fine tuning of the parameters is performed to optimize the system, and then the system is ready for exposure 2945. The controller can coordinate the timing of the dynamic pulse sequences during an exposure.

Figure 32:
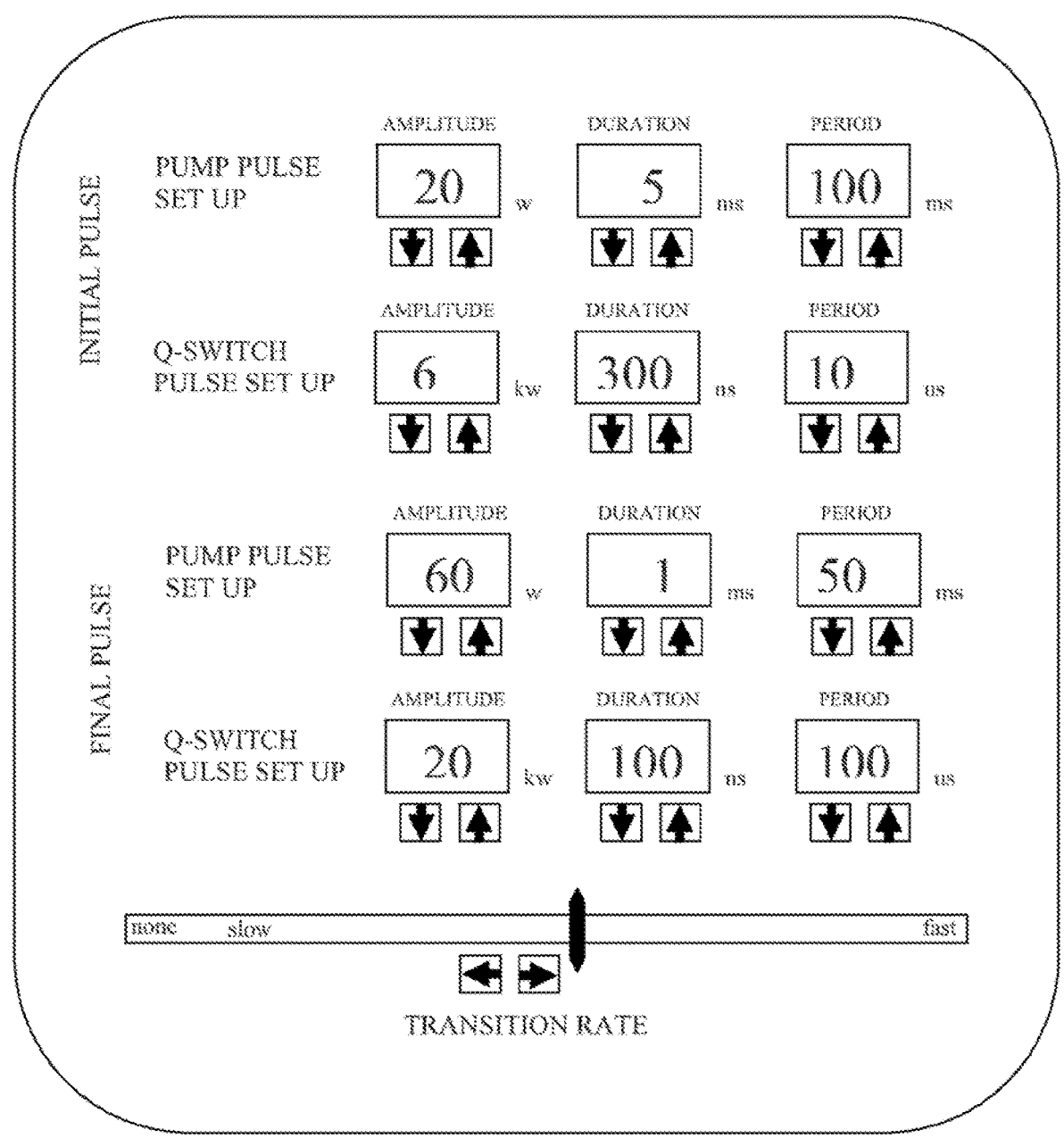
FIG. 32 shows an exemplary touch screen user interface for customizing dynamic pulse parameters with transitions during the exposure, in accordance with embodiments of the present invention.

FIG. 32 shows an exemplary user interface with a customizable dynamic pulse scheme including pulse transitions during the exposure. The user can press the arrows on the screen to increase or decrease the adjacent parameter. For transitioning pulse sequences the initial pulse sequence parameters are entered. Additionally, the final pulse sequence parameters are entered. The user selects a "TRANSITION RATE" varying from slow gradual transitions to fast abrupt transitions. In this example, the transition rate is midway between fast and slow.

FIG. 33 shows a flow chart for an exemplary control system with transitional dynamic pulses with a user interface as depicted in FIG. 32. The controller 2940 can limit the range of parameters selections to achievable settings, allowable parameter combinations 2947, and manage the hierarchy of priority when selections are made. For transitional pulse settings, the controller 2940 can compute or use predetermined values to structure the entire pulse sequences including the transitional pulsing scheme 2949. The system can then load pump and q-switch device controllers with selected parameters 2948. An internal calibration 2944 is performed. If necessary, some fine tuning of the parameters is performed to optimize the system and then the system is ready for exposure 2945. The controller can coordinate the timing of the dynamic pulse sequences during an exposure. The controller may interface with a user activation switch to activate the laser system. The user activation switch may be a hand or foot activated device and may include multiple functions.

Figure 34:
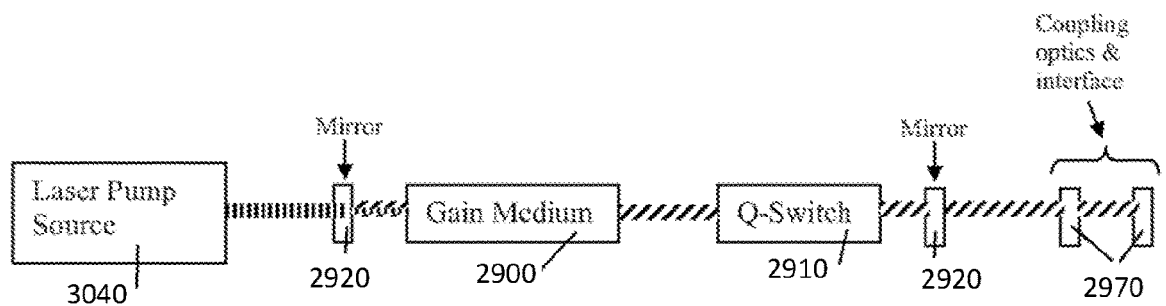
FIG. 34 shows a laser system using an end-pumping scheme to pump the gain medium, in accordance with embodiments of the present invention.

FIG. 34 shows a laser system using an end-pumping scheme to pump the gain medium, in accordance with embodiments of the present invention.

The resonator cavity may be formed with two mirrors 2920, one predominately reflecting the lasing wavelength and one partially transmissive to the laser output wavelength. The predominately reflective mirror may allow the pumping wavelength to pass through the mirror enabling the gain medium 2900 to be end-pumped with a laser source 3040, for example a diode laser. The intra-cavity elements are at minimum a gain medium 2900 and may include a q-switch 2910. Additional intra-cavity elements may include: lenses, substances for harmonic generation, elements to alter beam quality and various permutations of these elements. Cavities with more than two mirrors may also be used. A mirror may also be formed on the surface of an intra-cavity element rather than a standalone element.

The coupling optics 2970 direct the laser output beam such that it can be coupled into a waveguide 2980 and ultimately directed to a treatment site. Single, multiple or lens-less configurations can be used as well as other techniques to direct beams.

The waveguide 2980 is preferably a low OH silica fiber capable of transmitting IR light up to 2.5 µm. The waveguide 2980 can be made from other transmissive materials with consideration of the specific wavelength and powers being transmitted. The waveguide 2980 may have a secure recognition device integrated such that the laser system can recognize when the waveguide is attached. The delivery system may include additional instrumentation to house or hold the waveguide for example to allow insertion of the waveguide endoscopically. The instrumentation may further facilitate manipulation of the waveguide 2980 and/or the waveguide tip to perform specific surgical functions. The instrumentation may also include suction, irrigation, visualization, tissue manipulation functionality or their permutations.

In many embodiments beam quality may be an important parameter. Beam quality relates to the clinical tissue effect by affecting beam divergence at the output of the delivery device tip, thus affecting the irradiance impinged on the tissue. Beam quality also affects the minimal core size and numerical aperture of a fiber optic delivery device, which affects the overall size and practical bend radius of the delivery fiber. End pumping is a preferred technique to help achieve good beam quality. Other techniques may include apertures, intra-cavity transmissive elements, thermal management of the gain medium and the general design of the resonant cavity.

Pulse sequence structures can blend the cutting and coagulative tissue effects in ways advantageous for the surgeon to achieve an optimal clinical result. One clinical benefit of dynamically adjusting the pulse parameters and their permutations is that a surgeon can determine the appropriate level of thermal deposition, across a broad range, to control bleeding during surgery while preserving the viability of the remaining tissue. Another clinical benefit is that dynamic pulse control enables the removal of both hard and soft tissue. Dynamic pulse control also improves visibility for the surgeon during the procedure by controlling bleeding, smoke or both. Dynamic pulsing additionally allows the trauma to the remaining tissue to be controlled and thus expedites the patient recovery time and can also reduce pain and suffering during the recovery period. Gain mediums producing wavelengths strongly absorbed by water are preferred, but not necessary. These wavelengths provide a cost effective means to produce a surgical laser system encompassing a broad range of tissue effects. A high beam quality laser system enabling the use of small core waveguides is also preferred. The small waveguides enable improved accessibility and provide efficient tissue removal with minimal power or energy. Small waveguides are well suited for minimally invasive procedures. Providing surgeons with a tool to remove all types of tissue safely and effectively is beneficial for substantially all types of surgical procedures. The system is well-suited for endoscopic natural orifice procedures such as functional endoscopic sinus surgery, turbinate reductions, head and neck surgeries, colon, rectal, esophageal, bariatric, trans-vaginal, cystoscopic surgery and others. It is additionally well suited for laparoscopic surgeries such as appendectomies, hernia repair, bariatric, cholescystectomy, bowel resection, sterilization and others. Orthopedic, spine, neurologic, brain and traditional open surgeries can benefit as well. Future trends toward natural orifice transluminal endoscopic surgery can also benefit from a small flexible delivery system with broad and versatility selection of tissue effects.

Figure 35:
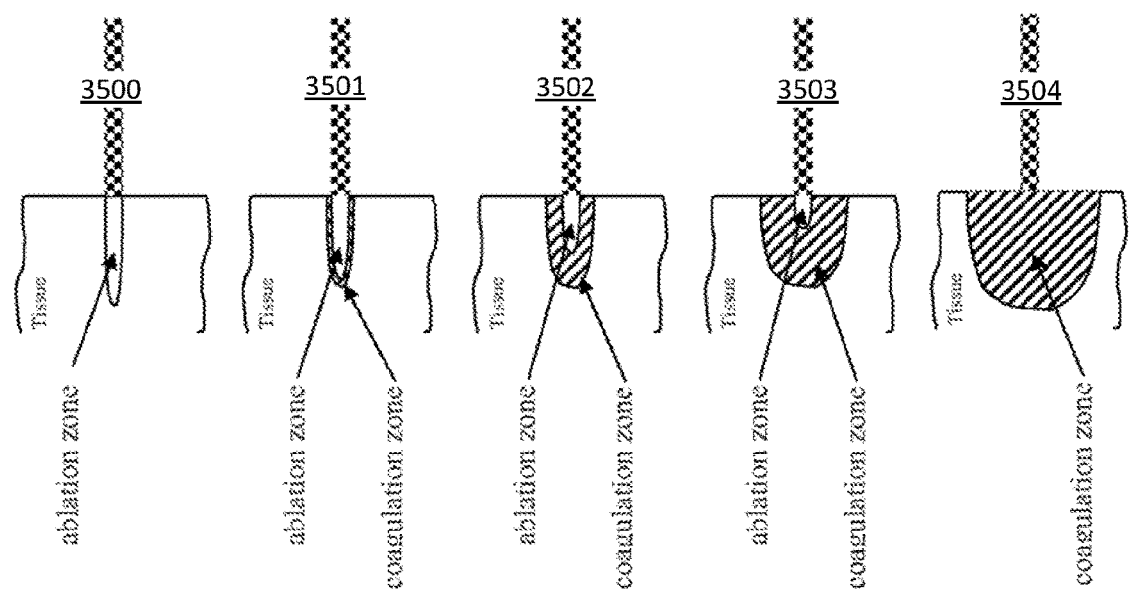
FIG. 35 shows representative tissue effects and their corresponding dynamic pulse schemes, in accordance with embodiments of the present invention.

FIG. 35 shows general representations of tissue effects caused by exemplary dynamic pulse configurations that blend the cutting and coagulative tissue effects. The pulsed treatment beam 3500 shows the ablative removal of tissue including flash vaporization with no appreciable thermal damage to the remaining tissue. The pulsed treatment beam 3501 shows primarily ablative removal of tissue with a small amount of thermal damage to the remaining tissue. The pulsed treatment beam 3502 shows ablative removal of tissue with a moderate amount of thermal damage to the remaining tissue. The pulsed treatment beam 3503 shows ablative removal of a small amount of tissue with a large amount of thermal damage to the remaining tissue. Finally the pulsed treatment beam 3504 shows a large area of coagulated tissue with no appreciable ablative removal of tissue.

The diverse range of tissue interactions and surgical capabilities coupled with the portability and a self-contained power source, such as a battery, make the system advantageous for field use. Surgical interventions can be performed in emergency, rescue and military field situations. Additionally, the advantages of a Flash Vaporization system, including in particular soft tissue-selective flash vaporization, are well suited for robotic surgery.

It should be appreciated that the processor described above may comprise a processor system having one or more processors, and that the tangible data storage medium of the processor may comprise a computer program configured to implement the methods of tissue treatment illustrated above, for example in accordance with the pulse sequences described above.

It should be appreciated that the specific steps illustrated in the flow diagrams above provide particular methods of treating a patient or operating a laser system, according to embodiments of the present invention. Other sequences of steps may also be performed according to alternative embodiments. For example, alternative embodiments of the present invention may perform the steps outlined above in a different order. Moreover, the individual steps illustrated in the figures may include multiple sub-steps that may be performed in various sequences as appropriate to the individual step. Furthermore, additional steps may be added or removed depending on the particular applications. One of ordinary skill in the art would recognize many variations, modifications, and alternatives.

While the exemplary embodiments have been described in some detail, by way of example and for clarity of understanding, those of skill in the art will recognize that a variety of modifications, adaptations, and changes may be employed. Hence, the scope of the present invention should be limited solely by the appended claims.

The invention claimed is:

1. A method for tissue selective ablation in a surgical field including a first soft tissue type and a second soft tissue type, comprising:

setting laser parameters on a laser controller above a first ablation threshold for the first soft tissue type, and below a second ablation threshold for the second soft tissue type;

generating a pulsed laser beam using the laser parameters; and moving the pulsed laser beam along a boundary between first and second soft tissue types within the surgical field to selectively remove the first soft tissue type relative to tissue of the second soft tissue type, wherein during said moving the pulsed laser beam along the boundary pulses of the pulsed laser beam are delivered to target tissue of the first soft tissue type causing a first tissue removal rate, and to target tissue of the second soft tissue type, causing a second tissue removal rate, the first tissue removal rate being at least four times faster than the second tissue removal rate; and wherein the first tissue type is a tissue type selected from a group including tissue surrounding a nerve, tissue surrounding a vessel, tissue surrounding a tendon, tissue surrounding a ligament, thyroid tissue, parathyroid tissue, prostate tissue, facial tissue, tonsil tissue, kidney tissue, mucosal tissue, colon tissue and tissue surrounding a tumor; and the second tissue type is a tissue type selected from a group including perineural tissue, vessel tissue, tonsillar hemi-capsule tissue, muscularis, malignant brain tissue, colon tumor tissue bone, tendons, ligaments, and tumor tissue.

2. The method of claim 1, wherein pulses of the pulsed laser beam delivered to target tissue of the first soft tissue type cause ablation, and pulses of the pulsed laser beam delivered to target tissue of the second soft tissue type, do not result in destruction of the target tissue of the second soft tissue type.

3. The method of claim 1, wherein pulses of the pulsed laser beam delivered to target tissue of the first soft tissue type deliver a volumetric power density to an interaction volume in the target tissue of the first soft tissue type that induces spinodal decomposition in the tissue and kinetic energy confined within the interaction volume to eject tissue of the first soft tissue type; and wherein pulses of the pulsed laser beam delivered to tissue of the second soft tissue type do not create kinetic energy to remove tissue of the second soft tissue type.

4. The method of claim 1, wherein the laser parameters specify one or more of a spot size adjustment and a pulse power adjustment, and generating the pulsed laser beam includes producing laser pulses set according to the laser parameters, and having a wavelength between 1400 and 1520 nm or between 1860 and 2500 nm, having between 1 and 40 milliJoules per pulse, and having a pulse duration less than 200 nsec.

5. The method of claim 1, wherein moving the pulsed laser beam includes:

delivering pulses of the pulsed laser beam to a spot on target tissue, whereby an interaction volume defined by area of the spot and a penetration depth (1/e) for the pulse in water, the interaction volume having a ratio of depth to width from 2:1 to 1:6; and wherein pulse parameters are set to be tissue type selective.

6. The method of claim 1, including setting the laser parameters in response to a user input indicating the first soft tissue type.

7. The method of claim 1, wherein the pulsed laser beam has a wavelength between 1860 and 2500 nm.

8. The method of claim 1, including selecting a pulse repetition rate for the pulsed laser beam in response to user input in a range from single shot to 2 kHz.

9. The method of claim 1, including delivering the pulsed laser beam using a silica optical fiber, with energy and pulse duration combinations that are below the damage threshold for the silica optical fiber.

10. The method of claim 1, wherein pulses of the pulsed laser beam delivered to tissue of the first type induce spinodal decomposition within an interaction volume of target tissue of the first type that creates kinetic energy to remove tissue of the first soft tissue type within the interaction volume; and
wherein pulses of the pulsed laser beam delivered to tissue of the second soft tissue type do not create kinetic energy to remove tissue of the second soft tissue type within the interaction volume.

11. The method of claim 9, wherein the volume of tissue of the first soft tissue type is ejected without stress propagation of mechanical energy into the tissue adjacent to the target volume.

12. The method of claim 1, wherein:
pulses of the pulsed laser beam have a wavelength with an associated optical penetration depth D in tissue of the first soft tissue type, an energy per pulse, a fluence $\phi$, a spot area and a pulse duration $t_p$ toward an interaction volume of a target tissue; and including:
generating pressure within the interaction volume of the target tissue of the first soft tissue type, which causes ejection of the target tissue within the interaction volume and heating the interaction volume above a spinodal decomposition threshold at the optical penetration depth using the laser pulses, wherein the wavelength is between 1400 and 1520 nm or between 1860 and 2500 nm and the energy per pulse between 0.5 milliJoules and 40 milliJoules, wherein the interaction volume is a function of the optical penetration depth D and the spot area of the pulses of the pulsed laser beam incident on the target tissue, where the spot area has a minimum width W, and wherein the optical penetration depth D is a function of an absorption coefficient pa of the target tissue that is determined by tissue properties and the wavelength, and wherein the optical penetration depth and minimum spot width satisfy a condition that D is within a range of ⅙ W to 2 W, the pulse duration $t_p$ meets stress confinement conditions for the interaction volume including:
$t_p < 1/\mu_a v_s$ and
$t_p < W/2v_s$, where $v_s$=speed of sound in the target tissue, and further that the pulse duration $t_p$ is less than 200 nsec; and
wherein the energy per pulse of the laser pulses in the heating of the interaction volume heats water within the interaction volume to induce a phase transition by spinodal decomposition within the interaction volume creating said pressure, and the fluence $\phi$, satisfies:

$$\phi = \frac{t_L}{1 - e^{t_L}} \frac{P}{\Gamma \mu_a}$$

for the first soft tissue type but not for the second soft tissue type, where:
P=pressure to eject the target tissue
$t_L = t_p \mu_a v_s$
$\Gamma$=dimensionless strength parameter of the target tissue.

13. A method for tissue selective ablation in a surgical field including first and second soft tissue types, comprising:
setting laser parameters above a first ablation threshold for the first soft tissue type, and below a second ablation threshold for the second soft tissue type;
generating a pulsed laser beam using the laser parameters; and
moving the pulsed laser beam along a boundary between first and second soft tissue types within the surgical field to selectively remove the first soft tissue type relative to tissue of the second soft tissue type, wherein during said moving the pulsed laser beam along the boundary pulses of the pulsed laser beam are delivered to target tissue of the first soft tissue type causing a first tissue removal rate, and to target tissue of the second soft tissue type causing a second tissue removal rate, wherein the first soft tissue type comprises tissue next to a nerve or vessel, and the second soft tissue type is perineural tissue of the nerve or vessel tissue.

14. A method for tissue selective ablation in a surgical field including first and second soft tissue types, comprising:
setting laser parameters above a first ablation threshold for the first soft tissue type, and below a second ablation threshold for the second soft tissue type;
generating a pulsed laser beam using the laser parameters; and
moving the pulsed laser beam along a boundary between first and second soft tissue types within the surgical field to selectively remove the first soft tissue type relative to tissue of the second soft tissue type, wherein during said moving the pulsed laser beam along the boundary pulses of the pulsed laser beam are delivered to target tissue of the first soft tissue type causing a first tissue removal rate, and to target tissue of the second soft tissue type causing a second tissue removal rate, wherein the first soft tissue type comprises tonsillar tissue, and the second soft tissue type is tissue of a tonsillar capsule.

15. A method for tissue selective ablation in a surgical field including first and second soft tissue types, comprising:
setting laser parameters above a first ablation threshold for the first soft tissue type, and below a second ablation threshold for the second soft tissue type;
generating a pulsed laser beam using the laser parameters; and
moving the pulsed laser beam along a boundary between first and second soft tissue types within the surgical field to selectively remove the first soft tissue type relative to tissue of the second soft tissue type, wherein during said moving the pulsed laser beam along the boundary pulses of the pulsed laser beam are delivered to target tissue of the first soft tissue type causing a first tissue removal rate, and to target tissue of the second soft tissue type causing a second tissue removal rate, wherein the first soft tissue type comprises tissue in a first layer, and the second soft tissue type comprises tissue beneath the first layer.

16. A method for tissue selective ablation in a surgical field including first and second soft tissue types, comprising:
setting laser parameters above a first ablation threshold for the first soft tissue type, and below a second ablation threshold for the second soft tissue type;
generating a pulsed laser beam using the laser parameters; and
moving the pulsed laser beam along a boundary between first and second soft tissue types within the surgical field to selectively remove the first soft tissue type relative to tissue of the second soft tissue type, wherein during said moving the pulsed laser beam along the boundary pulses of the pulsed laser beam are delivered to target tissue of the first soft tissue type causing a first tissue removal rate, and to target tissue of the second soft tissue type causing a second tissue removal rate, wherein the first soft tissue type comprises mucosal tissue, and the second soft tissue type comprises muscularis tissue.

17. A method for tissue selective ablation in a surgical field including first and second soft tissue types, comprising:
setting laser parameters above a first ablation threshold for the first soft tissue type, and below a second ablation threshold for the second soft tissue type;
generating a pulsed laser beam using the laser parameters; and
moving the pulsed laser beam along a boundary between first and second soft tissue types within the surgical field to selectively remove the first soft tissue type relative to tissue of the second soft tissue type, wherein during said moving the pulsed laser beam along the boundary pulses of the pulsed laser beam are delivered to target tissue of the first soft tissue type causing a first tissue removal rate, and to target tissue of the second soft tissue type, causing a second tissue removal rate, wherein the first soft tissue type comprises tissue next to a tumor, and the second soft tissue type is tumor tissue.

18. An apparatus for tissue-type selective ablation, comprising:
a laser system to generate a pulsed laser beam according to laser parameters;
a controller including a user input device to set one or more of the laser parameters above a first ablation threshold for a first soft tissue type, and below a second ablation threshold for a second soft tissue type; and
a beam delivery device coupled to the laser system to deliver the pulsed laser beam to spots on the tissue, wherein pulses of the pulsed laser beam are characterized as a result of the laser parameters by causing a first tissue removal rate during delivery to tissue of the first tissue type, and causing second tissue removal rate during delivery to tissue of the second tissue type, the first tissue removal rate being at least four times faster than the second tissue removal rate; and
wherein the first tissue type is a tissue type selected from a group including tissue surrounding a nerve, tissue surrounding a vessel, tissue surrounding a tendon, tissue surrounding a ligament, thyroid tissue, parathyroid tissue, prostate tissue, facial tissue, tonsil tissue, kidney tissue, mucosal tissue, colon tissue and tissue surrounding a tumor; and the second tissue type is a tissue type selected from a group including perineural tissue, vessel tissue, tonsillar hemi-capsule tissue, muscularis, malignant brain tissue, colon tumor tissue bone, tendons, ligaments, and tumor tissue.

19. The apparatus of claim 18, the pulsed laser beam having a wavelength between 1400 and 1520 nm or between 1860 and 2500 nm, having between 1 and 40 milliJoules per pulse, and having a pulse duration less than 200 nsec.

20. The apparatus of claim 18, wherein the beam delivery device includes a silica waveguide.

21. The apparatus of claim 18, wherein the laser parameters include a pulse repetition rate settable from single shot to 2 kHz.

22. The apparatus of claim 18, wherein the laser system includes a gain medium comprising a thulium doped host.

23. The apparatus of claim 18, wherein the beam delivery device comprises an endoscope including one or more waveguides.

24. The apparatus of claim 18, wherein pulses of the pulsed laser beam delivered to tissue of the first type induce spinodal decomposition within an interaction volume of target tissue of the first type that creates kinetic energy to remove tissue of the first type within the interaction volume without depositing energy in the tissue adjacent a cavity left by the removed tissue; and
wherein pulses of the pulsed laser beam delivered to tissue of the second type do not create kinetic energy to remove tissue of the second type within the interaction volume.

25. The apparatus of claim 18, wherein pulses of the pulsed laser beam delivered to target tissue of the first soft tissue type cause ablation of tissue, and pulses of the pulsed laser beam delivered to target tissue of the second soft tissue type, do not result in destruction of the target tissue of the second soft tissue type.

26. The apparatus of claim 18, wherein pulses of the pulsed laser beam delivered to target tissue of the first soft tissue type deliver a volumetric power density to an interaction volume in the target tissue of the first soft tissue type that induces spinodal decomposition in the tissue and kinetic energy confined within the interaction volume to eject tissue of the first soft tissue type.

27. The apparatus of claim 18, wherein the laser parameters specify one or more of a spot size adjustment and a pulse power adjustment, and generating the pulsed laser beam includes producing laser pulses set according to the laser parameters, and having a wavelength between 1400 and 1520 nm or between 1860 and 2500 nm, having between 1 and 40 milliJoules per pulse, and having a pulse duration less than 200 nsec.

28. An apparatus for tissue-type selective ablation, comprising:
a laser system to generate a pulsed laser beam according to laser parameters;
a controller including a user input device to set one or more of the laser parameters above a first ablation threshold for a first soft tissue type, and below a second ablation threshold for a second soft tissue type; and
a beam delivery device coupled to the laser system to deliver the pulsed laser beam to spots on the tissue, wherein pulses of the pulsed laser beam are characterized as a result of the laser parameters by causing a first tissue removal rate during delivery to tissue of the first tissue type, causing a second tissue removal rate during delivery to tissue of the second tissue type, the first tissue removal rate being at least four times faster than the second tissue removal rate, wherein the first soft tissue type comprises tissue next to a nerve or vessel, and the second soft tissue type is perineural tissue of the nerve or vessel tissue.

29. An apparatus for tissue-type selective ablation, comprising:
a laser system to generate a pulsed laser beam according to laser parameters;
a controller including a user input device to set one or more of the laser parameters above a first ablation threshold for a first soft tissue type, and below a second ablation threshold for a second soft tissue type; and
a beam delivery device coupled to the laser system to deliver the pulsed laser beam to spots on the tissue, wherein pulses of the pulsed laser beam are characterized as a result of the laser parameters by causing a first tissue removal rate during delivery to tissue of the first tissue type, and to target tissue of the second soft tissue type, causing a second tissue removal rate during delivery to tissue of the second tissue type, the first tissue removal rate being at least four times faster than the second tissue removal rate, the first tissue removal rate being at least four times faster than the second tissue removal rate, wherein the first soft tissue type comprises tonsillar tissue, and the second soft tissue type is tissue of a tonsillar capsule.

30. An apparatus for tissue-type selective ablation, comprising:
a laser system to generate a pulsed laser beam according to laser parameters;
a controller including a user input device to set one or more of the laser parameters above a first ablation threshold for a first soft tissue type, and below a second ablation threshold for a second soft tissue type; and
a beam delivery device coupled to the laser system to deliver the pulsed laser beam to spots on the tissue, wherein pulses of the pulsed laser beam are characterized as a result of the laser parameters by causing a first tissue removal rate during delivery to tissue of the first tissue type, and to target tissue of the second soft tissue type, causing a second tissue removal rate during delivery to tissue of the second tissue type, the first tissue removal rate being at least four times faster than the second tissue removal rate, the first tissue removal rate being at least four times faster than the second tissue removal rate, wherein the first soft tissue type comprises tissue in a first layer, and the second soft tissue type comprises tissue beneath the first layer.

31. An apparatus for tissue-type selective ablation, comprising:
a laser system to generate a pulsed laser beam according to laser parameters;
a controller including a user input device to set one or more of the laser parameters above a first ablation threshold for a first soft tissue type, and below a second ablation threshold for a second soft tissue type; and
a beam delivery device coupled to the laser system to deliver the pulsed laser beam to spots on the tissue, wherein pulses of the pulsed laser beam are characterized as a result of the laser parameters by causing a first tissue removal rate during delivery to tissue of the first tissue type, and to target tissue of the second soft tissue type, causing a second tissue removal rate during delivery to tissue of the second tissue type, the first tissue removal rate being at least four times faster than the second tissue removal rate, the first tissue removal rate being at least four times faster than the second tissue removal rate, wherein the first soft tissue type comprises mucosal tissue, and the second soft tissue type comprises muscularis tissue.

32. An apparatus for tissue-type selective ablation, comprising:
a laser system to generate a pulsed laser beam according to laser parameters;
a controller including a user input device to set one or more of the laser parameters above a first ablation threshold for a first soft tissue type, and below a second ablation threshold for a second soft tissue type; and
a beam delivery device coupled to the laser system to deliver the pulsed laser beam to spots on the tissue, wherein pulses of the pulsed laser beam are characterized as a result of the laser parameters by causing a first tissue removal rate during delivery to tissue of the first tissue type, and to target tissue of the second soft tissue type, causing a second tissue removal rate during delivery to tissue of the second tissue type, the first tissue removal rate being at least four times faster than the second tissue removal rate, the first tissue removal rate being at least four times faster than the second tissue removal rate, wherein the first soft tissue type comprises tissue next to a tumor, and the second soft tissue type is tumor tissue.

33. The apparatus of claim 18, wherein the controller includes memory storing a table of laser parameter settings specifying laser parameters that fall below an ejection pressure threshold for a selected protected tissue, and above a pressure threshold for a selected target tissue.

34. The method of claim 1, wherein the first soft tissue type comprises thyroid tissue, and the second soft tissue type is perineural tissue of the nerve or nerve tissue.

35. The method of claim 1, wherein the first soft tissue type comprises thyroid tissue, and the second soft tissue type is vessel tissue.

36. The method of claim 1, wherein the first soft tissue type comprises parathyroid tissue, and the second soft tissue type is perineural tissue of the nerve or nerve tissue.

37. The method of claim 1, wherein the first soft tissue type comprises parathyroid tissue, and the second soft tissue type is perineural tissue of the nerve or nerve tissue.

38. The apparatus of claim 18, wherein the first soft tissue type comprises thyroid tissue, and the second soft tissue type is perineural tissue of the nerve or nerve tissue.

39. The apparatus of claim 18, wherein the first soft tissue type comprises thyroid tissue, and the second soft tissue type is vessel tissue.

40. The apparatus of claim 18, wherein the first soft tissue type comprises parathyroid tissue, and the second soft tissue type is perineural tissue of the nerve or nerve tissue.

41. The apparatus of claim 18, wherein the first soft tissue type comprises parathyroid tissue, and the second soft tissue type is perineural tissue of the nerve or nerve tissue.

* * * * *